US012753399B2

(12) United States Patent
Andersen et al.

(10) Patent No.: US 12,753,399 B2
(45) Date of Patent: Oct. 6, 2026

(54) ALPHA-AMYLASE VARIANTS AND POLYNUCLEOTIDES ENCODING SAME

(71) Applicant: Novozymes A/S, Bagsvaerd (DK)

(72) Inventors: Carsten Andersen, Vaerloese (DK); Thomas Agersten Poulsen, Ballerup (DK); Dorota Nissen, Vedbaek (DK); Marie Thryøse Kruse, Vaerloese (DK); Sarah Schultheis Elliott, Raleigh, NC (US); Shiro Fukuyama, Chiba (JP)

(73) Assignee: Novozymes A/S, Bagsvaerd (DK)

( * ) Notice: Subject to any disclaimer, the term of this patent is extended or adjusted under 35 U.S.C. 154(b) by 630 days.

(21) Appl. No.: 17/797,351

(22) PCT Filed: Feb. 9, 2021

(86) PCT No.: PCT/US2021/017173

§ 371 (c)(1),
(2) Date: Aug. 3, 2022

(87) PCT Pub. No.: WO2021/163011

PCT Pub. Date: Aug. 19, 2021

(65) Prior Publication Data

US 2023/0142991 A1 May 11, 2023

Related U.S. Application Data

(60) Provisional application No. 62/972,132, filed on Feb. 10, 2020, provisional application No. 63/032,779, filed on Jun. 1, 2020, provisional application No. 63/073,968, filed on Sep. 3, 2020.

(51) Int. Cl.

| | |
|---|---|
| ***C12N 9/28*** | (2006.01) |
| ***C12N 9/34*** | (2006.01) |
| ***C12P 7/06*** | (2006.01) |

(52) U.S. Cl.

CPC ......... *C12N 9/2417* (2013.01); *C12N 9/2428* (2013.01); *C12P 7/06* (2013.01); *C12Y 302/01001* (2013.01)

(58) Field of Classification Search

CPC ....... C12N 9/2417; C12N 9/2428; C12P 7/06; C12Y 302/01001; C07K 2319/02; C07K 2319/21; Y02E 50/10

See application file for complete search history.

(56) References Cited

U.S. PATENT DOCUMENTS

| | | | | |
|---|---|---|---|---|
| 9,040,278 B2 * | 5/2015 | Cascao-Pereira | C12P 19/02 435/162 |
| 9,040,279 B2 * | 5/2015 | Breneman | C12P 7/00 435/162 |
| 9,090,887 B2 | 7/2015 | Cuevas et al. | |
| 2018/0265853 A1 | 9/2018 | Rice et al. | |
| 2019/0010473 A1 | 1/2019 | Koops et al. | |
| 2023/0142991 A1 | 5/2023 | Andersen et al. | |
| 2023/0235367 A1 * | 7/2023 | Andersen | C12P 7/10 435/161 |

FOREIGN PATENT DOCUMENTS

| | | |
|---|---|---|
| CN | 102260694 A | 11/2011 |
| WO | 2009149283 A1 | 12/2009 |
| WO | 2009149395 A2 | 12/2009 |
| WO | 2013057141 A2 | 4/2013 |
| WO | 2017133974 A1 | 8/2017 |
| WO | 2018002360 A1 | 1/2018 |
| WO | 2019014118 A1 | 1/2019 |
| WO | 2019186371 A1 | 10/2019 |

OTHER PUBLICATIONS

Banerjee et al., Improving enzymes for biomass conversion: A basic research perspective. Bioenerg. Res., 2010, vol. 3: 82-92. ( Year: 2010).*

Broun et al., Catalytic plasticity of fatty acid modification enzymes underlying chemical diversity of plant lipids. Science, 1998, vol. 282: 1315-1317. (Year: 1998).*

Chica et al., Semi-rational approaches to engineering enzyme activity: combining the benefits of directed evolution and rational design. Curr. Opi. Biotechnol., 2005, vol. 16: 378-384. (Year: 2005).*

Devos et al., Practical limits of function prediction. Proteins: Structure, Function, and Genetics. 2000, vol. 41: 98-107. (Year: 2000).*

Seffernick et al., Melamine deaminase and Atrazine chlorohydrolase: 98 percent identical but functionally different. J. Bacteriol., 2001, vol. 183 (8): 2405-2410. (Year: 2001).*

Sen et al., Developments in directed evolution for enzyme functions. Appl. Biochem. Biotechnol., 2007, vol. 143: 212-223. (Year: 2007).*

(Continued)

*Primary Examiner* — Ganapathirama Raghu

(74) *Attorney, Agent, or Firm* — David A. Fazzolare

(57) ABSTRACT

The present invention relates to isolated alpha-amylase variants of a parent alpha-amylase, comprising an alteration at one or more positions corresponding to positions 196, 1, 2, 3, 4, 5, 6, 7, 8, 9, 10, 11, 12, 13, 14, 15, 16, 28, 38, 39, 43, 54, 56, 57, 64, 67, 68, 70, 71, 86, 89, 90, 94, 96, 99, 101, 103, 107, 108, 110, 113, 114, 117, 127, 134, 138, 142, 150, 151, 152, 156, 169, 171, 174, 179, 183, 193, 199, 200, 204, 205, 207, 208, 209, 212, 218, 221, 222, 224, 233, 241, 245, 259, 275, 278, 281, 282, 283, 284, 285, 308, 323, 335, 348, 359, 382, 386, 388, 392, 394, 396, 412, 414, 417, 424, 428, 457, 459, 466, 479, 489, 511, 533, 534, 542, 543, 545, 547, 549, 550, 551, 560, 566, 570, 574, 575, 576, 577, 578, 580, 581, 582, 589, 592, 599, 603, 605, 608, 614, 619, or 626 of the polypeptide of SEQ ID NO: 1, wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 1, SEQ ID NO: 2, SEQ ID NO: 3, or SEQ ID NO: 4. The alpha-amylase variants of the invention have increased stability at pH 4.0 and 32° C. compared to the parent alpha-amylase.

33 Claims, No Drawings

Specification includes a Sequence Listing.

(56) References Cited

OTHER PUBLICATIONS

Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Biesgen et al, 2002, Phytochemistry reviews 1(1), 79-85.
Liu et al, 2012, J Appl Microbiol 113(3), 541-549.
Nielsen et al, 2000, Biochim Biophys Acta 1543, 253-274.
Uchino, 1982, J Agric Biol Chem 46(1), 7-13.
WO 2019-014118 A1—Database accession No. BGA91894.
WO 2019-014118 A1—Uniprot accession No. BGA91883.

* cited by examiner

```
SEQUENCE LISTING

<160> NUMBER OF SEQ ID NOS: 19

<210> SEQ ID NO 1
<211> LENGTH: 626
<212> TYPE: PRT
<213> ORGANISM: Bacillus amyloliquefaciens

<400> SEQUENCE: 1

Glu Thr Ala Asn Lys Ser Asn Lys Val Thr Ala Ser Ser Val Lys Asn
1               5                   10                  15

Gly Thr Ile Leu His Ala Trp Asn Trp Ser Phe Asn Thr Leu Thr Gln
            20                  25                  30

Asn Met Lys Asp Ile Arg Asp Ala Gly Tyr Ala Ala Ile Gln Thr Ser
        35                  40                  45

Pro Ile Asn Gln Val Lys Glu Gly Asn Gln Gly Asp Lys Ser Met Arg
    50                  55                  60

Asn Trp Tyr Trp Leu Tyr Gln Pro Thr Ser Tyr Gln Ile Gly Asn Arg
65                  70                  75                  80

Tyr Leu Gly Thr Glu Gln Glu Phe Lys Asp Met Cys Ala Ala Ala Glu
                85                  90                  95

Lys Tyr Gly Val Lys Val Ile Val Asp Ala Val Ile Asn His Thr Thr
            100                 105                 110

Ser Asp Tyr Gly Ala Ile Ser Asp Glu Ile Lys Arg Ile Pro Asn Trp
        115                 120                 125

Thr His Gly Asn Thr Gln Ile Lys Asn Trp Ser Asp Arg Trp Asp Val
    130                 135                 140

Thr Gln Asn Ser Leu Leu Gly Leu Tyr Asp Trp Asn Thr Gln Asn Thr
145                 150                 155                 160
```

```
Glu Val Gln Ala Tyr Leu Lys Arg Phe Leu Glu Arg Ala Leu Asn Asp
                165                 170                 175

Gly Ala Asp Gly Phe Arg Tyr Asp Ala Ala Lys His Ile Glu Leu Pro
            180                 185                 190

Asp Asp Gly Asn Tyr Gly Ser Gln Phe Trp Pro Asn Ile Thr Asn Thr
        195                 200                 205

Ser Ala Glu Phe Gln Tyr Gly Glu Ile Leu Gln Asp Ser Ala Ser Arg
    210                 215                 220

Asp Thr Ala Tyr Ala Asn Tyr Met Asn Val Thr Ala Ser Asn Tyr Gly
225                 230                 235                 240

His Ser Ile Arg Ser Ala Leu Lys Asn Arg Asn Leu Ser Val Ser Asn
                245                 250                 255

Ile Ser His Tyr Ala Ser Asp Val Ser Ala Asp Lys Leu Val Thr Trp
            260                 265                 270

Val Glu Ser His Asp Thr Tyr Ala Asn Asp Asp Glu Glu Ser Thr Trp
        275                 280                 285

Met Ser Asp Asp Asp Ile Arg Leu Gly Trp Ala Val Ile Gly Ser Arg
    290                 295                 300

Ser Gly Ser Thr Pro Leu Phe Phe Ser Arg Pro Glu Gly Gly Gly Asn
305                 310                 315                 320

Gly Val Arg Phe Pro Gly Lys Ser Gln Ile Gly Asp Arg Gly Ser Ala
                325                 330                 335

Leu Phe Lys Asp Gln Ala Ile Thr Ala Val Asn Thr Phe His Asn Val
            340                 345                 350

Met Ala Gly Gln Pro Glu Glu Leu Ser Asn Pro Asn Gly Asn Asn Gln
        355                 360                 365

Ile Phe Met Asn Gln Arg Gly Ser Lys Gly Val Val Leu Ala Asn Ala
    370                 375                 380

Gly Ser Ser Ser Val Thr Ile Asn Thr Ser Ala Lys Leu Pro Asp Gly
385                 390                 395                 400

Arg Tyr Asp Asn Arg Ala Gly Ala Gly Ser Phe Gln Val Ala Asn Gly
                405                 410                 415

Lys Leu Thr Gly Thr Ile Asn Ala Arg Ser Ala Ala Val Leu Tyr Pro
            420                 425                 430

Asp Asp Ile Gly Asn Ala Pro His Val Phe Leu Glu Asn Tyr Gln Thr
        435                 440                 445

Gly Ala Val His Ser Phe Asn Asp Gln Leu Thr Val Thr Leu Arg Ala
    450                 455                 460

Asn Ala Lys Thr Thr Lys Ala Val Tyr Gln Ile Asn Asn Gly Gln Gln
465                 470                 475                 480

Thr Ala Phe Lys Asp Gly Asp Arg Leu Thr Ile Gly Lys Gly Asp Pro
                485                 490                 495

Ile Gly Thr Thr Tyr Asn Ile Lys Leu Thr Gly Thr Asn Gly Glu Gly
            500                 505                 510

Ala Ala Arg Thr Gln Glu Tyr Lys Phe Val Lys Lys Asp Pro Ser Gln
        515                 520                 525

Thr Asn Ile Ile Gly Tyr Gln Asn Pro Asp His Trp Gly Gln Val Asn
    530                 535                 540

Ala Tyr Ile Tyr Lys His Asp Gly Gly Arg Ala Ile Glu Leu Thr Gly
545                 550                 555                 560

Ser Trp Pro Gly Lys Ala Met Thr Lys Asn Ala Asp Gly Met Tyr Thr
                565                 570                 575
```

```
Leu Thr Leu Pro Glu Asn Ala Asp Thr Ala Asn Ala Lys Val Ile Phe
            580                 585                 590

Asn Asn Gly Ser Ala Gln Val Pro Gly Gln Asn Gln Pro Gly Phe Asp
        595                 600                 605

Tyr Val Gln Asn Gly Leu Tyr Asn Asn Ser Gly Leu Asn Gly Tyr Leu
    610                 615                 620

Pro His
625


<210> SEQ ID NO 2
<211> LENGTH: 626
<212> TYPE: PRT
<213> ORGANISM: Bacillus cereus

<400> SEQUENCE: 2

Glu Thr Ala Asn Lys Ser Asn Glu Ala Ala Ala Ser Ser Val Lys Asn
1               5                   10                  15

Gly Thr Ile Leu His Ala Trp Asn Trp Ser Phe Asn Thr Leu Thr Gln
            20                  25                  30

Asn Met Lys Asp Ile Arg Asp Ala Gly Tyr Ala Ala Ile Gln Thr Ser
        35                  40                  45

Pro Ile Asn Gln Val Lys Glu Gly Asn Gln Gly Asp Lys Ser Met Arg
    50                  55                  60

Asn Trp Tyr Trp Leu Tyr Gln Pro Thr Ser Tyr Gln Ile Gly Asn Arg
65                  70                  75                  80

Tyr Leu Gly Thr Glu Gln Glu Phe Lys Asp Met Cys Ala Ala Ala Glu
                85                  90                  95

Lys Tyr Gly Val Lys Val Ile Val Asp Ala Val Ile Asn His Thr Thr
            100                 105                 110

Ser Asp Tyr Ala Ala Ile Ser Asp Glu Ile Lys Arg Ile Pro Asn Trp
        115                 120                 125

Thr His Gly Asn Thr Gln Ile Lys Asn Trp Ser Asp Arg Trp Asp Val
    130                 135                 140

Thr Gln Asn Ser Leu Leu Gly Leu Tyr Asp Trp Asn Thr Gln Asn Thr
145                 150                 155                 160

Glu Val Gln Ala Tyr Leu Lys Arg Phe Leu Glu Arg Ala Leu Asn Asp
                165                 170                 175

Gly Ala Asp Gly Phe Arg Tyr Asp Ala Ala Lys His Ile Glu Leu Pro
            180                 185                 190

Asp Asp Gly Asn Tyr Gly Ser Arg Phe Trp Pro Asn Ile Thr Asn Thr
        195                 200                 205

Ser Ala Glu Phe Gln Tyr Gly Glu Ile Leu Gln Asp Ser Ala Ser Arg
    210                 215                 220

Asp Thr Ala Tyr Ala Asn Tyr Met Asn Val Thr Ala Ser Asn Tyr Gly
225                 230                 235                 240

His Ser Ile Arg Ser Ala Leu Lys Asn Arg Asn Leu Ser Val Ser Asn
                245                 250                 255

Ile Ser His Tyr Ala Ser Asp Val Ser Ala Asp Lys Leu Val Thr Trp
            260                 265                 270

Val Glu Ser His Asp Thr Tyr Ala Asn Asp Glu Glu Glu Ser Thr Trp
        275                 280                 285

Met Ser Asp Asp Asp Ile Arg Leu Gly Trp Ala Val Ile Gly Ser Arg
    290                 295                 300

Ser Gly Ser Thr Pro Leu Phe Phe Ser Arg Pro Glu Gly Gly Gly Asn
305                 310                 315                 320
```

Gly Val Arg Phe Pro Gly Lys Ser Gln Ile Gly Asp Arg Gly Ser Ala
325 330 335

Leu Phe Lys Asp Gln Ala Ile Thr Ala Val Asn Gln Phe His Asn Val
340 345 350

Met Val Gly Gln Pro Glu Glu Leu Ser Asn Pro Asn Gly Asn Asn Gln
355 360 365

Ile Phe Met Asn Gln Arg Gly Ser Lys Gly Val Val Leu Ala Asn Ala
370 375 380

Gly Ser Ser Ser Val Thr Val Asn Thr Ser Thr Lys Leu Pro Asp Gly
385 390 395 400

Arg Tyr Asp Asn Arg Ala Gly Ala Gly Ser Phe Gln Val Ala Asn Gly
405 410 415

Lys Leu Thr Gly Thr Ile Asn Ala Arg Ser Ala Ala Val Leu Tyr Ser
420 425 430

Asp Asp Ile Gly Asn Ala Pro Gln Val Phe Leu Glu Asn Tyr Gln Thr
435 440 445

Gly Ala Val His Ser Phe Asn Asp Gln Leu Thr Val Thr Leu Arg Ala
450 455 460

Asn Ala Lys Thr Thr Lys Ala Val Tyr Gln Ile Asn Asn Gly Gln Gln
465 470 475 480

Thr Ala Phe Lys Asp Gly Asp Arg Leu Thr Ile Gly Lys Gly Asp Pro
485 490 495

Ile Gly Thr Thr Tyr Asn Ile Lys Leu Thr Gly Thr Asn Gly Glu Gly
500 505 510

Ala Glu Arg Thr Gln Glu Tyr Thr Phe Val Lys Lys Asp Pro Ala Gln
515 520 525

Thr Asn Ile Ile Gly Tyr Gln Asn Pro Asp His Trp Gly Gln Val Asn
530 535 540

Ala Tyr Ile Tyr Lys His Asp Gly Gly Arg Ala Ile Glu Leu Thr Gly
545 550 555 560

Ser Trp Pro Gly Lys Ala Met Thr Lys Asn Ala Asn Gly Ile Tyr Thr
565 570 575

Leu Thr Leu Pro Ala Asn Ala Asp Thr Ala Asn Ala Lys Val Ile Phe
580 585 590

Asn Asn Gly Ser Ala Gln Val Pro Gly Gln Asn Gln Pro Gly Phe Asp
595 600 605

Tyr Val Gln Asn Gly Leu Tyr Asn Asn Ser Gly Leu Asn Gly Tyr Leu
610 615 620

Pro His
625

<210> SEQ ID NO 3
<211> LENGTH: 627
<212> TYPE: PRT
<213> ORGANISM: Bacillus subtilis

<400> SEQUENCE: 3

Glu Thr Ala Asn Lys Ser Asn Glu Leu Thr Ala Pro Ser Ile Lys Ser
1 5 10 15

Gly Thr Ile Leu His Ala Trp Asn Trp Ser Phe Asn Thr Leu Lys His
20 25 30

Asn Met Lys Asp Ile His Asp Ala Gly Tyr Thr Ala Ile Gln Thr Ser
35 40 45

```
Pro Ile Asn Gln Val Lys Glu Gly Asn Gln Gly Asp Lys Ser Met Ser
    50                  55                  60

Asn Trp Tyr Trp Leu Tyr Gln Pro Thr Ser Tyr Gln Ile Gly Asn Arg
65                  70                  75                  80

Tyr Leu Gly Thr Glu Gln Glu Phe Lys Glu Met Cys Ala Ala Ala Glu
                85                  90                  95

Glu Tyr Gly Ile Lys Val Ile Val Asp Ala Val Ile Asn His Thr Thr
            100                 105                 110

Ser Asp Tyr Ala Ala Ile Ser Asn Glu Val Lys Ser Ile Pro Asn Trp
        115                 120                 125

Thr His Gly Asn Thr Gln Ile Lys Asn Trp Ser Asp Arg Trp Asp Val
    130                 135                 140

Thr Gln Asn Ser Leu Leu Gly Leu Tyr Asp Trp Asn Thr Gln Asn Thr
145                 150                 155                 160

Gln Val Gln Ser Tyr Leu Lys Arg Phe Leu Asp Arg Ala Leu Asn Asp
                165                 170                 175

Gly Ala Asp Gly Phe Arg Phe Asp Ala Ala Lys His Ile Glu Leu Pro
            180                 185                 190

Asp Asp Gly Ser Tyr Gly Ser Gln Phe Trp Pro Asn Ile Thr Asn Thr
        195                 200                 205

Ser Ala Glu Phe Gln Tyr Gly Glu Ile Leu Gln Asp Ser Ala Ser Arg
    210                 215                 220

Asp Ala Ala Tyr Ala Asn Tyr Met Asp Val Thr Ala Ser Asn Tyr Gly
225                 230                 235                 240

His Ser Ile Arg Ser Ala Leu Lys Asn Arg Asn Leu Gly Val Ser Asn
                245                 250                 255

Ile Ser His Tyr Ala Ser Asp Val Ser Ala Asp Lys Leu Val Thr Trp
            260                 265                 270

Val Glu Ser His Asp Thr Tyr Ala Asn Asp Asp Glu Glu Ser Thr Trp
        275                 280                 285

Met Ser Asp Asp Asp Ile Arg Leu Gly Trp Ala Val Ile Ala Ser Arg
    290                 295                 300

Ser Gly Ser Thr Pro Leu Phe Phe Ser Arg Pro Glu Gly Gly Gly Asn
305                 310                 315                 320

Gly Val Arg Phe Pro Gly Lys Ser Gln Ile Gly Asp Arg Gly Ser Ala
                325                 330                 335

Leu Phe Glu Asp Gln Ala Ile Thr Ala Val Asn Arg Phe His Asn Val
            340                 345                 350

Met Ala Gly Gln Pro Glu Glu Leu Ser Asn Pro Asn Gly Asn Asn Gln
        355                 360                 365

Ile Phe Met Asn Gln Arg Gly Ser His Gly Val Val Leu Ala Asn Ala
    370                 375                 380

Gly Ser Ser Ser Val Ser Ile Asn Thr Ala Thr Lys Leu Pro Asp Gly
385                 390                 395                 400

Arg Tyr Asp Asn Lys Ala Gly Ala Gly Ser Phe Gln Val Asn Asp Gly
                405                 410                 415

Lys Leu Thr Gly Thr Ile Asn Ala Arg Ser Val Ala Val Leu Tyr Pro
            420                 425                 430

Asp Asp Ile Ala Lys Ala Pro His Val Phe Leu Glu Asn Tyr Lys Thr
        435                 440                 445

Gly Val Thr His Ser Phe Asn Asp Gln Leu Thr Ile Thr Leu Arg Ala
    450                 455                 460
```

```
Asp Ala Asn Thr Thr Lys Ala Val Tyr Gln Ile Asn Asn Gly Pro Asp
465                 470                 475                 480

Asp Arg Arg Leu Arg Met Glu Ile Asn Ser Gln Ser Glu Lys Glu Ile
                485                 490                 495

Gln Phe Gly Lys Thr Tyr Thr Ile Met Leu Lys Gly Thr Asn Ser Asp
            500                 505                 510

Gly Val Thr Arg Thr Glu Lys Tyr Ser Phe Val Lys Arg Asp Pro Ala
        515                 520                 525

Ser Ala Lys Thr Ile Gly Tyr Gln Asn Pro Asn His Trp Ser Gln Val
    530                 535                 540

Asn Ala Tyr Ile Tyr Lys His Asp Gly Ser Arg Val Ile Glu Leu Thr
545                 550                 555                 560

Gly Ser Trp Pro Gly Lys Pro Met Thr Lys Asn Ala Asp Gly Ile Tyr
                565                 570                 575

Thr Leu Thr Leu Pro Ala Asp Thr Asp Thr Thr Asn Ala Lys Val Ile
            580                 585                 590

Phe Asn Asn Gly Ser Ala Gln Val Pro Gly Gln Asn Gln Pro Gly Phe
        595                 600                 605

Asp Tyr Val Leu Asn Gly Leu Tyr Asn Asp Ser Gly Leu Ser Gly Ser
    610                 615                 620

Leu Pro His
625


<210> SEQ ID NO 4
<211> LENGTH: 626
<212> TYPE: PRT
<213> ORGANISM: Bacillus amyloliquefaciens

<400> SEQUENCE: 4

Glu Thr Ala Asn Lys Ser Asn Lys Val Thr Ala Ser Ser Val Lys Asn
1               5                   10                  15

Gly Thr Ile Leu His Ala Trp Asn Trp Ser Phe Asn Thr Leu Thr Gln
            20                  25                  30

Asn Met Lys Asp Ile Arg Asp Ala Gly Tyr Ala Ala Ile Gln Thr Ser
        35                  40                  45

Pro Ile Asn Gln Val Lys Glu Gly Asn Gln Gly Asp Lys Ser Met Arg
    50                  55                  60

Asn Trp Tyr Trp Leu Tyr Gln Pro Thr Ser Tyr Gln Ile Gly Asn Arg
65                  70                  75                  80

Tyr Leu Gly Thr Glu Gln Glu Phe Lys Asp Met Cys Ala Ala Ala Glu
                85                  90                  95

Lys Tyr Gly Val Lys Val Ile Val Asp Ala Val Ile Asn His Thr Thr
            100                 105                 110

Ser Asp Tyr Gly Ala Ile Ser Asp Glu Ile Lys Arg Ile Pro Asn Trp
        115                 120                 125

Thr His Gly Asn Thr Gln Ile Lys Asn Trp Ser Asp Arg Trp Asp Val
    130                 135                 140

Thr Gln Asn Ser Leu Leu Gly Leu Tyr Asp Trp Asn Thr Gln Asn Thr
145                 150                 155                 160

Glu Val Gln Val Tyr Leu Lys Arg Phe Leu Glu Arg Ala Leu Asn Asp
                165                 170                 175

Gly Ala Asp Gly Phe Arg Tyr Asp Ala Ala Lys His Ile Glu Leu Pro
            180                 185                 190

Asp Asp Gly Asn Tyr Gly Ser Gln Phe Trp Pro Asn Ile Thr Asn Thr
        195                 200                 205
```

-continued

```
Ser Ala Glu Phe Gln Tyr Gly Glu Ile Leu Gln Asp Ser Ala Ser Arg
    210                 215                 220

Asp Thr Ala Tyr Ala Asn Tyr Met Asn Val Thr Ala Ser Asn Tyr Gly
225                 230                 235                 240

His Ser Ile Arg Ser Ala Leu Lys Asn Arg Asn Leu Ser Val Ser Asn
                245                 250                 255

Ile Ser His Tyr Ala Ser Asp Val Ser Ala Asp Lys Leu Val Thr Trp
            260                 265                 270

Val Glu Ser His Asp Thr Tyr Ala Asn Asp Asp Glu Glu Ser Thr Trp
        275                 280                 285

Met Ser Asp Asp Asp Ile Arg Leu Gly Trp Ala Val Ile Gly Ser Arg
    290                 295                 300

Ser Gly Ser Thr Pro Leu Phe Phe Ser Arg Pro Glu Gly Gly Gly Asn
305                 310                 315                 320

Gly Val Arg Phe Pro Gly Lys Ser Gln Ile Gly Asp Arg Gly Ser Ala
                325                 330                 335

Leu Phe Lys Asp Gln Ala Ile Thr Ala Val Asn Thr Phe His Asn Val
            340                 345                 350

Met Ala Gly Gln Pro Glu Glu Leu Ser Asn Pro Asn Gly Asn Asn Gln
        355                 360                 365

Val Phe Met Asn Gln Arg Gly Ser Lys Gly Val Val Leu Ala Asn Ala
    370                 375                 380

Gly Ser Ser Ser Val Thr Ile Asn Thr Ser Ala Lys Leu Pro Asp Gly
385                 390                 395                 400

Arg Tyr Asp Asn Arg Ala Gly Ala Gly Ser Phe Gln Val Ala Asn Gly
                405                 410                 415

Lys Leu Thr Gly Thr Ile Asn Ala Arg Ser Ala Ala Val Leu Tyr Pro
            420                 425                 430

Asp Asp Ile Gly Asn Ala Pro His Val Phe Leu Glu Asn Tyr Gln Thr
        435                 440                 445

Gly Ala Val His Ser Phe Asn Asp Gln Leu Thr Val Thr Leu Arg Ala
    450                 455                 460

Asn Ala Lys Thr Thr Lys Ala Val Tyr Gln Ile Asn Asn Gly Gln Gln
465                 470                 475                 480

Thr Ala Phe Lys Asp Gly Asp Arg Leu Thr Ile Gly Lys Gly Asp Pro
                485                 490                 495

Ile Gly Thr Thr Tyr Asn Ile Lys Leu Thr Gly Thr Asn Gly Glu Gly
            500                 505                 510

Ala Ala Arg Thr Gln Glu Tyr Thr Phe Val Lys Lys Asp Pro Ser Gln
        515                 520                 525

Thr Asn Ile Ile Gly Tyr Gln Asn Pro Asp His Trp Gly Gln Val Asn
    530                 535                 540

Ala Tyr Ile Tyr Lys His Asp Gly Gly Arg Ala Ile Glu Leu Thr Gly
545                 550                 555                 560

Ser Trp Pro Gly Lys Ala Met Thr Lys Asn Ala Asn Gly Met Tyr Thr
                565                 570                 575

Leu Thr Leu Pro Glu Asn Thr Asp Thr Ala Asn Ala Lys Val Ile Phe
            580                 585                 590

Asn Asn Gly Ser Ala Gln Val Pro Gly Gln Asn Gln Pro Gly Phe Asp
        595                 600                 605

Tyr Val Gln Asn Gly Leu Tyr Asn Asn Ser Gly Leu Asn Gly Tyr Leu
    610                 615                 620
```

Pro His
625

<210> SEQ ID NO 5
<211> LENGTH: 1980
<212> TYPE: DNA
<213> ORGANISM: Artificial
<220> FEATURE:
<223> OTHER INFORMATION: Synthetic construct

<400> SEQUENCE: 5
atgaaaaaac cgctggggaa aattgtcgca agcaccgcac tactcatttc tgttgctttt 60
agttcatcga tcgcatcggc tgaaactgca aacaaatcga ataaggtgac cgcgtcatcg 120
gtcaaaaacg ggaccatcct ccatgcatgg aattggtcgt tcaatacgtt aacacaaaat 180
atgaaagata ttcgtgatgc gggctatgca gccattcaga cgtctccgat taaccaagta 240
aaggaaggga accaaggaga taaaagcatg aggaactggt actggctgta tcagccgaca 300
tcgtaccaaa tcggcaaccg ttacttaggc actgaacaag aatttaagga catgtgtgca 360
gccgcggaaa aatatggcgt aaaagtcatt gtcgatgcgg ttatcaatca tactaccagc 420
gattatggcg cgatttctga cgagattaag cgtattccaa actggaccca tggaaacaca 480
caaattaaaa attggtcgga tcgatgggac gtcactcaaa attcattgct tgggctgtat 540
gattggaata cacagaatac tgaggtgcag gcatatctga aacgtttctt ggaaagagca 600
ttgaatgacg gagcagacgg gttccgctat gatgccgcca agcatataga gcttccggat 660
gatgggaatt acggcagcca attttggccg aatatcacaa atacatcggc ggagttccaa 720
tacggagaaa tcctgcaaga cagcgcgtcc agagatacag cttatgcgaa ttatatgaat 780
gtgacggctt ctaactacgg gcattccatc agatccgctt taaagaaccg taatctgagt 840
gtgtcgaata tctcccatta tgcatctgac gtgtctgcgg acaagttagt cacatgggtg 900
gaatcacatg atacgtatgc caatgatgat gaagagtcca catggatgag tgatgacgat 960
attcgtttag gctgggcagt gattggttcc cgctcaggaa gcacgcctct tttcttttcc 1020
agacctgagg gcggaggaaa tggtgtaaga tttcccggaa aaagtcaaat aggagatcgc 1080
gggagcgcct tatttaaaga tcaggcgatc actgcggtca atacatttca caatgtaatg 1140
gccgggcagc ctgaggaact ctcgaatccg aatgggaaca accaaatctt tatgaatcag 1200
cgcggctcaa aaggcgttgt gctggcaaat gcgggatcgt cttctgtcac catcaatact 1260
tcagcgaaat tacctgacgg caggtatgat aatagggccg gcgccggttc atttcaagta 1320
gcgaacggca aactgacagg tacgatcaat gccagatcgg cggctgttct ttatcctgat 1380
gatattggaa atgcgcctca tgtctttctt gagaattacc aaacgggggc agtccattct 1440
ttcaatgatc agctgacggt caccctgcgt gcaaatgcga aaacaacaaa agccgtttac 1500
caaatcaata atgggcagca gacagcattt aaggatggag accgactaac gatcgggaaa 1560
ggagatccaa tcggcacgac atacaacatc aaattaaccg gaacgaacgg cgagggtgca 1620
gcgaggaccc aagaatacaa gtttgttaaa aaagacccgt cccaaaccaa catcattggc 1680
tatcaaaatc cggaccattg ggccaggta aatgcttata tttacaaaca tgatggaggc 1740
agggccatag aattaaccgg atcgtggccg gggaaagcca tgactaagaa tgcagatgga 1800
atgtacacgc tgacgctgcc tgagaatgcg gatacggcca acgccaaagt gatttttaac 1860
aatggcagcg cccaagtgcc cggacagaac cagcccggct ttgattatgt gcagaatggt 1920
ttgtataaca actccggttt aaacggttat cttccgcatc atcatcacca tcaccactaa 1980

<210> SEQ ID NO 6
<211> LENGTH: 659
<212> TYPE: PRT
<213> ORGANISM: Artificial
<220> FEATURE:
<223> OTHER INFORMATION: Synthetic construct

<400> SEQUENCE: 6

Met Lys Lys Pro Leu Gly Lys Ile Val Ala Ser Thr Ala Leu Leu Ile
1 5 10 15

Ser Val Ala Phe Ser Ser Ser Ile Ala Ser Ala Glu Thr Ala Asn Lys
20 25 30

Ser Asn Lys Val Thr Ala Ser Ser Val Lys Asn Gly Thr Ile Leu His
35 40 45

Ala Trp Asn Trp Ser Phe Asn Thr Leu Thr Gln Asn Met Lys Asp Ile
50 55 60

Arg Asp Ala Gly Tyr Ala Ala Ile Gln Thr Ser Pro Ile Asn Gln Val
65 70 75 80

Lys Glu Gly Asn Gln Gly Asp Lys Ser Met Arg Asn Trp Tyr Trp Leu
85 90 95

Tyr Gln Pro Thr Ser Tyr Gln Ile Gly Asn Arg Tyr Leu Gly Thr Glu
100 105 110

Gln Glu Phe Lys Asp Met Cys Ala Ala Ala Glu Lys Tyr Gly Val Lys
115 120 125

Val Ile Val Asp Ala Val Ile Asn His Thr Thr Ser Asp Tyr Gly Ala
130 135 140

Ile Ser Asp Glu Ile Lys Arg Ile Pro Asn Trp Thr His Gly Asn Thr
145 150 155 160

Gln Ile Lys Asn Trp Ser Asp Arg Trp Asp Val Thr Gln Asn Ser Leu
165 170 175

Leu Gly Leu Tyr Asp Trp Asn Thr Gln Asn Thr Glu Val Gln Ala Tyr
180 185 190

Leu Lys Arg Phe Leu Glu Arg Ala Leu Asn Asp Gly Ala Asp Gly Phe
195 200 205

Arg Tyr Asp Ala Ala Lys His Ile Glu Leu Pro Asp Asp Gly Asn Tyr
210 215 220

Gly Ser Gln Phe Trp Pro Asn Ile Thr Asn Thr Ser Ala Glu Phe Gln
225 230 235 240

Tyr Gly Glu Ile Leu Gln Asp Ser Ala Ser Arg Asp Thr Ala Tyr Ala
245 250 255

Asn Tyr Met Asn Val Thr Ala Ser Asn Tyr Gly His Ser Ile Arg Ser
260 265 270

Ala Leu Lys Asn Arg Asn Leu Ser Val Ser Asn Ile Ser His Tyr Ala
275 280 285

Ser Asp Val Ser Ala Asp Lys Leu Val Thr Trp Val Glu Ser His Asp
290 295 300

Thr Tyr Ala Asn Asp Asp Glu Glu Ser Thr Trp Met Ser Asp Asp Asp
305 310 315 320

Ile Arg Leu Gly Trp Ala Val Ile Gly Ser Arg Ser Gly Ser Thr Pro
325 330 335

Leu Phe Phe Ser Arg Pro Glu Gly Gly Gly Asn Gly Val Arg Phe Pro
340 345 350

Gly Lys Ser Gln Ile Gly Asp Arg Gly Ser Ala Leu Phe Lys Asp Gln
355 360 365

Ala Ile Thr Ala Val Asn Thr Phe His Asn Val Met Ala Gly Gln Pro
370 375 380

Glu Glu Leu Ser Asn Pro Asn Gly Asn Asn Gln Ile Phe Met Asn Gln
385 390 395 400

Arg Gly Ser Lys Gly Val Val Leu Ala Asn Ala Gly Ser Ser Ser Val
405 410 415

Thr Ile Asn Thr Ser Ala Lys Leu Pro Asp Gly Arg Tyr Asp Asn Arg
420 425 430

Ala Gly Ala Gly Ser Phe Gln Val Ala Asn Gly Lys Leu Thr Gly Thr
435 440 445

Ile Asn Ala Arg Ser Ala Ala Val Leu Tyr Pro Asp Asp Ile Gly Asn
450 455 460

Ala Pro His Val Phe Leu Glu Asn Tyr Gln Thr Gly Ala Val His Ser
465 470 475 480

Phe Asn Asp Gln Leu Thr Val Thr Leu Arg Ala Asn Ala Lys Thr Thr
485 490 495

Lys Ala Val Tyr Gln Ile Asn Asn Gly Gln Gln Thr Ala Phe Lys Asp
500 505 510

Gly Asp Arg Leu Thr Ile Gly Lys Gly Asp Pro Ile Gly Thr Thr Tyr
515 520 525

Asn Ile Lys Leu Thr Gly Thr Asn Gly Glu Gly Ala Ala Arg Thr Gln
530 535 540

Glu Tyr Lys Phe Val Lys Lys Asp Pro Ser Gln Thr Asn Ile Ile Gly
545 550 555 560

Tyr Gln Asn Pro Asp His Trp Gly Gln Val Asn Ala Tyr Ile Tyr Lys
565 570 575

His Asp Gly Gly Arg Ala Ile Glu Leu Thr Gly Ser Trp Pro Gly Lys
580 585 590

Ala Met Thr Lys Asn Ala Asp Gly Met Tyr Thr Leu Thr Leu Pro Glu
595 600 605

Asn Ala Asp Thr Ala Asn Ala Lys Val Ile Phe Asn Asn Gly Ser Ala
610 615 620

Gln Val Pro Gly Gln Asn Gln Pro Gly Phe Asp Tyr Val Gln Asn Gly
625 630 635 640

Leu Tyr Asn Asn Ser Gly Leu Asn Gly Tyr Leu Pro His His His His
645 650 655

His His His

<210> SEQ ID NO 7
<211> LENGTH: 556
<212> TYPE: PRT
<213> ORGANISM: Trametes cingulata

<400> SEQUENCE: 7

Gln Ser Ser Ala Ala Asp Ala Tyr Val Ala Ser Glu Ser Pro Ile Ala
1 5 10 15

Lys Ala Gly Val Leu Ala Asn Ile Gly Pro Ser Gly Ser Lys Ser Asn
20 25 30

Gly Ala Lys Ala Gly Ile Val Ile Ala Ser Pro Ser Thr Ser Asn Pro
35 40 45

Asn Tyr Leu Tyr Thr Trp Thr Arg Asp Ser Ser Leu Val Phe Lys Ala
50 55 60

Leu Ile Asp Gln Phe Thr Thr Gly Glu Asp Thr Ser Leu Arg Thr Leu
65 70 75 80

-continued

```
Ile Asp Glu Phe Thr Ser Ala Glu Ala Ile Leu Gln Gln Val Pro Asn
                85                  90                  95

Pro Ser Gly Thr Val Ser Thr Gly Gly Leu Gly Glu Pro Lys Phe Asn
            100                 105                 110

Ile Asp Glu Thr Ala Phe Thr Asp Ala Trp Gly Arg Pro Gln Arg Asp
        115                 120                 125

Gly Pro Ala Leu Arg Ala Thr Ala Ile Ile Thr Tyr Ala Asn Trp Leu
    130                 135                 140

Leu Asp Asn Lys Asn Thr Thr Tyr Val Thr Asn Thr Leu Trp Pro Ile
145                 150                 155                 160

Ile Lys Leu Asp Leu Asp Tyr Val Ala Ser Asn Trp Asn Gln Ser Thr
                165                 170                 175

Phe Asp Leu Trp Glu Glu Ile Asn Ser Ser Ser Phe Phe Thr Thr Ala
            180                 185                 190

Val Gln His Arg Ala Leu Arg Glu Gly Ala Thr Phe Ala Asn Arg Ile
        195                 200                 205

Gly Gln Thr Ser Val Val Ser Gly Tyr Thr Thr Gln Ala Asn Asn Leu
    210                 215                 220

Leu Cys Phe Leu Gln Ser Tyr Trp Asn Pro Thr Gly Gly Tyr Ile Thr
225                 230                 235                 240

Ala Asn Thr Gly Gly Gly Arg Ser Gly Lys Asp Ala Asn Thr Val Leu
                245                 250                 255

Thr Ser Ile His Thr Phe Asp Pro Ala Ala Gly Cys Asp Ala Val Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Ser Ile Asn Ser Gly Ile Ala Ser Asn
    290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

Ala Leu Ile Val Trp Asn Lys Leu Gly Ala Leu Asn Val Thr Ser Thr
            340                 345                 350

Ser Leu Pro Phe Phe Gln Gln Phe Ser Ser Gly Val Thr Val Gly Thr
        355                 360                 365

Tyr Ala Ser Ser Ser Ser Thr Phe Lys Thr Leu Thr Ser Ala Ile Lys
    370                 375                 380

Thr Phe Ala Asp Gly Phe Leu Ala Val Asn Ala Lys Tyr Thr Pro Ser
385                 390                 395                 400

Asn Gly Gly Leu Ala Glu Gln Tyr Ser Arg Ser Asn Gly Ser Pro Val
                405                 410                 415

Ser Ala Val Asp Leu Thr Trp Ser Tyr Ala Ala Ala Leu Thr Ser Phe
            420                 425                 430

Ala Ala Arg Ser Gly Lys Thr Tyr Ala Ser Trp Gly Ala Ala Gly Leu
        435                 440                 445

Thr Val Pro Thr Thr Cys Ser Gly Ser Gly Gly Ala Gly Thr Val Ala
    450                 455                 460

Val Thr Phe Asn Val Gln Ala Thr Thr Val Phe Gly Glu Asn Ile Tyr
465                 470                 475                 480

Ile Thr Gly Ser Val Pro Ala Leu Gln Asn Trp Ser Pro Asp Asn Ala
                485                 490                 495
```

```
Leu Ile Leu Ser Ala Ala Asn Tyr Pro Thr Trp Ser Ile Thr Val Asn
            500                 505                 510

Leu Pro Ala Ser Thr Thr Ile Glu Tyr Lys Tyr Ile Arg Lys Phe Asn
        515                 520                 525

Gly Ala Val Thr Trp Glu Ser Asp Pro Asn Asn Ser Ile Thr Thr Pro
    530                 535                 540

Ala Ser Gly Thr Phe Thr Gln Asn Asp Thr Trp Arg
545                 550                 555


<210> SEQ ID NO 8
<211> LENGTH: 591
<212> TYPE: PRT
<213> ORGANISM: Talaromyces emersonii

<400> SEQUENCE: 8

Ala Thr Gly Ser Leu Asp Ser Phe Leu Ala Thr Glu Thr Pro Ile Ala
1               5                   10                  15

Leu Gln Gly Val Leu Asn Asn Ile Gly Pro Asn Gly Ala Asp Val Ala
            20                  25                  30

Gly Ala Ser Ala Gly Ile Val Val Ala Ser Pro Ser Arg Ser Asp Pro
        35                  40                  45

Asn Tyr Phe Tyr Ser Trp Thr Arg Asp Ala Ala Leu Thr Ala Lys Tyr
    50                  55                  60

Leu Val Asp Ala Phe Ile Ala Gly Asn Lys Asp Leu Glu Gln Thr Ile
65                  70                  75                  80

Gln Gln Tyr Ile Ser Ala Gln Ala Lys Val Gln Thr Ile Ser Asn Pro
                85                  90                  95

Ser Gly Asp Leu Ser Thr Gly Gly Leu Gly Glu Pro Lys Phe Asn Val
            100                 105                 110

Asn Glu Thr Ala Phe Thr Gly Pro Trp Gly Arg Pro Gln Arg Asp Gly
        115                 120                 125

Pro Ala Leu Arg Ala Thr Ala Leu Ile Ala Tyr Ala Asn Tyr Leu Ile
    130                 135                 140

Asp Asn Gly Glu Ala Ser Thr Ala Asp Glu Ile Ile Trp Pro Ile Val
145                 150                 155                 160

Gln Asn Asp Leu Ser Tyr Ile Thr Gln Tyr Trp Asn Ser Ser Thr Phe
                165                 170                 175

Asp Leu Trp Glu Glu Val Glu Gly Ser Ser Phe Phe Thr Thr Ala Val
            180                 185                 190

Gln His Arg Ala Leu Val Glu Gly Asn Ala Leu Ala Thr Arg Leu Asn
        195                 200                 205

His Thr Cys Ser Asn Cys Val Ser Gln Ala Pro Gln Val Leu Cys Phe
    210                 215                 220

Leu Gln Ser Tyr Trp Thr Gly Ser Tyr Val Leu Ala Asn Phe Gly Gly
225                 230                 235                 240

Ser Gly Arg Ser Gly Lys Asp Val Asn Ser Ile Leu Gly Ser Ile His
                245                 250                 255

Thr Phe Asp Pro Ala Gly Gly Cys Asp Asp Ser Thr Phe Gln Pro Cys
            260                 265                 270

Ser Ala Arg Ala Leu Ala Asn His Lys Val Val Thr Asp Ser Phe Arg
        275                 280                 285

Ser Ile Tyr Ala Ile Asn Ser Gly Ile Ala Glu Gly Ser Ala Val Ala
    290                 295                 300
```

Val Gly Arg Tyr Pro Glu Asp Val Tyr Gln Gly Gly Asn Pro Trp Tyr
305 310 315 320

Leu Ala Thr Ala Ala Ala Ala Glu Gln Leu Tyr Asp Ala Ile Tyr Gln
325 330 335

Trp Lys Lys Ile Gly Ser Ile Ser Ile Thr Asp Val Ser Leu Pro Phe
340 345 350

Phe Gln Asp Ile Tyr Pro Ser Ala Ala Val Gly Thr Tyr Asn Ser Gly
355 360 365

Ser Thr Thr Phe Asn Asp Ile Ile Ser Ala Val Gln Thr Tyr Gly Asp
370 375 380

Gly Tyr Leu Ser Ile Val Glu Lys Tyr Thr Pro Ser Asp Gly Ser Leu
385 390 395 400

Thr Glu Gln Phe Ser Arg Thr Asp Gly Thr Pro Leu Ser Ala Ser Ala
405 410 415

Leu Thr Trp Ser Tyr Ala Ser Leu Leu Thr Ala Ser Ala Arg Arg Gln
420 425 430

Ser Val Val Pro Ala Ser Trp Gly Glu Ser Ser Ala Ser Ser Val Pro
435 440 445

Ala Val Cys Ser Ala Thr Ser Ala Thr Gly Pro Tyr Ser Thr Ala Thr
450 455 460

Asn Thr Val Trp Pro Ser Ser Gly Ser Gly Ser Ser Thr Thr Thr Ser
465 470 475 480

Ser Ala Pro Cys Thr Thr Pro Thr Ser Val Ala Val Thr Phe Asp Glu
485 490 495

Ile Val Ser Thr Ser Tyr Gly Glu Thr Ile Tyr Leu Ala Gly Ser Ile
500 505 510

Pro Glu Leu Gly Asn Trp Ser Thr Ala Ser Ala Ile Pro Leu Arg Ala
515 520 525

Asp Ala Tyr Thr Asn Ser Asn Pro Leu Trp Tyr Val Thr Val Asn Leu
530 535 540

Pro Pro Gly Thr Ser Phe Glu Tyr Lys Phe Phe Lys Asn Gln Thr Asp
545 550 555 560

Gly Thr Ile Val Trp Glu Asp Asp Pro Asn Arg Ser Tyr Thr Val Pro
565 570 575

Ala Tyr Cys Gly Gln Thr Thr Ala Ile Leu Asp Asp Ser Trp Gln
580 585 590

<210> SEQ ID NO 9
<211> LENGTH: 515
<212> TYPE: PRT
<213> ORGANISM: Bacillus stearothermophilus

<400> SEQUENCE: 9

Ala Ala Pro Phe Asn Gly Thr Met Met Gln Tyr Phe Glu Trp Tyr Leu
1 5 10 15

Pro Asp Asp Gly Thr Leu Trp Thr Lys Val Ala Asn Glu Ala Asn Asn
20 25 30

Leu Ser Ser Leu Gly Ile Thr Ala Leu Trp Leu Pro Pro Ala Tyr Lys
35 40 45

Gly Thr Ser Arg Ser Asp Val Gly Tyr Gly Val Tyr Asp Leu Tyr Asp
50 55 60

Leu Gly Glu Phe Asn Gln Lys Gly Thr Val Arg Thr Lys Tyr Gly Thr
65 70 75 80

```
Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495
```

```
Arg Pro Trp Thr Gly Glu Phe Val Arg Trp Thr Glu Pro Arg Leu Val
            500                 505                 510

Ala Trp Pro
        515


<210> SEQ ID NO 10
<211> LENGTH: 412
<212> TYPE: PRT
<213> ORGANISM: Pyrococcus furiosus

<400> SEQUENCE: 10

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
        35                  40                  45

Ile Gly Trp Val Asp Phe Val Asn Gly Arg Ser Tyr Pro Tyr Asp Asp
    50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
    130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
    210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
    290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350
```

Tyr Asp Pro Asn Gly Asn Gln Val Asp Tyr Ser Tyr Thr Ala Tyr Tyr
355 360 365

Asp Phe Glu Lys Val Gly Tyr Tyr Asn Pro Thr Asp Gly Thr Trp Thr
370 375 380

Ile Lys Val Val Ser Tyr Ser Gly Ser Ala Asn Tyr Gln Val Asp Val
385 390 395 400

Val Ser Asp Gly Ser Leu Ser Gln Pro Gly Ser Ser
405 410

<210> SEQ ID NO 11
<211> LENGTH: 595
<212> TYPE: PRT
<213> ORGANISM: Penicillium oxalicum

<400> SEQUENCE: 11

Arg Pro Asp Pro Lys Gly Gly Asn Leu Thr Pro Phe Ile His Lys Glu
1 5 10 15

Gly Glu Arg Ser Leu Gln Gly Ile Leu Asp Asn Leu Gly Gly Arg Gly
20 25 30

Lys Lys Thr Pro Gly Thr Ala Ala Gly Leu Phe Ile Ala Ser Pro Asn
35 40 45

Thr Glu Asn Pro Asn Tyr Tyr Tyr Thr Trp Thr Arg Asp Ser Ala Leu
50 55 60

Thr Ala Lys Cys Leu Ile Asp Leu Phe Glu Asp Ser Arg Ala Lys Phe
65 70 75 80

Pro Ile Asp Arg Lys Tyr Leu Glu Thr Gly Ile Arg Asp Tyr Lys Ser
85 90 95

Ser Gln Ala Ile Leu Gln Ser Val Ser Asn Pro Ser Gly Thr Leu Lys
100 105 110

Asp Gly Ser Gly Leu Gly Glu Pro Lys Phe Glu Ile Asp Leu Asn Pro
115 120 125

Phe Ser Gly Ala Trp Gly Arg Pro Gln Arg Asp Gly Pro Ala Leu Arg
130 135 140

Ala Thr Ala Met Ile Thr Tyr Ala Asn Tyr Leu Ile Ser His Gly Gln
145 150 155 160

Lys Ser Asp Val Ser Gln Val Met Trp Pro Ile Ile Ala Asn Asp Leu
165 170 175

Ala Tyr Val Gly Gln Tyr Trp Asn Asn Thr Gly Phe Asp Leu Trp Glu
180 185 190

Glu Val Asp Gly Ser Ser Phe Phe Thr Ile Ala Val Gln His Arg Ala
195 200 205

Leu Val Glu Gly Ser Gln Leu Ala Lys Lys Leu Gly Lys Ser Cys Asp
210 215 220

Ala Cys Asp Ser Gln Pro Pro Gln Ile Leu Cys Phe Leu Gln Ser Phe
225 230 235 240

Trp Asn Gly Lys Tyr Ile Thr Ser Asn Ile Asn Thr Gln Ala Ser Arg
245 250 255

Ser Gly Ile Asp Leu Asp Ser Val Leu Gly Ser Ile His Thr Phe Asp
260 265 270

Pro Glu Ala Ala Cys Asp Asp Ala Thr Phe Gln Pro Cys Ser Ala Arg
275 280 285

Ala Leu Ala Asn His Lys Val Tyr Val Asp Ser Phe Arg Ser Ile Tyr
290 295 300

Lys Ile Asn Ala Gly Leu Ala Glu Gly Ser Ala Ala Asn Val Gly Arg
305 310 315 320

Tyr Pro Glu Asp Val Tyr Gln Gly Gly Asn Pro Trp Tyr Leu Ala Thr
325 330 335

Leu Gly Ala Ser Glu Leu Leu Tyr Asp Ala Leu Tyr Gln Trp Asp Arg
340 345 350

Leu Gly Lys Leu Glu Val Ser Glu Thr Ser Leu Ser Phe Phe Lys Asp
355 360 365

Phe Asp Ala Thr Val Lys Ile Gly Ser Tyr Ser Arg Asn Ser Lys Thr
370 375 380

Tyr Lys Lys Leu Thr Gln Ser Ile Lys Ser Tyr Ala Asp Gly Phe Ile
385 390 395 400

Gln Leu Val Gln Gln Tyr Thr Pro Ser Asn Gly Ser Leu Ala Glu Gln
405 410 415

Tyr Asp Arg Asn Thr Ala Ala Pro Leu Ser Ala Asn Asp Leu Thr Trp
420 425 430

Ser Phe Ala Ser Phe Leu Thr Ala Thr Gln Arg Arg Asp Ala Val Val
435 440 445

Pro Pro Ser Trp Gly Ala Lys Ser Ala Asn Lys Val Pro Thr Thr Cys
450 455 460

Ser Ala Ser Pro Val Val Gly Thr Tyr Lys Ala Pro Thr Ala Thr Phe
465 470 475 480

Ser Ser Lys Thr Lys Cys Val Pro Ala Lys Asp Ile Val Pro Ile Thr
485 490 495

Phe Tyr Leu Ile Glu Asn Thr Tyr Tyr Gly Glu Asn Val Phe Met Ser
500 505 510

Gly Asn Ile Thr Ala Leu Gly Asn Trp Asp Ala Lys Lys Gly Phe Pro
515 520 525

Leu Thr Ala Asn Leu Tyr Thr Gln Asp Gln Asn Leu Trp Phe Ala Ser
530 535 540

Val Glu Phe Ile Pro Ala Gly Thr Pro Phe Glu Tyr Lys Tyr Tyr Lys
545 550 555 560

Val Glu Pro Asn Gly Asp Ile Thr Trp Glu Lys Gly Pro Asn Arg Val
565 570 575

Phe Val Ala Pro Thr Gly Cys Pro Val Gln Pro His Ser Asn Asp Val
580 585 590

Trp Gln Phe
595

<210> SEQ ID NO 12
<211> LENGTH: 583
<212> TYPE: PRT
<213> ORGANISM: Artificial
<220> FEATURE:
<223> OTHER INFORMATION: Synthetic construct

<400> SEQUENCE: 12

Ala Thr Ser Asp Asp Trp Lys Gly Lys Ala Ile Tyr Gln Leu Leu Thr
1 5 10 15

Asp Arg Phe Gly Arg Ala Asp Asp Ser Thr Ser Asn Cys Ser Asn Leu
20 25 30

Ser Asn Tyr Cys Gly Gly Thr Tyr Glu Gly Ile Thr Lys His Leu Asp
35 40 45

Tyr Ile Ser Gly Met Gly Phe Asp Ala Ile Trp Ile Ser Pro Ile Pro
50 55 60

```
Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
    130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
    290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
    370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Thr Ala Thr Pro
        435                 440                 445

Thr Gly Ser Gly Ser Val Thr Ser Thr Ser Lys Thr Thr Ala Thr Ala
    450                 455                 460

Ser Lys Thr Ser Thr Ser Thr Ser Ser Thr Ser Cys Thr Thr Pro Thr
465                 470                 475                 480
```

Ala Val Ala Val Thr Phe Asp Leu Thr Ala Thr Thr Thr Tyr Gly Glu
485 490 495

Asn Ile Tyr Leu Val Gly Ser Ile Ser Gln Leu Gly Asp Trp Glu Thr
500 505 510

Ser Asp Gly Ile Ala Leu Ser Ala Asp Lys Tyr Thr Ser Ser Asp Pro
515 520 525

Leu Trp Tyr Val Thr Val Thr Leu Pro Ala Gly Glu Ser Phe Glu Tyr
530 535 540

Lys Phe Ile Arg Ile Glu Ser Asp Asp Ser Val Glu Trp Glu Ser Asp
545 550 555 560

Pro Asn Arg Glu Tyr Thr Val Pro Gln Ala Cys Gly Thr Ser Thr Ala
565 570 575

Thr Val Thr Asp Thr Trp Arg
580

<210> SEQ ID NO 13
<211> LENGTH: 485
<212> TYPE: PRT
<213> ORGANISM: Cytophaga

<400> SEQUENCE: 13

Ala Ala Thr Asn Gly Thr Met Met Gln Tyr Phe Glu Trp Tyr Val Pro
1 5 10 15

Asn Asp Gly Gln Gln Trp Asn Arg Leu Arg Thr Asp Ala Pro Tyr Leu
20 25 30

Ser Ser Val Gly Ile Thr Ala Val Trp Thr Pro Pro Ala Tyr Lys Gly
35 40 45

Thr Ser Gln Ala Asp Val Gly Tyr Gly Pro Tyr Asp Leu Tyr Asp Leu
50 55 60

Gly Glu Phe Asn Gln Lys Gly Thr Val Arg Thr Lys Tyr Gly Thr Lys
65 70 75 80

Gly Glu Leu Lys Ser Ala Val Asn Thr Leu His Ser Asn Gly Ile Gln
85 90 95

Val Tyr Gly Asp Val Val Met Asn His Lys Ala Gly Ala Asp Tyr Thr
100 105 110

Glu Asn Val Thr Ala Val Glu Val Asn Pro Ser Asn Arg Asn Gln Glu
115 120 125

Thr Ser Gly Glu Tyr Asn Ile Gln Ala Trp Thr Gly Phe Asn Phe Pro
130 135 140

Gly Arg Gly Thr Thr Tyr Ser Asn Phe Lys Trp Gln Trp Phe His Phe
145 150 155 160

Asp Gly Thr Asp Trp Asp Gln Ser Arg Ser Leu Ser Arg Ile Phe Lys
165 170 175

Phe Arg Gly Thr Gly Lys Ala Trp Asp Trp Glu Val Ser Ser Glu Asn
180 185 190

Gly Asn Tyr Asp Tyr Leu Met Tyr Ala Asp Ile Asp Tyr Asp His Pro
195 200 205

Asp Val Val Asn Glu Met Lys Lys Trp Gly Val Trp Tyr Ala Asn Glu
210 215 220

Val Gly Leu Asp Gly Tyr Arg Leu Asp Ala Val Lys His Ile Lys Phe
225 230 235 240

Ser Phe Leu Lys Asp Trp Val Asp Asn Ala Arg Ala Ala Thr Gly Lys
245 250 255

Glu Met Phe Thr Val Gly Glu Tyr Trp Gln Asn Asp Leu Gly Ala Leu
260 265 270

Asn Asn Tyr Leu Ala Lys Val Asn Tyr Asn Gln Ser Leu Phe Asp Ala
275 280 285

Pro Leu His Tyr Asn Phe Tyr Ala Ala Ser Thr Gly Gly Gly Tyr Tyr
290 295 300

Asp Met Arg Asn Ile Leu Asn Asn Thr Leu Val Ala Ser Asn Pro Thr
305 310 315 320

Lys Ala Val Thr Leu Val Glu Asn His Asp Thr Gln Pro Gly Gln Ser
325 330 335

Leu Glu Ser Thr Val Gln Pro Trp Phe Lys Pro Leu Ala Tyr Ala Phe
340 345 350

Ile Leu Thr Arg Ser Gly Gly Tyr Pro Ser Val Phe Tyr Gly Asp Met
355 360 365

Tyr Gly Thr Lys Gly Thr Thr Thr Arg Glu Ile Pro Ala Leu Lys Ser
370 375 380

Lys Ile Glu Pro Leu Leu Lys Ala Arg Lys Asp Tyr Ala Tyr Gly Thr
385 390 395 400

Gln Arg Asp Tyr Ile Asp Asn Pro Asp Val Ile Gly Trp Thr Arg Glu
405 410 415

Gly Asp Ser Thr Lys Ala Lys Ser Gly Leu Ala Thr Val Ile Thr Asp
420 425 430

Gly Pro Gly Gly Ser Lys Arg Met Tyr Val Gly Thr Ser Asn Ala Gly
435 440 445

Glu Ile Trp Tyr Asp Leu Thr Gly Asn Arg Thr Asp Lys Ile Thr Ile
450 455 460

Gly Ser Asp Gly Tyr Ala Thr Phe Pro Val Asn Gly Gly Ser Val Ser
465 470 475 480

Val Trp Val Gln Gln
485

<210> SEQ ID NO 14
<211> LENGTH: 98
<212> TYPE: PRT
<213> ORGANISM: Anoxybacillus contaminans

<400> SEQUENCE: 14

Ser Gln Ile Thr Phe Thr Val Asn Asn Ala Thr Thr Val Trp Gly Gln
1 5 10 15

Asn Val Tyr Val Val Gly Asn Ile Ser Gln Leu Gly Asn Trp Asp Pro
20 25 30

Val His Ala Val Gln Met Thr Pro Ser Ser Tyr Pro Thr Trp Thr Val
35 40 45

Thr Ile Pro Leu Leu Gln Gly Gln Asn Ile Gln Phe Lys Phe Ile Lys
50 55 60

Lys Asp Ser Ala Gly Asn Val Ile Trp Glu Asp Ile Ser Asn Arg Thr
65 70 75 80

Tyr Thr Val Pro Thr Ala Ala Ser Gly Ala Tyr Thr Ala Ser Trp Asn
85 90 95

Val Pro

<210> SEQ ID NO 15
<211> LENGTH: 109
<212> TYPE: PRT
<213> ORGANISM: Aspergillus kawachii

<400> SEQUENCE: 15

```
Cys Thr Ala Thr Ser Thr Thr Leu Pro Ile Thr Phe Glu Glu Leu Val
1               5                   10                  15

Thr Thr Thr Tyr Gly Glu Glu Val Tyr Leu Ser Gly Ser Ile Ser Gln
            20                  25                  30

Leu Gly Glu Trp Asp Thr Ser Asp Ala Val Lys Leu Ser Ala Asp Asp
        35                  40                  45

Tyr Thr Ser Ser Asn Pro Glu Trp Ser Val Thr Val Ser Leu Pro Val
    50                  55                  60

Gly Thr Thr Phe Glu Tyr Lys Phe Ile Lys Val Asp Glu Gly Gly Ser
65                  70                  75                  80

Val Thr Trp Glu Ser Asp Pro Asn Arg Glu Tyr Thr Val Pro Glu Cys
                85                  90                  95

Gly Asn Gly Ser Gly Glu Thr Val Val Asp Thr Trp Arg
            100                 105
```

<210> SEQ ID NO 16
<211> LENGTH: 108
<212> TYPE: PRT
<213> ORGANISM: Aspergillus niger

<400> SEQUENCE: 16

```
Cys Thr Thr Pro Thr Ala Val Ala Val Thr Phe Asp Leu Thr Ala Thr
1               5                   10                  15

Thr Thr Tyr Gly Glu Asn Ile Tyr Leu Val Gly Ser Ile Ser Gln Leu
            20                  25                  30

Gly Asp Trp Glu Thr Ser Asp Gly Ile Ala Leu Ser Ala Asp Lys Tyr
        35                  40                  45

Thr Ser Ser Asp Pro Leu Trp Tyr Val Thr Val Thr Leu Pro Ala Gly
    50                  55                  60

Glu Ser Phe Glu Tyr Lys Phe Ile Arg Ile Glu Ser Asp Asp Ser Val
65                  70                  75                  80

Glu Trp Glu Ser Asp Pro Asn Arg Glu Tyr Thr Val Pro Gln Ala Cys
                85                  90                  95

Gly Thr Ser Thr Ala Thr Val Thr Asp Thr Trp Arg
            100                 105
```

<210> SEQ ID NO 17
<211> LENGTH: 95
<212> TYPE: PRT
<213> ORGANISM: Gloeophyllum sepiarium

<400> SEQUENCE: 17

```
Thr Val Ala Val Thr Phe Asn Val Asn Ala Glu Thr Val Trp Gly Glu
1               5                   10                  15

Asn Ile Tyr Leu Thr Gly Ser Val Asp Ala Leu Glu Asn Trp Ser Ala
            20                  25                  30

Asp Asn Ala Leu Leu Leu Ser Ser Ala Asn Tyr Pro Thr Trp Ser Ile
        35                  40                  45

Thr Val Asn Leu Pro Ala Ser Thr Ala Ile Glu Tyr Lys Tyr Ile Arg
    50                  55                  60

Lys Asn Asn Gly Ala Val Thr Trp Glu Ser Asp Pro Asn Asn Ser Ile
65                  70                  75                  80

Thr Thr Pro Ala Ser Gly Ser Thr Thr Glu Asn Asp Thr Trp Arg
                85                  90                  95
```

```
<210> SEQ ID NO 18
<211> LENGTH: 95
<212> TYPE: PRT
<213> ORGANISM: Gloeophyllum trabeum AMG

<400> SEQUENCE: 18

Thr Val Ala Val Thr Phe Asn Val Asn Ala Gln Thr Val Trp Gly Glu
1               5                   10                  15

Asn Ile Tyr Ile Thr Gly Ser Val Asp Ala Leu Ser Asn Trp Ser Pro
            20                  25                  30

Asp Asn Ala Leu Leu Leu Ser Ser Ala Asn Tyr Pro Thr Trp Ser Ile
        35                  40                  45

Thr Val Asn Leu Pro Ala Ser Thr Ala Ile Gln Tyr Lys Tyr Ile Arg
    50                  55                  60

Lys Met Asn Gly Ala Val Thr Trp Glu Ser Asp Pro Asn Asn Ser Ile
65                  70                  75                  80

Thr Thr Pro Ala Ser Gly Ser Trp Thr Glu Asn Asp Thr Trp Arg
                85                  90                  95


<210> SEQ ID NO 19
<211> LENGTH: 95
<212> TYPE: PRT
<213> ORGANISM: Trametes cingulata

<400> SEQUENCE: 19

Thr Val Ala Val Thr Phe Asn Val Gln Ala Thr Thr Val Phe Gly Glu
1               5                   10                  15

Asn Ile Tyr Ile Thr Gly Ser Val Pro Ala Leu Gln Asn Trp Ser Pro
            20                  25                  30

Asp Asn Ala Leu Ile Leu Ser Ala Ala Asn Tyr Pro Thr Trp Ser Ile
        35                  40                  45

Thr Val Asn Leu Pro Ala Ser Thr Thr Ile Glu Tyr Lys Tyr Ile Arg
    50                  55                  60

Lys Phe Asn Gly Ala Val Thr Trp Glu Ser Asp Pro Asn Asn Ser Ile
65                  70                  75                  80

Thr Thr Pro Ala Ser Gly Thr Phe Thr Gln Asn Asp Thr Trp Arg
                85                  90                  95
```

ALPHA-AMYLASE VARIANTS AND POLYNUCLEOTIDES ENCODING SAME

CROSS-REFERENCE TO RELATED APPLICATIONS

This application is a 35 U.S.C. 371 national application of international application no. PCT/US2021/017173 filed Feb. 9, 2021, which claims priority or the benefit under 35 U.S.C. 119 of U.S. provisional application No. 62/972,132, filed Feb. 10, 2020, U.S. provisional application No. 63/032,779, filed Jun. 1, 2020, and U.S. provisional application No. 63/073,968, filed Sep. 3, 2020, the contents of which are fully incorporated herein by reference.

REFERENCE TO A SEQUENCE LISTING

This application contains a Sequence Listing in computer readable form. The contents of the electronic sequence listing created on Feb. 9, 2021, named 15156-WO-PCT sequence list_ST25.txt and 66 KB in size, is hereby incorporated by reference in its entirety.

BACKGROUND OF THE INVENTION

Field of the Invention

The present invention relates to alpha-amylase variants, polynucleotides encoding the variants, methods of producing the variants, and methods of using the variants.

Description of the Related Art

Alpha-amylases (1,4-α-D-glucan glucanohydrolase, EC 3.2.1.1) constitute a group of enzymes which catalyze hydrolysis of starch and other linear and branched 1,4-glucosidic oligo- and polysaccharides.

Alpha-amylases are well known in industrial applications, e.g., in producing syrups or ethanol. One known alpha-amylase derived from *Bacillus* sp. belonging to the GH13_28 family is known to have some disadvantages for industrial applications because of poor stability at low pH, e.g., at pH below 5. There is therefore a need for improving pH stability of amylases belonging to the GH13_28 family, in order to improve the industrial applicability, e.g., in an ethanol production process from starch-containing material; either in a conventional starch to ethanol process or in a raw starch hydrolysis process.

Ethanol production from raw starch is normally performed as a one step process in which starch hydrolysis and fermentation is performed simultaneously, typically using an alpha-amylase and a glucoamylase to hydrolyze the raw starch and a yeast to ferment the glucose to produce ethanol. Process conditions are typically around 32° C. and at a pH from 4-5.

WO17/037614 (US2018265853 AA) discloses an alpha-amylase (SEQ ID NO: 6) having about 99% sequence identity to SEQ ID NO: 1 of the present disclosure.

US2019010473 discloses an alpha-amylase (SEQ ID NO: 34) having 87% sequence identity to SEQ ID NO: 1 of the present disclosure.

U.S. Pat. No. 9,090,887 BB discloses variants of an alpha-amylase (AmyE/SEQ ID NO: 2), wherein AmyE shares about 92% sequence identity with SEQ ID NO: 1 of the present disclosure.

WO17/133974 discloses an alpha-amylase (SEQ ID NO: 1) having about 97% sequence identity to SEQ ID NO: 1 of the present disclosure.

WO18/002360 discloses an alpha-amylase (SEQ ID NO: 2) having about 98% sequence identity to SEQ ID NO: 1 of the present disclosure.

The present invention provides alpha-amylase variants having improved properties compared to its parent.

SUMMARY OF THE INVENTION

The present invention relates to isolated alpha-amylase variants of a parent alpha-amylase, comprising an alteration at one or more positions corresponding to positions 196, 1, 2, 3, 4, 5, 6, 7, 8, 9, 10, 11, 12, 13, 14, 15, 16, 28, 38, 39, 43, 54, 56, 57, 64, 67, 68, 70, 71, 86, 89, 90, 94, 96, 99, 101, 103, 107, 108, 110, 113, 114, 117, 127, 134, 138, 142, 150, 151, 152, 156, 169, 171, 174, 179, 183, 193, 199, 200, 204, 205, 207, 208, 209, 212, 218, 221, 222, 224, 233, 241, 245, 259, 275, 278, 281, 282, 283, 284, 285, 308, 323, 335, 348, 359, 382, 386, 388, 392, 394, 396, 412, 414, 417, 424, 428, 457, 459, 466, 479, 489, 511, 533, 534, 542, 543, 545, 547, 549, 550, 551, 560, 566, 570, 574, 575, 576, 577, 578, 580, 581, 582, 589, 592, 599, 603, 605, 608, 614, 619, or 626 of the polypeptide of SEQ ID NO: 1, wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 1, SEQ ID NO: 2, SEQ ID NO: 3, or SEQ ID NO: 4.

The present invention also relates to isolated polynucleotides encoding the variants; nucleic acid constructs, vectors, and host cells comprising the polynucleotides; and methods of producing the variants.

The present invention also relates to a process of producing a fermentation product from starch-containing material comprising the steps of: (a) liquefying starch-containing material above the initial gelatinization temperature of said starch-containing material in the presence of an alpha amylase; (b) saccharifying the liquefied material; and (c) fermenting with a fermenting organism; wherein step (b) is carried out in the presence of at least a variant alpha-amylase of the invention, and optionally a glucoamylase.

The present invention also relates to a process of producing a syrup product from starch-containing material, comprising the step of: (a) liquefying starch-containing material at a temperature above the initial gelatinization temperature of said starch-containing material in the presence of an alpha-amylase; (b) saccharifying the liquefied material in the presence of at least a variant alpha-amylase of the invention, and optionally a glucoamylase.

In further aspects the present invention relates to a composition comprising the variant alpha-amylase, and to use of the variant alpha-amylase for production of syrup and/or a fermentation product.

Definitions

Alpha-amylase: Alpha-amylases (E.C. 3.2.1.1) are a group of enzymes which catalyze the hydrolysis of starch and other linear and branched 1,4 glucosidic oligo- and polysaccharides.

The skilled person will know how to determine alpha-amylase activity. It may be determined according to the procedure described in the Examples, e.g., by measuring residual activity after stressing the sample at pH 4.0 using a commercial alpha-amylase activity assay kit, such as kits containing G7-pNP substrate and alpha-Glucosidase, e.g., manufactured by Roche/Hitachi (cat. No.11876473) or Sigma-Aldrich (Catalog number MAK009).

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Carbohydrate Binding Module: The term "carbohydrate binding module" means a polypeptide amino acid sequence which binds preferentially to a poly- or oligosaccharide (carbohydrate), frequently—but not necessarily exclusively—to a water-insoluble (including crystalline) form thereof. A carbohydrate-binding module (CBM), is often referred to, a carbohydrate-binding domain (CBD).

CBMs derived from starch degrading enzymes are often referred to as starch-binding modules or SBMs (which may occur in certain amylolytic enzymes, such as certain glucoamylases (GA), or in enzymes such as cyclodextrin glucanotransferases, or in alpha-amylases). SBMs are often referred to as SBDs (Starch Binding Domains).

The parent alpha-amylase and the variant amylases of the invention preferably comprises a CBM, and in one embodiment the CBM comprises or consists of amino acids 527-626 of SEQ ID NO: 1.

Amino acids 439-526 of SEQ ID NO: 1 comprises or consists of a linker region.

In one embodiment the variant according to the invention comprises a heterologous CBM, i.e., a CBM which is foreign (not naturally occurring in the parent wt amylase enzyme) to the parent alpha-amylase used as the starting point for the variants of the invention. Such a heterologous CBM is preferably a CBM of Family 20 or a CBM-20 module. Alternatively, the heterologous CBM can be selected from Carbohydrate-Binding Module Family 21, 25, 26, 34, 41, or 48.

The "Carbohydrate-Binding Module of Family 20" or a CBM-20 module is in the context of this disclosure defined as a sequence of approximately 100 amino acids having at least 45% homology to the Carbohydrate-Binding Module (CBM) of the polypeptide disclosed in FIG. 1 by Joergensen et al. (1997) in Biotechnol. Lett. 19:1027-1031. The CBM comprises about 100 amino acids of the polypeptide, i.e., the subsequence from amino acid 582 to amino acid 683. The numbering of Glycoside Hydrolase Families applied in this disclosure follows the concept of Coutinho, P. M. & Henrissat, B. (1999) *CAZy—Carbohydrate-Active Enzymes server* available online or alternatively Coutinho, P. M. & Henrissat, B. 1999; The modular structure of cellulases and other carbohydrate-active enzymes: an integrated database approach. In "*Genetics, Biochemistry and Ecology of Cellulose Degradation*", K. Ohmiya, K. Hayashi, K. Sakka, Y. Kobayashi, S. Karita and T. Kimura eds., Uni Publishers Co., Tokyo, pp. 15-23 and Bourne, Y. & Henrissat, B. 2001; Glycoside hydrolases and glycosyltransferases: families and functional modules, *Current Opinion in Structural Biology* 11:593-600.

Examples of enzymes which comprise a CBM suitable for use in the context of the invention are alpha-amylases, maltogenic alpha-amylases, glucoamylases, beta-amylases, pullulanases, cellulases, xylanases, mannanases, arabinofuranosidases, acetylesterases and chitinases.

In one embodiment the CBM comprises or consists of amino acids 527-626 of SEQ ID NO: 1. This CBM belongs to Family 26 or CBM-26.

Catalytic domain: The term "catalytic domain" means the region of an enzyme containing the catalytic machinery of the enzyme. In one embodiment the catalytic domain comprises or consists of amino acids 12-438 of SEQ ID NO: 1.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has alpha-amylase activity. In one embodiment a fragment comprises or consists of amino acids 12-438 of SEQ ID NO: 1. In another embodiment a fragment comprises or consists of amino acids 1-438 of SEQ ID NO: 1.

Fusion polypeptide: The term "fusion polypeptide" is a polypeptide in which one polypeptide is fused at the N-terminus or the C-terminus of a variant of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12:2575-2583; Dawson et al., 1994, *Science* 266:776-779). A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3:568-576; Svetina et al., 2000, *J. Biotechnol.* 76:245-251; Rasmussen-Wilson et al., 1997, *Appl. Environ. Microbiol.* 63:3488-3493; Ward et al., 1995, *Biotechnology* 13:498-503; and Contreras et al., 1991, *Biotechnology* 9:378-381; Eaton et al., 1986, *Biochemistry* 25:505-512; Collins-Racie et al., 1995, *Biotechnology* 13:982-987; Carter et al., 1989, *Proteins: Structure, Function, and Genetics* 6:240-248; and Stevens, 2003, *Drug Discovery World* 4:35-48.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Hybrid polypeptide: The term "hybrid polypeptide" means a polypeptide comprising domains from two or more polypeptides, e.g., a binding module from one polypeptide and a catalytic domain from another polypeptide. The domains may be fused at the N-terminus or the C-terminus.

Hybridization: The term "hybridization" means the pairing of substantially complementary strands of nucleic acids, using standard Southern blotting procedures. Hybridization may be performed under medium, medium-high, high or very high stringency conditions. Medium stringency conditions means prehybridization and hybridization at 42° C. in 5×SSPE, 0.3% SDS, 200 micrograms/ml sheared and denatured salmon sperm DNA, and 35% formamide for 12 to 24 hours, followed by washing three times each for 15 minutes using 0.2×SSC, 0.2% SDS at 55° C. Medium-high stringency conditions means prehybridization and hybridization at 42° C. in 5×SSPE, 0.3% SDS, 200 micrograms/ml sheared and denatured salmon sperm DNA, and 35% formamide for 12 to 24 hours, followed by washing three times each for 15 minutes using 0.2×SSC, 0.2% SDS at 60° C. High stringency conditions means prehybridization and hybridization at 42° C. in 5×SSPE, 0.3% SDS, 200 micrograms/ml sheared and denatured salmon sperm DNA, and 50% formamide for 12 to 24 hours, followed by washing three times each for 15 minutes using 0.2×SSC, 0.2% SDS at 65° C. Very high stringency conditions means prehybridization and hybridization at 42° C. in 5×SSPE, 0.3% SDS, 200 micrograms/ml sheared and denatured salmon sperm DNA, and 50% formamide for 12 to 24 hours, followed by washing three times each for 15 minutes using 0.2×SSC, 0.2% SDS at 70° C.

Half-life: For a given variant of the invention, the enzyme activity (measured as residual activity of a sample after incubation at pH 4.0 at 37° C. for 18-24 hours) of the stressed sample was divided by the enzyme activity of the unstressed sample, to compute residual activity (see examples for exact procedure). From this, the half-life in hours of the enzyme candidate is computed as the negative of the incubation-time in hours divided by log2 of the residual activity.

Improvement Factor (IF): Improvement factor (IF) was calculated from the estimated half-life (T½), by dividing the estimated T½ for variants with the T½ of the wild type enzyme (SEQ ID NO: 1).

Improved property: The term "improved property" means a characteristic associated with a variant that is improved, such as increased stability, compared to the parent. Such improved properties include, but are not limited to, pH stability. Increased pH stability may be determined as % residual activity of the variants according to the invention after stressing the enzyme by incubation at low pH, e.g., pH 4.0 at 37° C. for 18-24 hours. Increased pH stability may also be determined as % residual activity of the variants according to the invention after stressing the enzyme by incubation at low pH, e.g., pH 4.0 at 32° C. for 24 hours or 96 hours. Residual activity determined for the variants of the invention may be determined as an improvement factor compared to the parent alpha-amylase of SEQ ID NO: 1.

Isolated: The term "isolated" means a polypeptide, nucleic acid, cell, or other specified material or component that is separated from at least one other material or component with which it is naturally associated as found in nature, including but not limited to, for example, other proteins, nucleic acids, cells, etc. An isolated polypeptide includes, but is not limited to, a culture broth containing the secreted polypeptide.

Mature polypeptide: The term "mature polypeptide" means a polypeptide in its mature form following N-terminal processing (e.g., removal of signal peptide). In one embodiment the mature polypeptide is amino acids 1-626 of the polypeptide disclosed as SEQ ID NO: 1.

Mature polypeptide coding sequence: The term "mature polypeptide coding sequence" means a polynucleotide that encodes a mature polypeptide having alpha-amylase activity.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences. The one or more control sequences may be heterologous or foreign to the polynucleotide encoding the variant polypeptide of the invention.

Operably linked: The term "operably linked" means a configuration in which a control sequence is placed at an appropriate position relative to the coding sequence of a polynucleotide such that the control sequence directs expression of the coding sequence.

Parent or parent alpha-amylase: The term "parent" or "parent alpha-amylase" means an alpha-amylase to which an alteration is made to produce the enzyme variants of the present invention. The parent may be a naturally occurring (wild-type) polypeptide or a variant or fragment thereof.

Purified: The term "purified" means a nucleic acid or polypeptide that is substantially free from other components as determined by analytical techniques well known in the art (e.g., a purified polypeptide or nucleic acid may form a discrete band in an electrophoretic gel, chromatographic eluate, and/or a media subjected to density gradient centrifugation). A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

Recombinant: The term "recombinant," when used in reference to a cell, nucleic acid, protein or vector, means that it has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g., a heterologous promoter in an expression vector. Recombinant proteins may differ from a native sequence by one or more amino acids and/or are fused with heterologous sequences. A vector comprising a nucleic acid encoding a polypeptide is a recombinant vector. The term "recombinant" is synonymous with "genetically modified" and "transgenic".

Sequence identity: The relatedness between two amino acid sequences or between two nucleotide sequences is described by the parameter "sequence identity".

For purposes of the present invention, the sequence identity between two amino acid sequences is determined as the output of "longest identity" using the Needleman-Wunsch algorithm (Needleman and Wunsch, 1970, *J. Mol. Biol.* 48:443-453) as implemented in the Needle program of the EMBOSS package (EMBOSS: The European Molecular Biology Open Software Suite, Rice et al., 2000, *Trends Genet.* 16:276-277), preferably version 6.6.0 or later. The parameters used are a gap open penalty of 10, a gap extension penalty of 0.5, and the EBLOSUM62 (EMBOSS version of BLOSUM62) substitution matrix. In order for the Needle program to report the longest identity, the -nobrief option must be specified in the command line. The output of Needle labeled "longest identity" is calculated as follows:

(Identical Residues×100)/(Length of Alignment−Total Number of Gaps in Alignment)

For purposes of the present invention, the sequence identity between two polynucleotide sequences is determined as the output of "longest identity" using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 6.6.0 or later. The parameters used are a gap open penalty of 10, a gap extension penalty of 0.5, and the EDNAFULL (EMBOSS version of NCBI NUC4.4) substitution matrix. In order for the Needle program to report the longest identity, the nobrief option must be specified in the command line. The output of Needle labeled "longest identity" is calculated as follows:

(Identical Deoxyribonucleotides×100)/(Length of Alignment−Total Number of Gaps in Alignment)

The sequence identity between two polynucleotide sequences can be determined using the same Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 6.6.0 or later. The parameters used are a gap open penalty of 10, a gap extension penalty of 0.5, and the EDNAFULL (EMBOSS version of NCBI NUC4.4) substitution matrix. The percent sequence identity is calculated as follows:

(Identical Deoxyribonucleotides×100)/(Length of the Alignment)

Subsequence: The term "subsequence" means a polynucleotide having one or more nucleotides absent from the 5' and/or 3' end of a mature polypeptide coding sequence; wherein the subsequence encodes a fragment having alpha-amylase activity.

Variant: The term "variant" means a polypeptide having alpha-amylase activity comprising an alteration, e.g., a substitution, an insertion, and/or a deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 99% of the alpha-amylase activity of the parent alpha-amylase. The variant alpha-amylases according to the invention has increased stability at pH 4.0 compared to a parent alpha-amylase, and wherein increased pH stability at pH 4.0 can be determined as % residual alpha-amylase activity (% RA) after incubation of the variant amylase at pH 4.0, 32° C., for 18-24 hours. The Residual activity (RA %) after stress was calculated by dividing activity of stressed samples with unstressed samples and multiplying with 100. Alpha-amylase activity may e.g., be determined using the pNP-G7 alpha-amylase activity assay as described in the examples and in the material and methods section.

In one embodiment the parent alpha-amylase is preferably selected from polypeptide of SEQ ID NO: 1.

Raw Starch Material: The term "raw starch material" means primary starch-based grains, which has not been subjected to temperatures above 57° C. for more than 10 minutes.

Raw Starch Hydrolysis (RSH): The term "raw starch hydrolysis" means the degradation of starch to polysaccharides from primary starch-based grains which has not been subjected to temperatures above 57° C. for more than 10 minutes.

Raw Starch Hydrolysis and fermentation process: The term "raw starch hydrolysis and fermentation process" means the fermentation of starch to ethanol from primary starch-based grains which has not been subjected to temperatures above 57° C. for more than 10 minutes.

Wild-type: The term "wild-type" in reference to an amino acid sequence or nucleic acid sequence means that the amino acid sequence or nucleic acid sequence is a native or naturally occurring sequence. As used herein, the term "naturally occurring" refers to anything (e.g., proteins, amino acids, or nucleic acid sequences) that is found in nature. Conversely, the term "non-naturally occurring" refers to anything that is not found in nature (e.g., recombinant nucleic acids and protein sequences produced in the laboratory or modification of the wild-type sequence).

Conventions for Designation of Variants

For purposes of the present invention, the polypeptide disclosed in SEQ ID NO: 1 is used to determine the corresponding amino acid position in another alpha-amylase. The amino acid sequence of another alpha-amylase is aligned with the polypeptide disclosed in SEQ ID NO: 1, and based on the alignment, the amino acid position number corresponding to any amino acid residue in the polypeptide disclosed in SEQ ID NO: 1 is determined using the Needleman-Wunsch algorithm (Needleman and Wunsch, 1970, *J. Mol. Biol.* 48:443-453) as implemented in the Needle program of the EMBOSS package (EMBOSS: The European Molecular Biology Open Software Suite, Rice et al., 2000, *Trends Genet.* 16:276-277), preferably version 5.0.0 or later. The parameters used are gap open penalty of 10, gap extension penalty of 0.5, and the EBLOSUM62 (EMBOSS version of BLOSUM62) substitution matrix.

In describing the variants of the present invention, the nomenclature described below is adapted for ease of reference. The accepted IUPAC single letter or three letter amino acid abbreviation is employed.

Alterations as used herein includes substitutions, deletions and insertions as described below.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine(S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly, the insertion of lysine after glycine at position 195 is designated "Gly195GlyLys" or "G195GK". An insertion of multiple amino acids is described as: Original amino acid, position, original amino acid, inserted amino acid #1, inserted amino acid #2; etc. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195<br>G | 195 195a 195b<br>G - K - A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively. Different alterations. Where different alterations can be introduced at a position, the different alterations are separated by a comma, e.g., "Arg170Tyr, Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

Variants

The present invention relates to variant alpha-amylases having increased pH stability at acidic pH, such as at pH 4.0-5.5 compared to a parent alpha-amylase. The parent alpha-amylase is in one embodiment the mature polypeptide disclosed herein as SEQ ID NO: 1. In other embodiments of the invention the parent polypeptide is selected from alpha-amylases disclosed herein as SEQ ID NO: 2, SEQ ID NO: 3, or SEQ ID NO: 4.

The present invention relates to isolated alpha-amylase variants of a parent alpha-amylase, comprising an alteration at one or more positions corresponding to positions 196, 1, 2, 3, 4, 5, 6, 7, 8, 9, 10, 11, 12, 13, 14, 15, 16, 28, 38, 39, 43, 54, 56, 57, 64, 67, 68, 70, 71, 86, 89, 90, 94, 96, 99, 101, 103, 107, 108, 110, 113, 114, 117, 127, 134, 138, 142, 150, 151, 152, 156, 169, 171, 174, 179, 183, 193, 199, 200, 204, 205, 207, 208, 209, 212, 218, 221, 222, 224, 233, 241, 245, 259, 275, 278, 281, 282, 283, 284, 285, 308, 323, 335, 348, 359, 382, 386, 388, 392, 394, 396, 412, 414, 417, 424, 428, 457, 459, 466, 479, 489, 511, 533, 534, 542, 543, 545, 547, 549, 550, 551, 560, 566, 570, 574, 575, 576, 577, 578, 580, 581, 582, 589, 592, 599, 603, 605, 608, 614, 619, or 626 of the polypeptide of SEQ ID NO: 1, wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 1, SEQ ID NO: 2, SEQ ID NO: 3, or SEQ ID NO: 4.

In a further particular embodiment the present invention relates to isolated alpha-amylase variants, comprising a substitution at one or more positions corresponding to positions 64, 96, 150, 179, 196, 199, 207, 222, 284 and 603 of the polypeptide of SEQ ID NO: 1, wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 1, SEQ ID NO: 2, SEQ ID NO: 3, or SEQ ID NO: 4.

The variant alpha-amylases according to the invention have increased pH stability at pH 4.0 compared to a parent alpha-amylase, and wherein increased pH stability at pH 4.0 can be determined as % residual alpha-amylase activity (% RA) after incubation of the variant amylase at pH 4.0, 32° C., for 18-24 hours. The Residual activity (RA %) after stress was calculated by dividing activity of stressed samples with unstressed samples and multiplying with 100. Alpha-amylase activity may e.g., be determined using the pNP-G7 alpha-amylase activity assay as described in the examples and in the material and methods section.

In particular the alterations are selected from alterations selected from the group consisting of: E1*, T2*, A3*, N4*, K5*, S6*, N7*, K8*, V9*, V9D, V9L, T10*, T10I, A11*, S12*, S12P, S13*, V14*, V14I, K15*, N16*, N16S, N28R, N28W, R38H, R38Y, D39R, A43D, A43T, A43V, K541, G56P, G56W, N57P, R64S, Y67T, Y67W, W68S, W68Y, Y70F, Q71E, Q71N, Q86R, K89R, D90E, A94D, E96H, E96K, G99N, K101R, I103Y, V107T, I108L, I108P, H110D, S113D, S113F, S113G, S113H, S113Q, S113W, S113Y, D114Q, A117T, N127D, Q134E, Q134L, Q134M, Q134N, Q134T, Q134W, W138Y, W142E, L150F, L150H, L150M, L150S, L150V, L150W, L150Y, G151F, G151S, G151W, G151Y, L152M, N156K, N156R, F169H, E171Q, L174I, D179G, D179S, Y183F, Y183I, D193S, D193DQ, D193DY, D193DQY, D193SQY, N196W, S199G, Q200W, N204D, I205Y, N207W, T208N, T208S, S209L, F212W, L218F, L218W, S221N, A222E, A222I, A222V, R224K, N233S, H241N, S245N, H259Y, S275L, S275N, T278N, T278W, T278Y, N281Q, N281S, D282P, D283*, D283A, D283P, E284Q, E285V, T308M, T308Y, R323K, S335K, S335Q, S335R, T348K, E359Y, A382T, S386D, S388W, N392R, N392W, S394K, K396S, Q412W, A414K, K417W, K417Y, A424P, A428S, Q457L, Q457R, T459M, A466V, Q479QP, L489Q, E511D, G533H, Y534H, Q542K, V543P, A545P, I547Y, K549*, K549Y, H550*, H550Y, D551*, G560P, A566P, N570H, M574MW, M574W, Y575W, T576Y, L577Y, T578Y, P580*, E581*, N582*, K589F, F592FK, V599W, N603W, P605S, D608Y, L614W, G619W, and H626* using SEQ ID NO: 1 for numbering or corresponding substitutions in another parent alpha-amylase.

In one embodiment alterations such as substitutions are selected from R64S, E96K, L150Y, L150W, L150H, L150M, L150F, D179S, N196W, S199G, N207W, A222E, A222I, A222V, E284Q and N603W using SEQ ID NO: 1 for numbering or corresponding substitutions in another parent alpha-amylase.

In case the parent alpha-amylase is different from SEQ ID NO: 1, the amino acid in a given position may be different from the amino acid present in the corresponding position in SEQ ID NO: 1. This, however, is understood to be within the scope of the present invention since the only essential feature is the amino acid in a given position after substitution.

In an embodiment, the variant has a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent alpha-amylase.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1.

In one aspect, the number of alterations in the variants of the present invention is 1-20, e.g., 1-10 and 1-5, such as 1, 2, 3, 4, 5, 6, 7, 8, 9 or 10 alterations.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 2

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 4

In another aspect, a variant comprises a substitution, at one or more positions corresponding to positions 64, 96, 150, 179, 196, 199, 207, 222, 284 and 603 of the polypeptide of SEQ ID NO: 1.

In another aspect, the variant comprises or consists of a substitution at a position corresponding to position 196. In another aspect, the amino acid at a position corresponding to position 196 is substituted with Trp. In another aspect, the variant comprises or consists of the substitution N196W of the polypeptide of SEQ ID NO: 1.

In another aspect, the variant comprises or consists of a substitution at a position corresponding to position 199. In another aspect, the amino acid at a position corresponding to position 199 is substituted with Gly. In another aspect, the variant comprises or consists of the substitution S199G of the polypeptide of SEQ ID NO: 1.

In another aspect, the variant comprises or consists of a substitution at a position corresponding to position 222. In another aspect, the amino acid at a position corresponding to position 222 is substituted with Val. In another aspect, the variant comprises or consists of the substitution A222V of the polypeptide of SEQ ID NO: 1.

In another aspect, the variant comprises or consists of a substitution at a position corresponding to position 222. In another aspect, the amino acid at a position corresponding to position 222 is substituted with Ile. In another aspect, the variant comprises or consists of the substitution A222I of the polypeptide of SEQ ID NO: 1.

In another aspect, the variant comprises or consists of a substitution at a position corresponding to position 222. In another aspect, the amino acid at a position corresponding to position 222 is substituted with Glu. In another aspect, the variant comprises or consists of the substitution A222E of the polypeptide of SEQ ID NO: 1.

In another aspect, the variant comprises or consists of a substitution at a position corresponding to position 207. In another aspect, the amino acid at a position corresponding to position 207 is substituted with Trp. In another aspect, the variant comprises or consists of the substitution N207W of the polypeptide of SEQ ID NO: 1.

In another aspect, the variant comprises or consists of a substitution at a position corresponding to position 603. In another aspect, the amino acid at a position corresponding to position 603 is substituted with Trp. In another aspect, the variant comprises or consists of the substitution N603W of the polypeptide of SEQ ID NO: 1.

In another aspect, the variant comprises or consists of a substitution at a position corresponding to position 150. In another aspect, the amino acid at a position corresponding to position 150 is substituted with Tyr. In another aspect, the variant comprises or consists of the substitution L150Y of the polypeptide of SEQ ID NO: 1.

In another aspect, the variant comprises or consists of a substitution at a position corresponding to position 150. In another aspect, the amino acid at a position corresponding to position 150 is substituted with Trp. In another aspect, the variant comprises or consists of the substitution L150W of the polypeptide of SEQ ID NO: 1.

In another aspect, the variant comprises or consists of a substitution at a position corresponding to position 150. In another aspect, the amino acid at a position corresponding to position 150 is substituted with His. In another aspect, the variant comprises or consists of the substitution L150H of the polypeptide of SEQ ID NO: 1.

In another aspect, the variant comprises or consists of a substitution at a position corresponding to position 150. In another aspect, the amino acid at a position corresponding to position 150 is substituted with Met. In another aspect, the variant comprises or consists of the substitution L150M of the polypeptide of SEQ ID NO: 1.

In another aspect, the variant comprises or consists of a substitution at a position corresponding to position 150. In another aspect, the amino acid at a position corresponding to position 150 is substituted with Phe. In another aspect, the variant comprises or consists of the substitution L150F of the polypeptide of SEQ ID NO: 1.

In another aspect, the variant comprises or consists of a substitution at a position corresponding to position 64. In another aspect, the amino acid at a position corresponding to position 64 is substituted with Ser. In another aspect, the variant comprises or consists of the substitution R64S of the polypeptide of SEQ ID NO: 1.

In another aspect, the variant comprises or consists of a substitution at a position corresponding to position 96. In another aspect, the amino acid at a position corresponding to position 96 is substituted with Lys. In another aspect, the variant comprises or consists of the substitution E96K of the polypeptide of SEQ ID NO: 1.

In another aspect, the variant comprises or consists of a substitution at a position corresponding to position 179. In another aspect, the amino acid at a position corresponding to position 179 is substituted with Ser. In another aspect, the variant comprises or consists of the substitution D179S of the polypeptide of SEQ ID NO: 1.

In another aspect, the variant comprises or consists of a substitution at a position corresponding to position 284. In another aspect, the amino acid at a position corresponding to position 284 is substituted with Gln. In another aspect, the variant comprises or consists of the substitution E284Q of the polypeptide of SEQ ID NO: 1.

In another aspect, the variant comprises or consists of one or more substitutions selected from the group consisting of R64S, E96K, L150Y, L150W, L150H, L150M, L150F, D179S, N196W, S199G, N207W, A222E, A222I, A222V, E284Q and N603W using SEQ ID NO: 1 for numbering.

In one specific embodiment the present invention relates to alpha-amylase variants, comprising a substitution at one or more positions corresponding to positions 150, 196, 199, 207, 222, and 603 of the polypeptide of SEQ ID NO: 1, comprising a substitution or a combination of substitutions selected from:

A222I;
A222V;
A222E;
S199G;
N196W;
N207W;
N603W;
L150Y;
L150W;
L150H;
L150M;
L150F;
R64S;
E96K;
D179S;
E284Q;
N207W+N603W;
N196W+N207W;
N196W+N603W;
N196W+N207W+N603W;
A222I+S199G+N196W;
A222V+S199G+N196W;
A222E+S199G+N196W;
A222V+S199G+N196W+L150Y;
L150H+S199G+A222I;
L150M+S199G+A222V;
N196W+S199G+A222V+N603W;
L150F+N196W+S199G+A222I;
L150M+N196W+S199G+A222V;
L150W+S199G+A222V;
L150H+N196W+S199G+A222V;
L150W+N196W+S199G+A222I;
L150Y+S199G+A222V;
E96K+D179S+N196W+S199G+A222V+E284Q;
R64S+E96K+N196W+S199G+A222V;

wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 1, and wherein the variant alpha-amylase has increased pH stability at pH 4.0, 32° C. or 37° C. compared to a the alpha-amylase disclosed as SEQ ID NO: 1.

In one specific embodiment the present invention relates to alpha-amylase variants, comprising a substitution at one or more positions corresponding to positions 150, 196, 199, 207, 222, and 603 of the polypeptide of SEQ ID NO: 1, comprising a substitution or a combination of substitutions selected from:

A222I;
A222V;
A222E;
S199G;
N196W;
N207W;
N603W;
L150Y;
L150W;
L150H;
L150M;
L150F;
R64S;
E96K;
D179S;
E284Q;N207W+N603W;
N196W+N207W;
N196W+N603W;
N196W+N207W+N603W;
A222I+S199G+N196W;
A222V+S199G+N196W;
A222E+S199G+N196W;
A222V+S199G+N196W+L150Y;
L150H+S199G+A222I;
L150M+S199G+A222V;
N196W+S199G+A222V+N603W;
L150F+N196W+S199G+A222I;
L150M+N196W+S199G+A222V;
L150W+S199G+A222V;
L150H+N196W+S199G+A222V;
L150W+N196W+S199G+A222I;
L150Y+S199G+A222V;
E96K+D179S+N196W+S199G+A222V+E284Q;
R64S+E96K+N196W+S199G+A222V;

wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 2, and wherein the variant alpha-amylase has increased pH stability at pH 4.0, 37° C. compared to a the alpha-amylase disclosed as SEQ ID NO: 2.

In one specific embodiment the present invention relates to alpha-amylase variants, comprising a substitution at one or more positions corresponding to positions 150, 196, 199, 207, 222, and 603 of the polypeptide of SEQ ID NO: 1, comprising a substitution or a combination of substitutions selected from:

A222I;
A222V;
A222E;
S199G;
N196W;
N207W;
N603W;
L150Y;
L150W;
L150H;
L150M;
L150F;
R64S;
E96K;
D179S;
E284Q;
N207W+N603W;
N196W+N207W;
N196W+N603W;
N196W+N207W+N603W;
A222I+S199G+N196W;
A222V+S199G+N196W;
A222E+S199G+N196W;
A222V+S199G+N196W+L150Y;
L150H+S199G+A222I;
L150M+S199G+A222V;
N196W+S199G+A222V+N603W;
L150F+N196W+S199G+A222I;
L150M+N196W+S199G+A222V;
L150W+S199G+A222V;
L150H+N196W+S199G+A222V;
L150W+N196W+S199G+A222I;
L150Y+S199G+A222V;
E96K+D179S+N196W+S199G+A222V+E284Q;
R64S+E96K+N196W+S199G+A222V;

wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 3, and wherein the variant alpha-amylase has increased pH stability at pH 4.0, 37° C. compared to a the alpha-amylase disclosed as SEQ ID NO: 3.

In one specific embodiment the present invention relates to alpha-amylase variants, comprising a substitution at one or more positions corresponding to positions 150, 196, 199, 207, 222, and 603 of the polypeptide of SEQ ID NO: 1, comprising a substitution or a combination of substitutions selected from:

A222I;
A222V;
A222E;
S199G;
N196W;
N207W;
N603W;
L150Y;
L150W;
L150H;
L150M;
L150F;
R64S;
E96K;
D179S;
E284Q;
N207W+N603W;
N196W+N207W;
N196W+N603W;
N196W+N207W+N603W;
A222I+S199G+N196W;
A222V+S199G+N196W;
A222E+S199G+N196W;
A222V+S199G+N196W+L150Y;
L150H+S199G+A222I;
L150M+S199G+A222V;
N196W+S199G+A222V+N603W;
L150F+N196W+S199G+A222I;
L150M+N196W+S199G+A222V;
L150W+S199G+A222V;
L150H+N196W+S199G+A222V;
L150W+N196W+S199G+A222I;
L150Y+S199G+A222V;
E96K+D179S+N196W+S199G+A222V+E284Q;
R64S+E96K+N196W+S199G+A222V;

wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 4, and wherein the variant alpha-amylase has increased pH stability at pH 4.0, 37° C. compared to a the alpha-amylase disclosed as SEQ ID NO: 4.

The variants of the invention have been selected based on improved pH 4 stability. More particularly the variants have increased pH stability at pH 4.0, 32° C. or 37° C., compared to a parent alpha-amylase particularly the alpha-amylase disclosed as SEQ ID NO: 1.

The increased pH stability at pH 4.0 can be determined as residual alpha-amylase activity after incubation of the variant amylase at pH 4.0, 32° C. or 37° C., for 18-24 hours and calculation of enzyme half-life in hours or % residual alpha-amylase activity. The increase in pH stability may in another embodiment be determined at pH 4.0, 32° C., for 24 hours or 96 hours. Thus, in this embodiment the variant alpha-amylase of the invention has an improved property relative to the parent, wherein the improved property is increased pH stability at pH 4.0, 32° C. compared to a parent alpha-amylase particularly the alpha-amylase disclosed as SEQ ID NO: 1. Also in this case the improved stability may be calculated as enzyme half-life in hours.

In a particular aspect the half-life is increased compared to the amylase of SEQ ID NO: 1 of at least a factor 1.2, 1.3, 1.4, 1.5, 2.0, 2.5, 3.0, 3.5, 4.0, 4.5, 5.0, 6.0, 7.0, such as at least 8.0.

It is well known in the art that possessing of the signal peptide may result in a distribution of different forms of mature polypeptides, thus in one embodiment the mature polypeptide will start from other positions than position 1 of SEQ ID NO: 1. E.g., the alpha-amylase variants of the present invention may comprise an N-terminal deletion, more particularly comprising at least amino acids 11 to 626 of SEQ ID NO: 1, at least amino acids 12 to 626 of SEQ ID NO: 1, such as at least amino acids 13 to 626 of SEQ ID NO: 1.

The variants of the invention may also comprise C-terminal deletions. E.g., in one embodiment the alpha-amylase variants of the invention comprise a C-terminal deletion, particularly H626*.

More particularly, the variant alpha-amylases, may comprise combinations of substitutions selected from:

S199G+H626*;
N196W+S199G+A222V+H626*;
N196W+H626*
N196W+N207W+H626*;
L150Y+N196W+S199G+A222V
E96K+D179S+N196W+S199G+A222V+E284Q;
R64S+E96K+N196W+S199G+A222V;

and wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 1, SEQ ID NO: 2, SEQ ID NO: 3, or SEQ ID NO: 4.

In another particular embodiment the variant alpha-amylase of the invention, comprising an alteration or a combination of alterations selected from:

N28W;
N196W;
S199G;
N196W+V599W;
N196W+H550Y+P605S;
N196W+A545P+T576Y;
N196W+K549Y+G560P;
I108P+Y183I+N196W+I205Y;
N196W+R323K;
N196W+D283P;
W138Y+N196W;
L150W;
N196W+N392W+K417W;
N196W+N392R+K417W;
N196W+K549*+H550*+D551*;
N196W+P580*+E581*+N582*;
N196W+F592FK;
N28W+N196W+N207W+S386D+N603W;
R38Y+N196W;
N196W+H259Y;
N196W+Q412W;
N196W+F212W;
N196W+V599W;
N196W+H550Y+P605S;
N196W+H550Y+K589F;
N196W+H550Y+D608Y;
N196W+M574W+L614W;
N196W+G533H+M574W+L614W;
N196W+V543P+N570H;
N196W+G533H+Y575W+L614W;
N196W+A545P+T576Y;
N196W+A566P+T578Y;
N196W+K549Y+G560P;
N196W+A566P+L577Y;
N196W+I547Y+G560P;
N196W+M574MW;
N196W+K549*+H550*+D551*+M574MW+P580*+E581*+N582*+F592FK;
N196W+L614W+G619W;
N28W+I108P+N196W+N207W+S386D+A466V+Q542K+N603W;
N28W+I108P+N196W+N207W+S386D+N603W;
N196W+D282P+D283*;
W138Y+N196W;
N28W+N196W+N207W+S386D+N603W;
N196W+S388W+A424P;
N196W+S388W+A424P+L489Q;
A117T+N196W+H550Y+D608Y;
N196W+Q457R+Y575W+L614W;
N196W+S199G;
N196W+A222V;
N196W+A222E;
N196W+A222I;
S199G+A222V;
S199G+A222E;
S199G+A222I;
N196W+S199G+A222I;
Q134L;
L150W+N156K+N196W+S199G+A222V;
L150Y+N156K+N196W+S199G+A222I;
L150W+N196W+S199G+A222I+A428S;
L150F+N156K+N196W+S199G+A222I;
L150Y+N156R+N196W+A222V;
L150M+N156R+N196W+S199G+A222I;
L150M+N156R+N196W+A222V;
L150Y+N156R+N196W+S199G+A222V;
L150M+N156K+N196W+S199G+A222V;
L150Y+N156R+N196W+A222I;
L150H+N156R+N196W+S199G+A222I;
L150H+N156K+N196W+A222V;
L150W+N156R+N196W+A222I;
L150F+N156R+N196W+A222I;
L150F+N156K+N196W+S199G+A222V;
L150H+N156K+N196W+S199G+A222V;
L150F+N156R+S199G+A222I;
L150M+N156K+N196W+A222V;
L150W+N156K+N196W+S199G+A222I;
N156K+N196W+S199G+A222V;
L150Y+N156R+S199G+A222I;
L150M+N156R+S199G+A222I;
L150W+N156K+S199G+A222V;
L150W+N156R+N196W+S199G+A222V;
L150Y+N156R+N196W;
N156K+N196W+A222V;
N156K+N196W+S199G;
N156R+S199G+A222V;
S113H+N196W+S199G+A222V;
Q71E+S113H+N196W+S199G+A222V;
N196W+S199G+A222V+D283A;
N196W+S199G+A222V+D283P;
W142E+D193SQY+N196W+S199G+A222V+R224K;
E96K+K101R+L150W+N156R+D179S+N196W+S199G+T208N+A222V;
E96K+K101R+L150Y+N156R+D179S+N196W+S199G+T208N+A222V+E284Q;
E96K+K101R+L150M+N156R+D179S+N196W+S199G+T208N+A222V+E284Q;
S113Q+Q134E+N196W+S199G+A222V;
S113D+Q134N+N196W+S199G+A222V;
S113F+N196W+S199G+A222V;
E171Q+N196W+S199G+N204D+A222V;
N196W+S199G+A222V+H241N+S245N+T278N+E284Q+E285V;
N196W+S199G+A222V+S394K+A414K+K417Y;

N196W+S199G+A222V+E359Y+S394K+K396S+A414K+K417Y;
R38H+E96K+G99N+K101R+D179S+N196W+S199G+A222V;
R38H+E96K+G99N+K101R+D179S+N196W+S199G+A222V+E284Q;
V107T+H110D+N196W+S199G+A222V;
Q134T+L150Y+N196W+S199G+A222V;
S113F+L150W+N196W+S199G+A222V;
S113F+L150Y+N196W+S199G+A222V;
E96K+K101R+N156R+D179S+N196W+S199G+T208N+A222V;
E96K+K101R+L150Y+N156R+D179S+N196W+S199G+T208N+A222V;
E96K+K101R+L150M+N156R+D179S+N196W+S199G+T208N+A222V;
E96K+K101R+N156R+D179S+N196W+S199G+T208N+A222V+E284Q;
E96K+K101R+L150W+N156R+D179S+N196W+S199G+T208N+A222V+E284Q;
N28R+Q86R+N196W+S199G+A222V;
N28R+Q86R+K89R+N196W+S199G+A222V;
G56P+N196W+S199G+S209L+A222V;
E96K+N196W+S199G+A222V;
T10I+N196W+S199G+A222V;
D39R+N196W+S199G+A222V;
R64S+N196W+S199G+A222V;
T10I+D39R+R64S+N196W+S199G+A222V;
T10I+D39R+N196W+S199G+A222V;
D39R+E96K+N196W+S199G+A222V;
R64S+D90E+E96K+N196W+S199G+A222V;
R38H+D39R+E96K+G99N+K101R+D179S+N196W+S199G+A222V;
R38H+R64S+E96K+G99N+K101R+D179S+N196W+S199G+A222V;
T10I+R38H+R64S+E96K+G99N+K101R+D179S+N196W+S199G+A222V;
T10I+R38H+R64S+D90E+E96K+G99N+K101R+D179S+N196W+S199G+A222V;
T10I+R38H+D39R+E96K+G99N+K101R+D179S+N196W+S199G+A222V;
R38H+D39R+R64S+E96K+G99N+K101R+D179S+N196W+S199G+A222V;
E96K+N196W+S199G+A222V+E284Q;
T10I+N196W+S199G+A222V+E284Q;
D39R+N196W+S199G+A222V+E284Q;
R64S+N196W+S199G+A222V+E284Q;
T10I+D39R+E96K+N196W+S199G+A222V+E284Q;
D193SQY+N196W+S199G+A222V;
Q134T+N196W+S199G+A222V;
L1741+N196W+S199G+T208N+A222V;
Y183F+N196W+S199G+T208S+A222V;
N127D+N156R+N196W+S199G+A222V;
Q134T+L150W+N196W+S199G+A222V;
N57P+N196W+S199G+A222V;
N196W+S199G+Q200W+A222V;
T10I+D39R+R64S+E96K+N196W+S199G+A222V+E284Q;
T10I+D39R+R64S+N196W+S199G+A222V+E284Q;
T10I+R64S+E96K+N196W+S199G+A222V+E284Q;
D39R+R64S+D90E+E96K+N196W+S199G+A222V+E284Q;
T10I+R64S+E96K+N196W+S199G+A222V;
T10I+D39R+N196W+S199G+A222V+E284Q;
D39R+E96K+N196W+S199G+A222V+E284Q;
D39R+R64S+N196W+S199G+A222V+E284Q;
R64S+E96K+N196W+S199G+A222V+E284Q;
D39R+R64S+N196W+S199G+A222V;
S12*+S13*+V14*+K15*+N16*+I103Y+N196W+S199G+A222V+N233S+T308Y;
S12*+S13*+V14*+K15*+N16*+A43D+I103Y+N196W+S199G+A222V+N233S+T308M;
V9L+S12P+V14I+N16S+A43T+N196W+S199G+A222V;
S12*+S13*+V14*+K15*+N16*+N196W+S199G+A222V;
N28W+N196W+S199G+A222V;
N196W+S199G+A222V+N392W+K417W;
T10I+D39R+E96K+N196W+S199G+A222V;
V9D+R38H+N196W+S199G+A222V+T348K;
S113F+L150Y+N156K+N196W+S199G+A222V;
S113Y+L150Y+N156K+N196W+S199G+A222V;
S113W+L150Y+N156K+N196W+S199G+A222V;
S113F+N156K+N196W+S199G+A222V;
S113Y+N156K+N196W+S199G+A222V;
S113W+N156K+N196W+S199G+A222V;
W138Y+L150V+N196W+S199G+A222V;
W138Y+L150V+D179G+N196W+S199G+A222V;
W138Y+L150V+N196W+S199G+L218W+A222V;
E96K+Q134L+D179S+N196W+S199G+A222V+E284Q;
E96K+Q134L+L150Y+N156R+D179S+N196W+S199G+A222V+E284Q;
E96K+L150Y+N156R+D179S+N196W+S199G+A222V+E284Q;
R38H+E96K+G99N+K101R+Q134L+D179S+N196W+S199G+S221N+A222V;
R38H+E96K+G99N+K101R+Q134L+D179S+N196W+S199G+A222V;
R38H+E96K+G99N+K101R+Q134L+L150Y+N156R+D179S+N196W+S199G+A222V;
R38H+E96K+G99N+K101R+L150Y+N156R+D179S+N196W+S199G+A222V;
L150F+N196W+S199G+A222I;
Q134L+L150F+N156R+N196W+S199G+A222I;
Q134L+L150H+N156R+N196W+S199G+A222I;
Q134L+L150M+N156K+N196W+S199G+A222I;
Q134L+L150Y+N156K+N196W+S199G+A222I+Q457L;
Q134M+L150W+N156K+N196W+S199G+A222I;
Q134W+L150W+N156K+N196W+S199G+A222I;
L150W+L152M+N156K+N196W+S199G+A222I;
S113F+L150W+N156K+N196W+S199G+A222I;
S113Y+L150W+N156K+N196W+S199G+A222I;
L150W+G151W+N156K+N196W+S199G+A222I;
L150W+G151S+N156K+N196W+S199G+A222I;
S113F+L150W+G151S+N156K+N196W+S199G+A222I;
Y67W+W68Y+L150W+N156K+N196W+S199G+A222I;
A43V+L150M+G151F+N156R+N196W+S199G+A222I;
L150M+G151Y+N156R+N196W+S199G+A222I;
L150M+G151W+N156R+N196W+S199G+A222I;
L150M+G151S+N156R+N196W+S199G+A222I+Y534H;
S113F+L150M+G151S+N156R+N196W+S199G+A222I;
Q134L+L150F+N156K+N196W+S199G+A222I;
L150W+G151F+N156K+N196W+S199G+A222I;
L150W+G151Y+N156K+N196W+S199G+A222I;
Y67W+W68Y+L150W+N156K+N196W+S199G+A222I;

G56W+N57P+Y67W+W68Y+L150W+N156K+N196W+S199G+A222I;
K54I+Y67W+W68S+S113G+N196W+S199G+A222V+A382T;
K541+Y67W+W68S+S113G+D114Q+L150V+N196W+S199G+A222V;
K54I+Y67W+W68S+S113G+W138Y+N196W+S199G+A222V;
K541+Y67W+W68S+S113G+D114Q+W138Y+L150V+N196W+S199G+A222V;
Q134L+N196W+S199G+A222V;
V107T+I108L+H110D+F169H+N196W+S199G+A222V;
N196W+S199G+A222V+N392W+K417W;
V9D+R38H+N196W+S199G+A222V+T348K;
E96H+L150Y+N156R+N196W+S199G+A222V+E284Q;
Q134L+L150Y+N196W+S199G+A222V;
L150Y+N196W+S199G+A222V;
Q134L+L150Y+N196W+S199G+A222V;
L150F+N156R+N196W+S199G+A222V;
L150H+N156R+N196W+S199G+A222V;
Q134L+L150F+N156R+N196W+S199G+A222V;
Q134L+L150H+N156R+N196W+S199G+A222V;
Q134L+L150F+N156K+N196W+S199G+A222V;
Q134L+L150H+N156K+N196W+S199G+A222V;
Q134L+L150Y+N156K+N196W+S199G+A222V;
L150Y+N156K+N196W+S199G+A222V;
Q134L+L150Y+N156K+N196W+S199G+A222V;
Q134W+L150Y+N156K+N196W+S199G+A222V;
Q134M+L150Y+N156K+N196W+S199G+A222V;
Q134M+L150Y+N156K+N196W+S199G+A222V+A466V;
L150Y+L152M+N156K+N196W+S199G+A222V;
L150S+N196W+S199G+A222V;
N196W+S199G+A222V+N281S;
Y67T+N196W+S199G+A222V;
Q71N+N196W+S199G+A222V;
Q71N+A94D+N196W+S199G+A222V;
N196W+S199G+L218F+A222V;
N196W+S199G+L218W+A222V;
N196W+S199G+A222V+T278W;
N196W+S199G+A222V+T278W+T459M;
N196W+S199G+A222V+T278Y;
N196W+S199G+A222V+S275N;
N196W+S199G+A222V+S275L;
N196W+S199G+A222V+S335Q;
N196W+S199G+A222V+S335K;
N196W+S199G+A222V+S335R;
N196W+S199G+L218W+A222V+S335K;
N196W+S199G+L218W+A222V+S335Q;
Y67W+N196W+S199G+A222V;
N196W+S199G+A222V+N281Q;
L150M+N156R+N196W+S199G+A222V;
Q134L+L150M+N156R+N196W+S199G+A222V;
Q134L+L150M+N156K+N196W+S199G+A222V;
D39R+N196W+S199G+A222V+N281Q+E284Q;
D39R+N196W+S199G+A222V+E284Q+Q479QP;
D39R+Y70F+N196W+S199G+A222V+E284Q;
N28W+D39R+N196W+S199G+A222V+E284Q;
D39R+N196W+S199G+N207W+A222V+E284Q;
E1*+T2*+A3*+N4*+K5*+S6*+N7*+K8*+D39R+N196W+S199G+N207W+A222V+E284Q;
N196W+N207W;
N196W+N207W+E284Q;
E1*+T2*+A3*+N4*+K5*+S6*+N7*+K8*+N196W+N207W+E284Q;
L150Y+N196W+S199G+A222V;
E1*+T2*+A3*+N4*+K5*+S6*+N7*+K8*+L150Y+N196W+S199G+A222V;
E96K+K101R+L150M+N156R+D179S+N196W+S199G+N207W+T208N+A222V;
E1*+T2*+A3*+N4*+K5*+S6*+N7*+K8*+E96K+K101R+L150M+N156R+D179S+N196W+S199G+T208N+A222V;
Q134L+L150H+N156R+N196W+S199G+A222I+E284Q;
E1*+T2*+A3*+N4*+K5*+S6*+N7*+K8*+Q134L+L150H+N156R+N196W+S199G+A222I;
E1*+T2*+A3*+N4*+K5*+S6*+N7*+K8*+Q134L+L150H+N156R+N196W+S199G+N207W+A222I+E284Q;
E96K+D179S+N196W+S199G+A222V+E284Q;
E1*+T2*+A3*+N4*+K5*+S6*+N7*+K8*+E96K+D179S+N196W+S199G+A222V+E284Q;
R64S+E96K+N196W+S199G+N207W+A222V;
N28W+D39R+N196W+S199G+N207W+A222V+E284Q;
D39R+N196W+S199G+A222V+E284Q;
D39R+N196W+S199G+N207W+A222V+E284Q;
E1*+T2*+A3*+N4*+K5*+S6*+N7*+K8*+D39R+N196W+S199G+A222V+E284Q;
E1*+T2*+A3*+N4*+K5*+S6*+N7*+K8*+N196W+N207W+E511D;
L150Y+N196W+S199G+N207W+A222V;
E96K+K101R+L150M+N156R+D179S+N196W+S199G+T208N+A222V;
E96K+K101R+L150M+N156R+D179S+N196W+S199G+T208N+A222V+E284Q;
E1*+T2*+A3*+N4*+K5*+S6*+N7*+K8*+E96K+K101R+L150M+N156R+D179S+N196W+S199G+N207W+T208N+A222V+E284Q;
Q134L+L150H+N156R+N196W+S199G+A222I;
N28W+E96K+D179S+N196W+S199G+A222V+E284Q;
R64S+E96K+N196W+S199G+A222V;
R64S+E96K+N196W+S199G+A222V+E284Q;
E1*+T2*+A3*+N4*+K5*+S6*+N7*+K8*+R64S+E96K+N196W+S199G+A222V;

and wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 1, SEQ ID NO: 2, SEQ ID NO: 3, or SEQ ID NO: 4, and wherein the variant has increased pH stability at pH 4.0, 32° C. compared to a parent alpha-amylase particularly the alpha-amylase disclosed as SEQ ID NO: 1, and optionally the variant further comprises the C-terminal deletion H626*.

In another particular embodiment the alpha-amylase variants of the invention comprise a combination of alterations selected from:

N28W+H626*;
S199G+H626*;
N196W+V599W+H626*;
N196W+H550Y+P605S+H626*;
N196W+A545P+T576Y+H626*;
N196W+K549Y+G560P+H626*;
1108P+Y183I+N196W+I205Y+H626*;
N196W+R323K+H626*;
N196W+D283P+H626*;
W138Y+N196W+H626*;

L150W+H626*;
N196W+N392W+K417W+H626*;
N196W+N392R+K417W+H626*;
N196W+K549*+H550*+D551*+H626*;
N196W+P580*+E581*+N582*+H626*;
N196W+F592FK+H626*;
N28W+N196W+N207W+S386D+N603W+H626*;
R38Y+N196W+H626*;
N196W+H259Y+H626*;
N196W+Q412W+H626*;
N196W+F212W+H626*;
N196W+V599W+H626*;
N196W+H550Y+P605S+H626*;
N196W+H550Y+K589F+H626*;
N196W+H550Y+D608Y+H626*;
N196W+M574W+L614W+H626*;
N196W+G533H+M574W+L614W+H626*;
N196W+V543P+N570H+H626*;
N196W+G533H+Y575W+L614W+H626*;
N196W+A545P+T576Y+H626*;
N196W+A566P+T578Y+H626*;
N196W+K549Y+G560P+H626*;
N196W+A566P+L577Y+H626*;
N196W+I547Y+G560P+H626*;
N196W+M574MW+H626*;
N196W+K549*+H550*+D551*+M574MW+P580*+E581*+N582*+F592FK+H626*;
N196W+L614W+G619W+H626*;
N28W+I108P+N196W+N207W+S386D+A466V+Q542K+N603W+H626*;
N28W+I108P+N196W+N207W+S386D+N603W+H626*;
N196W+D282P+D283*+H626*;
W138Y+N196W+H626*;
N28W+N196W+N207W+S386D+N603W+H626*;
N196W+S388W+A424P+H626*;
N196W+S388W+A424P+L489Q+H626*;
A117T+N196W+H550Y+D608Y+H626*;
N196W+Q457R+Y575W+L614W+H626*;
N196W+S199G;
N196W+A222V;
N196W+A222E;
N196W+A222I;
S199G+A222V;
S199G+A222E;
S199G+A222I;
N196W+S199G+A222I;
Q134L+H626*;
L150W+N156K+N196W+S199G+A222V;
L150Y+N156K+N196W+S199G+A222I;
L150W+N196W+S199G+A222I+A428S;
L150F+N156K+N196W+S199G+A222I;
L150Y+N156R+N196W+A222V;
L150M+N156R+N196W+S199G+A222I;
L150M+N156R+N196W+A222V;
L150Y+N156R+N196W+S199G+A222V;
L150M+N156K+N196W+S199G+A222V;
L150Y+N156R+N196W+A222I;
L150H+N156R+N196W+S199G+A222I;
L150H+N156K+N196W+A222V;
L150W+N156R+N196W+A222I;
L150F+N156R+N196W+A222I;
L150F+N156K+N196W+S199G+A222V;
L150H+N156K+N196W+S199G+A222V;
L150F+N156R+S199G+A222I;
L150M+N156K+N196W+A222V;
L150W+N156K+N196W+S199G+A222I;
N156K+N196W+S199G+A222V;
L150Y+N156R+S199G+A222I;
L150M+N156R+S199G+A222I;
L150W+N156K+S199G+A222V;
L150W+N156R+N196W+S199G+A222V;
L150Y+N156R+N196W;
N156K+N196W+A222V;
N156K+N196W+S199G;
N156R+S199G+A222V;
S113H+N196W+S199G+A222V;
Q71E+S113H+N196W+S199G+A222V;
N196W+S199G+A222V+D283A;
N196W+S199G+A222V+D283P;
W142E+D193SQY+N196W+S199G+A222V+R224K;
E96K+K101R+L150W+N156R+D179S+N196W+S199G+T208N+A222V;
E96K+K101R+L150Y+N156R+D179S+N196W+S199G+T208N+A222V+E284Q;
E96K+K101R+L150M+N156R+D179S+N196W+S199G+T208N+A222V+E284Q;
S113Q+Q134E+N196W+S199G+A222V;
S113D+Q134N+N196W+S199G+A222V;
S113F+N196W+S199G+A222V;
E171Q+N196W+S199G+N204D+A222V;
N196W+S199G+A222V+H241N+S245N+T278N+E284Q+E285V;
N196W+S199G+A222V+S394K+A414K+K417Y;
N196W+S199G+A222V+E359Y+S394K+K396S+A414K+K417Y;
R38H+E96K+G99N+K101R+D179S+N196W+S199G+A222V;
R38H+E96K+G99N+K101R+D179S+N196W+S199G+A222V+E284Q;
V107T+H110D+N196W+S199G+A222V;
Q134T+L150Y+N196W+S199G+A222V;
S113F+L150W+N196W+S199G+A222V;
S113F+L150Y+N196W+S199G+A222V;
E96K+K101R+N156R+D179S+N196W+S199G+T208N+A222V;
E96K+K101R+L150Y+N156R+D179S+N196W+S199G+T208N+A222V;
E96K+K101R+L150M+N156R+D179S+N196W+S199G+T208N+A222V;
E96K+K101R+N156R+D179S+N196W+S199G+T208N+A222V+E284Q;
E96K+K101R+L150W+N156R+D179S+N196W+S199G+T208N+A222V+E284Q;
N28R+Q86R+N196W+S199G+A222V;
N28R+Q86R+K89R+N196W+S199G+A222V;
G56P+N196W+S199G+S209L+A222V;
E96K+N196W+S199G+A222V;
T10I+N196W+S199G+A222V;
D39R+N196W+S199G+A222V;
R64S+N196W+S199G+A222V;
T10I+D39R+R64S+N196W+S199G+A222V;
T10I+D39R+N196W+S199G+A222V;
D39R+E96K+N196W+S199G+A222V;
R64S+D90E+E96K+N196W+S199G+A222V;
R38H+D39R+E96K+G99N+K101R+D179S+N196W+S199G+A222V;
R38H+R64S+E96K+G99N+K101R+D179S+N196W+S199G+A222V;
T10I+R38H+R64S+E96K+G99N+K101R+D179S+N196W+S199G+A222V;
T10I+R38H+R64S+D90E+E96K+G99N+K101R+D179S+N196W+S199G+A222V;

T10I+R38H+D39R+E96K+G99N+K101R+D179S+N196W+S199G+A222V;
R38H+D39R+R64S+E96K+G99N+K101R+D179S+N196W+S199G+A222V;
E96K+N196W+S199G+A222V+E284Q;
T10I+N196W+S199G+A222V+E284Q;
D39R+N196W+S199G+A222V+E284Q;
R64S+N196W+S199G+A222V+E284Q;
T10I+D39R+E96K+N196W+S199G+A222V+E284Q;
D193SQY+N196W+S199G+A222V;
Q134T+N196W+S199G+A222V;
L174|+N196W+S199G+T208N+A222V;
Y183F+N196W+S199G+T208S+A222V;
N127D+N156R+N196W+S199G+A222V;
Q134T+L150W+N196W+S199G+A222V;
N57P+N196W+S199G+A222V;
N196W+S199G+Q200W+A222V;
T10I+D39R+R64S+E96K+N196W+S199G+A222V+E284Q;
T10I+D39R+R64S+N196W+S199G+A222V+E284Q;
T10I+R64S+E96K+N196W+S199G+A222V+E284Q;
D39R+R64S+D90E+E96K+N196W+S199G+A222V+E284Q;
T10I+R64S+E96K+N196W+S199G+A222V;
T10I+D39R+N196W+S199G+A222V+E284Q;
D39R+E96K+N196W+S199G+A222V+E284Q;
D39R+R64S+N196W+S199G+A222V+E284Q;
R64S+E96K+N196W+S199G+A222V+E284Q;
D39R+R64S+N196W+S199G+A222V;
S12*+S13*+V14*+K15*+N16*+I103Y+N196W+S199G+A222V+N233S+T308Y;
S12*+S13*+V14*+K15*+N16*+A43D+I103Y+N196W+S199G+A222V+N233S+T308M;
V9L+S12P+V14I+N16S+A43T+N196W+S199G+A222V;
S12*+S13*+V14*+K15*+N16*+N196W+S199G+A222V;
N28W+N196W+S199G+A222V;
N196W+S199G+A222V+N392W+K417W;
T10I+D39R+E96K+N196W+S199G+A222V;
V9D+R38H+N196W+S199G+A222V+T348K;
S113F+L150Y+N156K+N196W+S199G+A222V+H626*;
S113Y+L150Y+N156K+N196W+S199G+A222V+H626*;
S113W+L150Y+N156K+N196W+S199G+A222V+H626*;
S113F+N156K+N196W+S199G+A222V+H626*;
S113Y+N156K+N196W+S199G+A222V+H626*;
S113W+N156K+N196W+S199G+A222V+H626*;
W138Y+L150V+N196W+S199G+A222V+H626*;
W138Y+L150V+D179G+N196W+S199G+A222V+H626*;
W138Y+L150V+N196W+S199G+L218W+A222V+H626*;
E96K+Q134L+D179S+N196W+S199G+A222V+E284Q+H626*;
E96K+Q134L+L150Y+N156R+D179S+N196W+S199G+A222V+E284Q+H626*;
E96K+L150Y+N156R+D179S+N196W+S199G+A222V+E284Q+H626*;
R38H+E96K+G99N+K101R+Q134L+D179S+N196W+S199G+S221N+A222V+H626*;
R38H+E96K+G99N+K101R+Q134L+D179S+N196W+S199G+A222V+H626*;
R38H+E96K+G99N+K101R+Q134L+L150Y+N156R+D179S+N196W+S199G+A222V+H626*;
R38H+E96K+G99N+K101R+L150Y+N156R+D179S+N196W+S199G+A222V+H626*;
L150F+N196W+S199G+A222I+H626*;
Q134L+L150F+N156R+N196W+S199G+A222I+H626*;
Q134L+L150H+N156R+N196W+S199G+A222I+H626*;
Q134L+L150M+N156K+N196W+S199G+A222I+H626*;
Q134L+L150Y+N156K+N196W+S199G+A222I+Q457L+H626*;
Q134M+L150W+N156K+N196W+S199G+A222I+H626*;
Q134W+L150W+N156K+N196W+S199G+A222I+H626*;
L150W+L152M+N156K+N196W+S199G+A222I+H626*;
S113F+L150W+N156K+N196W+S199G+A222I+H626*;
S113Y+L150W+N156K+N196W+S199G+A222I+H626*;
L150W+G151W+N156K+N196W+S199G+A222I+H626*;
L150W+G151S+N156K+N196W+S199G+A222I+H626*;
S113F+L150W+G151S+N156K+N196W+S199G+A222I+H626*;
Y67W+W68Y+L150W+N156K+N196W+S199G+A222I+H626*;
A43V+L150M+G151F+N156R+N196W+S199G+A222I;
L150M+G151Y+N156R+N196W+S199G+A222I;
L150M+G151W+N156R+N196W+S199G+A222I;
L150M+G151S+N156R+N196W+S199G+A222I+Y534H;
S113F+L150M+G151S+N156R+N196W+S199G+A222I;
Q134L+L150F+N156K+N196W+S199G+A222I+H626*;
L150W+G151F+N156K+N196W+S199G+A222I+H626*;
L150W+G151Y+N156K+N196W+S199G+A222I+H626*;
Y67W+W68Y+L150W+N156K+N196W+S199G+A222I;
G56W+N57P+Y67W+W68Y+L150W+N156K+N196W+S199G+A222I+H626*;
K541+Y67W+W68S+S113G+N196W+S199G+A222V+A382T+H626*;
K54I+Y67W+W68S+S113G+D114Q+L150V+N196W+S199G+A222V+H626*;
K541+Y67W+W68S+S113G+W138Y+N196W+S199G+A222V+H626*;
K541+Y67W+W68S+S113G+D114Q+W138Y+L150V+N196W+S199G+A222V+H626*;
Q134L+N196W+S199G+A222V+H626*;
V107T+I108L+H110D+F169H+N196W+S199G+A222V+H626*;
N196W+S199G+A222V+N392W+K417W+H626*;
V9D+R38H+N196W+S199G+A222V+T348K+H626*;
E96H+L150Y+N156R+N196W+S199G+A222V+E284Q+H626*;
Q134L+L150Y+N196W+S199G+A222V+H626*;
L150Y+N196W+S199G+A222V+H626*;
Q134L+L150Y+N196W+S199G+A222V+H626*;
L150F+N156R+N196W+S199G+A222V+H626*;

L150H+N156R+N196W+S199G+A222V+H626*;
Q134L+L150F+N156R+N196W+S199G+A222V+H626*;
Q134L+L150H+N156R+N196W+S199G+A222V+H626*;
Q134L+L150F+N156K+N196W+S199G+A222V+H626*;
Q134L+L150H+N156K+N196W+S199G+A222V+H626*;
Q134L+L150Y+N156K+N196W+S199G+A222V+H626*;
L150Y+N156K+N196W+S199G+A222V+H626*;
Q134L+L150Y+N156K+N196W+$199G+A222V+H626*;
Q134W+L150Y+N156K+N196W+S199G+A222V+H626*;
Q134M+L150Y+N156K+N196W+S199G+A222V+H626*;
Q134M+L150Y+N156K+N196W+S199G+A222V+A466V+H626*;
L150Y+L152M+N156K+N196W+S199G+A222V+H626*;
L150S+N196W+S199G+A222V+H626*;
N196W+S199G+A222V+N281S+H626*;
Y67T+N196W+S199G+A222V+H626*;
Q71N+N196W+S199G+A222V+H626*;
Q71N+A94D+N196W+S199G+A222V+H626*;
N196W+S199G+L218F+A222V+H626*;
N196W+S199G+L218W+A222V+H626*;
N196W+S199G+A222V+T278W+H626*;
N196W+S199G+A222V+T278W+T459M+H626*;
N196W+S199G+A222V+T278Y+H626*;
N196W+S199G+A222V+S275N+H626*;
N196W+S199G+A222V+S275L+H626*;
N196W+S199G+A222V+S335Q+H626*;
N196W+S199G+A222V+S335K+H626*;
N196W+S199G+A222V+S335R+H626*;
N196W+S199G+L218W+A222V+S335K+H626*;
N196W+S199G+L218W+A222V+S335Q+H626*;
Y67W+N196W+S199G+A222V+H626*;
N196W+S199G+A222V+N281Q+H626*;
L150M+N156R+N196W+S199G+A222V+H626*;
Q134L+L150M+N156R+N196W+S199G+A222V+H626*;
Q134L+L150M+N156K+N196W+S199G+A222V+H626*;
D39R+N196W+S199G+A222V+N281Q+E284Q;
D39R+N196W+S199G+A222V+E284Q+Q479QP;
D39R+Y70F+N196W+S199G+A222V+E284Q;
N28W+D39R+N196W+S199G+A222V+E284Q;
D39R+N196W+S199G+N207W+A222V+E284Q;
E1*+T2*+A3*+N4*+K5*+S6*+N7*+K8*+D39R+N196W+S199G+N207W+A222V+E284Q+H626*;
N196W+N207W;
N196W+N207W+E284Q;
E1*+T2*+A3*+N4*+K5*+S6*+N7*+K8*+N196W+N207W+E284Q;
L150Y+N196W+S199G+A222V+H626*;
E1*+T2*+A3*+N4*+K5*+S6*+N7*+K8*+L150Y+N196W+S199G+A222V;
E96K+K101R+L150M+N156R+D179S+N196W+S199G+N207W+T208N+A222V;
E1*+T2*+A3*+N4*+K5*+S6*+N7*+K8*+E96K+K101R+L150M+N156R+D179S+N196W+S199G+T208N+A222V;
Q134L+L150H+N156R+N196W+S199G+A222I+E284Q+H626*;
E1*+T2*+A3*+N4*+K5*+S6*+N7*+K8*+Q134L+L150H+N156R+N196W+S199G+A222I+H626*;
E1*+T2*+A3*+N4*+K5*+S6*+N7*+K8*+Q134L+L150H+N156R+N196W+S199G+N207W+A222I+E284Q;
E96K+D179S+N196W+S199G+A222V+E284Q+H626*;
E1*+T2*+A3*+N4*+K5*+S6*+N7*+K8*+E96K+D179S+N196W+S199G+A222V+E284Q;
R64S+E96K+N196W+$199G+N207W+A222V;
N28W+D39R+N196W+S199G+N207W+A222V+E284Q;
D39R+N196W+S199G+A222V+E284Q+H626*;
D39R+N196W+S199G+N207W+A222V+E284Q;
E1*+T2*+A3*+N4*+K5*+S6*+N7*+K8*+D39R+N196W+S199G+A222V+E284Q;
E1*+T2*+A3*+N4*+K5*+S6*+N7*+K8*+N196W+N207W+E511D;
L150Y+N196W+S199G+N207W+A222V;
E96K+K101R+L150M+N156R+D179S+N196W+S199G+T208N+A222V+H626*;
E96K+K101R+L150M+N156R+D179S+N196W+S199G+T208N+A222V+E284Q;
E1*+T2*+A3*+N4*+K5*+S6*+N7*+K8*+E96K+K101R+L150M+N156R+D179S+N196W+S199G+N207W+T208N+A222V+E284Q+H626*;
Q134L+L150H+N156R+N196W+S199G+A222I;
N28W+E96K+D179S+N196W+S199G+A222V+E284Q;
R64S+E96K+N196W+S199G+A222V+H626*;
R64S+E96K+N196W+S199G+A222V+E284Q;
E1*+T2*+A3*+N4*+K5*+S6*+N7*+K8*+R64S+E96K+N196W+S199G+A222V;

and wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 1, SEQ ID NO: 2, SEQ ID NO: 3, or SEQ ID NO: 4, and wherein the variant has increased pH stability at pH 4.0, 32° C. compared to a parent alpha-amylase particularly the alpha-amylase disclosed as SEQ ID NO: 1.

The variants of the invention may in a particular embodiment, further comprise a substitution corresponding to K8N. More particularly when expressing the variants in a yeast host cell.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered.

Essential amino acids in a polypeptide can be identified according to procedures known in the art, such as site-directed mutagenesis or alanine-scanning mutagenesis (Cunningham and Wells, 1989, *Science* 244:1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, *J. Biol. Chem.* 271:4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255:306-312; Smith et al., 1992, *J. Mol. Biol.* 224:899-904; Wlodaver et al., 1992, *FEBS Lett.* 309:59-64. The identity of essential amino acids can also be inferred from an alignment with a related polypeptide.

The variant polypeptide of the invention may be a hybrid polypeptide in which a region of one polypeptide is fused at the N-terminus or the C-terminus of a region of another polypeptide.

E.g., in one embodiment the catalytic domain of the variant alpha-amylases according to the invention may be fused to a Carbohydrate Binding Module (CBM) from another enzyme thus forming a hybrid alpha-amylase, wherein the catalytic core and the CBM are heterologous meaning that they do not occur in nature and that the CBM is foreign or heterologous to the catalytic domain.

Therefore, a further embodiment of the invention relates to a variant catalytic domain fragment, comprising a catalytic domain corresponding to at least amino acids amino acids 12-438 of SEQ ID NO: 1, preferably amino acids 1-438 of SEQ ID NO: 1, wherein optionally the linker and/or a carbohydrate binding module, CBM, has been replace with a heterologous CBM.

Heterologous meaning that the catalytic core and the CBM is not naturally occurring in the same polypeptide or enzyme.

In one embodiment, the CBM comprises amino acids 527-626 of SEQ ID NO: 1, and amino acids 439-526 comprises a linker region.

In a further embodiment, the heterologous CBM is selected from a CBM belonging to Family 20, 21, 25, 26, 34, 41 or 48. Preferably, the CBM is a Family 20 CBM.

In one particular embodiment the CBM is selected from the group consisting of:

i) a polypeptide of SEQ ID NO: 14, or a polypeptide having at least 65%, at least 70%, at least 75%, at least 80%, at least 85%, at least 90%, at least 95%, at least 96%, at least 97%, at least 98%, or at least 99% sequence identity to the polypeptide of SEQ ID NO: 14;

ii) a polypeptide of SEQ ID NO: 15, or a polypeptide having at least 65%, at least 70%, at least 75%, at least 80%, at least 85%, at least 90%, at least 95%, at least 96%, at least 97%, at least 98%, or at least 99% sequence identity to the polypeptide of SEQ ID NO: 15;

iii) a polypeptide of SEQ ID NO: 16, or a polypeptide having at least 65%, at least 70%, at least 75%, at least 80%, at least 85%, at least 90%, at least 95%, at least 96%, at least 97%, at least 98%, or at least 99% sequence identity to the polypeptide of SEQ ID NO: 16;

iv) a polypeptide of SEQ ID NO: 17, or a polypeptide having at least 65%, at least 70%, at least 75%, at least 80%, at least 85%, at least 90%, at least 95%, at least 96%, at least 97%, at least 98%, or at least 99% sequence identity to the polypeptide of SEQ ID NO: 17;

v) a polypeptide of SEQ ID NO: 18, or a polypeptide having at least 65%, at least 70%, at least 75%, at least 80%, at least 85%, at least 90%, at least 95%, at least 96%, at least 97%, at least 98%, or at least 99% sequence identity to the polypeptide of SEQ ID NO: 18; and vi) a polypeptide of SEQ ID NO: 19, or a polypeptide having at least 65%, at least 70%, at least 75%, at least 80%, at least 85%, at least 90%, at least 95%, at least 96%, at least 97%, at least 98%, or at least 99% sequence identity to the polypeptide of SEQ ID NO: 19.

It is well known in the art that linker regions may differ in length among different alpha-amylases and glucoamylases, and it is common that the length may vary in the range from about 1 amino acid to about 100 amino acids. Thus, in one embodiment the linker is selected to be in the range from 1-100 amino acids.

In an embodiment, the variant has increased pH stability at pH 4, 37° C., compared to the parent enzyme. In another embodiment the variant has increased pH stability at pH 4.0, 32° C., compared to the parent enzyme.

Parent Alpha-Amylases

The parent alpha-amylase may in a preferred embodiment be a polypeptide having at least 60% sequence identity to the polypeptide of SEQ ID NO: 1.

In an aspect, the parent has a sequence identity to the polypeptide of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In one aspect, the amino acid sequence of the parent differs by up to 10 amino acids, e.g., 1, 2, 3, 4, 5, 6, 7, 8, 9, or 10, from the polypeptide of SEQ ID NO: 1. In another aspect, the parent comprises or consists of the amino acid sequence of SEQ ID NO: 1. In another aspect, the parent is a fragment of the polypeptide of SEQ ID NO: 1 containing at least the catalytic domain.

The parent alpha-amylase may be a polypeptide having at least 60% sequence identity to the polypeptide of SEQ ID NO: 2.

In an aspect, the parent has a sequence identity to the polypeptide of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In one aspect, the amino acid sequence of the parent differs by up to 10 amino acids, e.g., 1, 2, 3, 4, 5, 6, 7, 8, 9, or 10, from the polypeptide of SEQ ID NO: 2. In another aspect, the parent comprises or consists of the amino acid sequence of SEQ ID NO: 2. In another aspect, the parent is a fragment of the polypeptide of SEQ ID NO: 2 containing at least the catalytic domain.

The parent alpha-amylase may be a polypeptide having at least 60% sequence identity to the polypeptide of SEQ ID NO: 3.

In an aspect, the parent has a sequence identity to the polypeptide of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In one aspect, the amino acid sequence of the parent differs by up to 10 amino acids, e.g., 1, 2, 3, 4, 5, 6, 7, 8, 9, or 10, from the polypeptide of SEQ ID NO: 3. In another aspect, the parent comprises or consists of the amino acid sequence of SEQ ID NO: 3. In another aspect, the parent is a fragment of the polypeptide of SEQ ID NO: 3 containing at least the catalytic domain.

The parent alpha-amylase may be a polypeptide having at least 60% sequence identity to the polypeptide of SEQ ID NO: 4.

In an aspect, the parent has a sequence identity to the polypeptide of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In one aspect, the amino acid sequence of the parent differs by up to 10 amino acids, e.g., 1, 2, 3, 4, 5, 6, 7, 8, 9, or 10, from the polypeptide of SEQ ID NO: 4. In another aspect, the parent comprises or consists of the amino acid sequence of SEQ ID NO: 4. In another aspect, the parent is a fragment of the polypeptide of SEQ ID NO: 4 containing at least the catalytic domain.

The parent polypeptide may be a hybrid polypeptide in which a region of one polypeptide is fused at the N-terminus or the C-terminus of a region of another polypeptide. E.g., in one embodiment the catalytic domain of the variant alpha-amylases according to the invention may be fused to a Carbohydrate Binding Module (CBM) from another enzyme thus forming a hybrid alpha-amylase, wherein the catalytic core and the CBM are heterologous meaning that they do not occur in nature and that the CBM is foreign or heterologous to the catalytic domain.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12:2575-2583; Dawson et al., 1994, *Science* 266:776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3:568-576; Svetina et al., 2000, *J. Biotechnol.* 76:245-251; Rasmussen-Wilson et al., 1997, *Appl. Environ. Microbiol.* 63:3488-3493; Ward et al., 1995, *Biotechnology* 13:498-503; and Contreras et al., 1991, *Biotechnology* 9:378-381; Eaton et al., 1986, *Biochemistry* 25:505-512; Collins-Racie et al., 1995, *Biotechnology* 13:982-987; Carter et al., 1989, *Proteins: Structure, Function, and Genetics* 6:240-248; and Stevens, 2003, *Drug Discovery World* 4:35-48.

The parent may be obtained from bacteria of the genus *Bacillus*. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* alpha-amylase.

In one particular aspect, the parent is a *Bacillus licheniformis.*

In another aspect, the parent is a *Bacillus amyloliquefaciens* alpha-amylase, e.g., the alpha-amylase of SEQ ID NO: 1.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having an increased stability at pH 4, 32° C. or 37° C., and having alpha-amylase activity, comprising: (a) introducing into a parent alpha-amylase an alteration at one or more positions corresponding to positions 196, 1, 2, 3, 4, 5, 6, 7, 8, 9, 10, 11, 12, 13, 14, 15, 16, 28, 38, 39, 43, 54, 56, 57, 64, 67, 68, 70, 71, 86, 89, 90, 94, 96, 99, 101, 103, 107, 108, 110, 113, 114, 117, 127, 134, 138, 142, 150, 151, 152, 156, 169, 171, 174, 179, 183, 193, 199, 200, 204, 205, 207, 208, 209, 212, 218, 221, 222, 224, 233, 241, 245, 259, 275, 278, 281, 282, 283, 284, 285, 308, 323, 335, 348, 359, 382, 386, 388, 392, 394, 396, 412, 414, 417, 424, 428, 457, 459, 466, 479, 489, 511, 533, 534, 542, 543, 545, 547, 549, 550, 551, 560, 566, 570, 574, 575, 576, 577, 578, 580, 581, 582, 589, 592, 599, 603, 605, 608, 614, 619, or 626 of the polypeptide of SEQ ID NO: 1 (or in another related parent alpha-amylase), wherein the variant has alpha-amylase activity; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76:4949-4955; and Barton et al., 1990, *Nucleic Acids Res.* 18:7349-4966. Site-directed mutagenesis can also be accomplished in vivo by methods known in the art. See, e.g., U.S. Patent Application Publication No. 2004/0171154; Storici et al., 2001, *Nature Biotechnol.* 19:773-776; Kren et al., 1998, *Nat. Med.* 4:285-290; and Calissano and Macino, 1996, *Fungal Genet. Newslett.* 43:15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432:1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86:2152-2156; WO 95/17413; or WO 95/22625. Other methods that can be used include error-prone PCR, phage display (e.g., Lowman et al., 1991, *Biochemistry* 30:10832-10837; U.S. Pat. No. 5,223,409; WO 92/06204) and region-directed mutagenesis (Derbyshire et al., 1986, *Gene* 46:145; Ner et al., 1988, DNA 7:127).

Mutagenesis/shuffling methods can be combined with high-throughput, automated screening methods to detect activity of cloned, mutagenized polypeptides expressed by host cells (Ness et al., 1999, *Nature Biotechnology* 17:893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide recognized by a host cell for expression of a polynucleotide encoding a variant of the present invention. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13:97-107), *E. coli* lac operon, *E. coli* trc promoter (Egon et al., 1988, *Gene* 69:301-315), *Streptomyces coelicolor* agarase gene (dagA), and prokaryotic beta-lactamase gene (Villa-Kamaroff et al., 1978, *Proc. Natl. Acad. Sci. USA* 75:3727-3731), as well as the tac promoter (DeBoer et al., 1983, *Proc. Natl. Acad. Sci. USA* 80:21-25). Further promoters are described in "Useful proteins from recombinant bacteria" in Gilbert et al., 1980, *Scientific American* 242:74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8:423-488.

The control sequence may also be a transcription terminator, which is recognized by a host cell to terminate transcription. The terminator is operably linked to the 3'-terminus of the polynucleotide encoding the variant. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rmB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177:3465-3471).

The control sequence may also be a leader, a nontranslated region of an mRNA that is important for translation by the host cell. The leader is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15:5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57:109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active variant by catalytic or autocatalytic cleavage of the propeptide from the propolypeptide. The propeptide coding sequence may be obtained from the genes for *Bacil-*

*lus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a variant and the signal peptide sequence is positioned next to the N-terminus of the propeptide sequence.

It may also be desirable to add regulatory sequences that regulate expression of the variant relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked to the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98:61-67; Cullen et al., 1987, *Nucleic Acids Res.* 15:9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168:111-115), competent cell transformation (see, e.g., Young and Spizizen, 1961, *J. Bacteriol.* 81:823-829, or Dubnau and Davidoff-Abelson, 1971, *J. Mol. Biol.* 56:209-221), electroporation (see, e.g., Shigekawa and Dower, 1988, *Biotechniques* 6:742-751), or conjugation (see, e.g., Koehler and Thorne, 1987, *J. Bacteriol.* 169:5271-5278). The introduction of DNA into an *E. coli* cell may be effected by protoplast transformation (see, e.g., Hanahan, 1983, *J. Mol. Biol.* 166:557-580) or electroporation (see, e.g., Dower et al., 1988, *Nucleic Acids Res.* 16:6127-6145). The introduction of DNA into a *Streptomyces* cell may be effected by protoplast transformation, electroporation (see, e.g., Gong et al., 2004, *Folia Microbiol.* (Praha) 49:399-405), conjugation (see, e.g., Mazodier et al., 1989, *J. Bacteriol.* 171:3583-3585), or transduction (see, e.g., Burke et al., 2001, *Proc. Natl. Acad. Sci. USA* 98:6289-6294). The introduction of DNA into a *Pseudomonas* cell may be effected by electroporation (see, e.g., Choi et al., 2006, *J. Microbiol. Methods* 64:391-397), or conjugation (see, e.g., Pinedo and Smets, 2005, *Appl. Environ. Microbiol.* 71:51-57). The introduction of DNA into a *Streptococcus* cell may be effected by natural competence (see, e.g., Perry and Kuramitsu, 1981, *Infect. Immun.* 32:1295-1297), protoplast transformation (see, e.g., Catt and Jollick, 1991, *Microbios* 68:189-207), electroporation (see, e.g., Buckley et al., 1999, *Appl. Environ. Microbiol.* 65:3800-3804), or conjugation (see, e.g., Clewell, 1981, *Microbiol. Rev.* 45:409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No.* 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81:1470-1474, and Christensen et al., 1988, *Bio/Technology* 6:1419-1422. Suitable methods for transforming *Fusarium* species are described by Malardier et al., 1989, *Gene* 78:147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153:163; and Hinnen et al., 1978, *Proc. Natl. Acad. Sci. USA* 75:1920.

Methods of Production

The present invention also relates to methods of producing a variant, comprising (a) cultivating a recombinant host cell of the present invention under conditions conducive for production of the variant; and optionally (b) recovering the variant.

The recombinant host cells are cultivated in a nutrient medium suitable for production of the variant using methods known in the art. For example, the cells may be cultivated by shake flask cultivation, or small-scale or large-scale fermentation (including continuous, batch, fed-batch, or solid state fermentations) in laboratory or industrial fermenters in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variants may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation. In one aspect, the whole fermentation broth is recovered.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Fermentation Broth Formulations or Cell Compositions

The present invention also relates to a fermentation broth formulation or a cell composition comprising a variant of the present invention. The fermentation broth product further comprises additional ingredients used in the fermentation process, such as, for example, cells (including, the host cells containing the gene encoding the variant of the present invention which are used to produce the variant of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid (s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a variant of the present invention. Preferably, the compositions are enriched in such a variant. The term "enriched" indicates that the alpha-amylase activity of the composition has been increased, e.g., with an enrichment factor of at least 1.1.

The compositions may comprise a variant of the present invention as the major enzymatic component, e.g., a mono-component composition. Alternatively, the compositions may comprise multiple enzymatic activities, such as one or more enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

In a particular embodiment, the composition comprises the variant alpha-amylase of the invention and a glucoamylase.

In another embodiment, the composition comprises the variant alpha-amylase of the invention and another alpha-amylase.

In another embodiment, the composition comprises the variant alpha-amylase of the invention, a glucoamylase, and another alpha-amylase.

In an embodiment the other alpha-amylase is of fungal or bacterial origin. In a preferred embodiment the other alpha-amylase is a fungal acid stable alpha-amylase. A fungal acid stable alpha-amylase is an alpha-amylase that has activity in the pH range of 3.0 to 7.0 and preferably in the pH range from 3.5 to 6.5, including activity at a pH of about 4.0, 4.5, 5.0, 5.5, and 6.0.

In a preferred embodiment the other alpha-amylase present and/or added in saccharification and/or fermentation is derived from a strain of the genus *Rhizomucor*, preferably a strain the *Rhizomucor pusillus*, such as one shown in SEQ ID NO: 3 in WO 2013/006756, such as a *Rhizomucor pusillus* alpha-amylase hybrid having an *Aspergillus niger* linker and starch-binding domain, such as the one shown in SEQ ID NO: 12 herein, or a variant thereof.

In an embodiment the other alpha-amylase is selected from the group consisting of:

(i) an alpha-amylase comprising the polypeptide of SEQ ID NO: 12 herein;

(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 12 herein.

In a preferred embodiment the other alpha-amylase is a variant of the alpha-amylase shown in SEQ ID NO: 12 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 12 for numbering).

In an embodiment the alpha-amylase is derived from a *Rhizomucor pusillus* with an *Aspergillus niger* glucoamylase linker and starch-binding domain (SBD), preferably disclosed as SEQ ID NO: 12 herein, preferably having one or more of the following substitutions: G128D, D143N, preferably G128D+D143N (using SEQ ID NO: 12 for numbering).

In an embodiment the other alpha-amylase variant present and/or added in saccharification and/or fermentation has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 12 herein.

In an embodiment, the glucoamylase comprised in the composition is of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *T. emersonii* or a strain of *Trametes*, preferably *T. cingulata*, or a strain of *Pycnoporus*, preferable *P. sanguineus*, or a strain of *Gloeophyllum*, such as *G. serpiarium* or *G. trabeum*, or a strain of the Nigrofomes.

In an embodiment the glucoamylase is derived from *Trametes*, such as a strain of *Trametes cingulata*, such as the one shown in SEQ ID NO: 7 herein.

In an embodiment the glucoamylase is selected from the group consisting of:

(i) a glucoamylase comprising the polypeptide of SEQ ID NO: 7 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 7 herein.

In an embodiment the glucoamylase is derived from *Talaromyces*, such as a strain of *Talaromyces emersonii*, such as the one shown in SEQ ID NO: 8 herein.

In an embodiment the glucoamylase is selected from the group consisting of:

(i) a glucoamylase comprising the polypeptide of SEQ ID NO: 8 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 8 herein.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL and AMG™ E (from Novozymes A/S); OPTIDEX™ 300, GC480, GC417 (from DuPont); AMIGASE™ and AMIGASE™ PLUS (from DSM); G-ZYME™ G900, G-ZYME™ and G990 ZR (from DuPont).

In addition to a glucoamylase the composition may further comprise a protease. In particular an endoprotease of family S53, more particular an S53 protease derived from *Meripilus giganteus*.

In a preferred embodiment, the ratio between glucoamylase and alpha-amylase present and/or added during saccharification and/or fermentation may preferably be in the range from 500:1 to 1:1, such as from 250:1 to 1:1, such as from 100:1 to 1:1, such as from 100:2 to 100:50, such as from 100:3 to 100:70.

The compositions may be prepared in accordance with methods known in the art and may be in the form of a liquid or a dry composition. For instance, the composition may be in the form of granulate or microgranulate. The variant may be stabilized in accordance with methods known in the art.

The compositions may be prepared in accordance with methods known in the art and may be in the form of a liquid or a dry composition. The compositions may be stabilized in accordance with methods known in the art.

The enzyme composition of the present invention may be in any form suitable for use, such as, for example, a crude fermentation broth with or without cells removed, a cell lysate with or without cellular debris, a semi-purified or purified enzyme composition, or a host cell, as a source of the enzymes.

The enzyme composition may be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

Examples are given below of preferred uses of the compositions of the present invention. The dosage of the composition and other conditions under which the composition is used may be determined on the basis of methods known in the art.

Methods of Using the Alpha-Amylase of the Invention-Industrial Applications

The variant alpha-amylases of the present invention possess valuable properties allowing for a variety of industrial applications. In particular, the alpha-amylases may be used in ethanol production, and starch conversion processes.

Further, the alpha-amylases of the invention are particularly useful in the production of sweeteners/syrups and ethanol (see, e.g., U.S. Pat. No. 5,231,017), such as fuel, drinking and industrial ethanol, from starch or whole grains.

In one embodiment, the present invention relates to a use of the alpha-amylase according to the invention in a saccharification process, particularly a simultaneous saccharification and fermentation process.

Starch Processing

Native starch consists of microscopic granules, which are insoluble in water at room temperature. When aqueous starch slurry is heated, the granules swell and eventually burst, dispersing the starch molecules into the solution. At temperatures up to about 50° C. to 75° C. the swelling may be reversible. However, with higher temperatures an irreversible swelling called "gelatinization" begins. During this "gelatinization" process there is a dramatic increase in viscosity. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. In dry milling whole kernels are milled and used. Wet milling gives a good separation of germ and meal (starch granules and protein) and is often applied at locations where the starch hydrolyzate is used in the production of, e.g., syrups. Both dry and wet milling is well known in the art of starch processing and may be used in a process of the invention. Methods for reducing the particle size of the starch containing material are well known to those skilled in the art.

As the solids level is 30-40% in a typical industrial process, the starch has to be thinned or "liquefied" so that it can be suitably processed. This reduction in viscosity is primarily attained by enzymatic degradation in current commercial practice.

Liquefaction is carried out in the presence of an alpha-amylase, preferably a bacterial alpha-amylase and/or acid fungal alpha-amylase. In an embodiment, a phytase is also present during liquefaction. In an embodiment, viscosity reducing enzymes such as a xylanase and/or beta-glucanase is also present during liquefaction.

During liquefaction, the long-chained starch is degraded into branched and linear shorter units (maltodextrins) by an alpha-amylase. Liquefaction may be carried out as a three-step hot slurry process. The slurry is heated to between 60-95° C. (e.g., 70-90° C., such as 77-86° C., 80-85° C., 83-85° C.) and an alpha-amylase is added to initiate liquefaction (thinning).

The slurry may in an embodiment be jet-cooked at between 95-140° C., e.g., 105-125° C., for about 1-15 minutes, e.g., about 3-10 minutes, especially around 5 minutes. The slurry is then cooled to 60-95° C. and more alpha-amylase is added to obtain final hydrolysis (secondary liquefaction). The jet-cooking process is carried out at pH 4.5-6.5, typically at a pH between 5 and 6. The alpha-amylase may be added as a single dose, e.g., before jet cooking, or be partly dosed before jet cooking and partly dosed after.

The liquefaction process is carried out at between 70-95° C., such as 80-90° C., such as around 85° C., for about 10 minutes to 5 hours, typically for 1-2 hours. The pH is between 4 and 7, such as between 5.5 and 6.2. In order to ensure optimal enzyme stability under these conditions, calcium may optionally be added (to provide 1-60 ppm free calcium ions, such as about 40 ppm free calcium ions). After such treatment, the liquefied starch will typically have a "dextrose equivalent" (DE) of 10-16.

Generally, liquefaction and liquefaction conditions are well known in the art.

Alpha-amylases for use in liquefaction are preferably bacterial acid stable alpha-amylases. Particularly the alpha-amylase is from a Cytophaga sp., *Exiguobacterium* sp. or a *Bacillus* sp. such as e.g., *Bacillus stearothermophilus* or *Bacillus licheniformis*.

In an embodiment the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 9 herein.

In an embodiment the *Bacillus stearothermophilus* alpha-amylase has a double deletion of two amino acids in the region from position 179 to 182, more particularly a double deletion at positions I181+G182, R179+G180, G180+I181, R179+I181, or G180+G182, preferably I181+G182, and optionally a N193F substitution, (using SEQ ID NO: 9 for numbering).

In an embodiment the *Bacillus stearothermophilus* alpha-amylase has a substitution at position S242, preferably S242Q substitution.

In an embodiment the *Bacillus stearothermophilus* alpha-amylase has a substitution at position E188, preferably E188P substitution.

In an embodiment the alpha-amylase is selected from the group of *Bacillus stearothermophilus* alpha-amylase variants with the following mutations:

I181*+G182*+N193F+E129V+K177L+R179E;

I181*+G182*+N193F+V59A+Q89R+E129V+K177L+R179E+H208Y+K220P+N224L+Q254S;

I181*+G182*+N193F+V59A Q89R+E129V+K177L+R179E+Q254S+M284V;

I181*+G182*+N193F+E129V+K177L+R179E+K220P+N224L+S242Q+Q254S; and

V59A+E129V+K177L+R179S+I181*+G182*+A184Q+E188P+T191N+N193F+V212T+S242Y+Q254S+Y268G+K279I+M284V+N293Y+T297N; (using SEQ ID NO: 9 for numbering).

In an embodiment the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 9.

In another embodiment the alpha-amylase is selected from the group of *Bacillus stearothermophilus* alpha-amylase variants with the following mutations:

N126Y F153W R178*G179*T180H E187P I203Y S362A R377Y;

N126Y F153W R178*G179*T180H E187P I203Y Y303A S362A R377Y; and

N126Y F153W R178*G179*T180H I203Y S241Q; (using SEQ ID NO: 13 for numbering), and wherein the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 9 or the polypeptide of SEQ ID NO: 13.

It should be understood that when referring to *Bacillus stearothermophilus* alpha-amylase and variants thereof they are normally produced in truncated form. In particular, the truncation may be so that the *Bacillus stearothermophilus* alpha-amylase shown in SEQ ID NO: 3 in WO 99/19467 or SEQ ID NO: 9 herein, or variants thereof, are truncated in the C-terminal preferably to have around 490 amino acids, such as from 482-493 amino acids. Preferably the *Bacillus stearothermophilus* variant alpha-amylase is truncated, preferably after position 484 of SEQ ID NO: 9, particularly after position 485, particularly after position 486, particularly after position 487, particularly after position 488, particularly after position 489, particularly after position 490, particularly after position 491, particularly after position 492, more particularly after position 493.

Saccharification may be carried out using conditions well-known in the art with a carbohydrate-source generating enzyme, in particular an alpha-amylase according to the present invention and a glucoamylase. For instance, a full saccharification step may last from about 24 to about 72 hours. However, it is common to do a pre-saccharification of typically 40-90 minutes at a temperature between 30-65° C., typically about 60° C., followed by complete saccharification during fermentation in a simultaneous saccharification and fermentation (SSF) process. Saccharification is typically carried out at a temperature in the range of 20-75° C., e.g., 25-65° C. and 40-70° C., typically around 60° C., and at a pH between about 4 and 5, normally at about pH 4.5.

The saccharification and fermentation steps may be carried out either sequentially or simultaneously. In an embodiment, saccharification and fermentation are performed simultaneously (referred to as "SSF"). However, it is common to perform a pre-saccharification step for about 30 minutes to 2 hours (e.g., 30 to 90 minutes) at a temperature of 30 to 65° C., typically around 60° C. which is followed by a complete saccharification during fermentation referred to as simultaneous saccharification and fermentation (SSF). The pH is usually between 4.2-4.8, e.g., pH 4.5. In a simultaneous saccharification and fermentation (SSF) process, there is no holding stage for saccharification, rather, the yeast and enzymes are added together.

In a typical saccharification process, maltodextrins produced during liquefaction are converted into dextrose by adding a glucoamylase and optionally a debranching enzyme, such as an isoamylase (U.S. Pat. No. 4,335,208) or a pullulanase. The temperature is lowered to 60° C., prior to the addition of the glucoamylase and debranching enzyme. The saccharification process proceeds for 24-72 hours. Prior to addition of the saccharifying enzymes, the pH is reduced to below 4.5, while maintaining a high temperature (above 95° C.), to inactivate the liquefying alpha-amylase. This process reduces the formation of short oligosaccharide called "panose precursors," which cannot be hydrolyzed properly by the debranching enzyme.

Normally, about 0.2-0.5% of the saccharification product is the branched trisaccharide panose (Glc pα1-6Glc pα1-4Glc), which cannot be degraded by a pullulanase. If active amylase from the liquefaction remains present during saccharification (i.e., no denaturing), the amount of panose can be as high as 1-2%, which is highly undesirable since it lowers the saccharification yield significantly.

Other fermentation products may be fermented at conditions and temperatures well known to persons skilled in the art, suitable for the fermenting organism in question.

The fermentation product may be recovered by methods well known in the art, e.g., by distillation.

In a particular embodiment, the process of the invention further comprises, prior to the conversion of a starch-containing material to sugars/dextrins the steps of:

(x) reducing the particle size of the starch-containing material; and (y) forming a slurry comprising the starch-containing material and water.

In an embodiment, the starch-containing material is milled to reduce the particle size. In an embodiment the particle size is reduced to between 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

The aqueous slurry may contain from 10-55 wt. % dry solids (DS), preferably 25-45 wt. % dry solids (DS), more preferably 30-40 wt. % dry solids (DS) of starch-containing material.

Conventional starch-conversion processes, such as liquefaction and saccharification processes are described, e.g., in U.S. Pat. No. 3,912,590, EP 252730 and EP 063909.

In an embodiment, the conversion process degrading starch to lower molecular weight carbohydrate components such as sugars or fat replacers includes a debranching step.

In the case of converting starch into a sugar, the starch is depolymerized. Such a depolymerization process consists of, e.g., a pre-treatment step and two or three consecutive process steps, i.e., a liquefaction process, a saccharification process, and depending on the desired end-product, an optional isomerization process.

When the desired final sugar product is, e.g., high fructose syrup the dextrose syrup may be converted into fructose. After the saccharification process, the pH is increased to a value in the range of 6-8, e.g., pH 7.5, and the calcium is removed by ion exchange. The dextrose syrup is then converted into high fructose syrup using, e.g., an immobilized glucose isomerase.

Production of Fermentation Products

Fermentable sugars (e.g., dextrins, monosaccharides, particularly glucose) are produced from enzymatic saccharification. These fermentable sugars may be further purified and/or converted to useful sugar products. In addition, the sugars may be used as a fermentation feedstock in a microbial fermentation process for producing end-products, such as alcohol (e.g., ethanol, and butanol), organic acids (e.g., succinic acid, 3-HP and lactic acid), sugar alcohols (e.g., glycerol), ascorbic acid intermediates (e.g., gluconate, 2-keto-D-gluconate, 2,5-diketo-D-gluconate, and 2-keto-L-gluonic acid), amino acids (e.g., lysine), proteins (e.g., antibodies and fragment thereof).

In an embodiment, the fermentable sugars obtained during the liquefaction process steps are used to produce alcohol and particularly ethanol. In ethanol production, an SSF process is commonly used wherein the saccharifying enzymes and fermenting organisms (e.g., yeast) are added together and then carried out at a temperature of 30-40° C.

The organism used in fermentation will depend on the desired end-product. Typically, if ethanol is the desired end product yeast will be used as the fermenting organism. In some preferred embodiments, the ethanol-producing microorganism is a yeast and specifically *Saccharomyces* such as strains of *S. cerevisiae* (U.S. Pat. No. 4,316,956). A variety of *S. cerevisiae* are commercially available, and these include but are not limited to FALI (Fleischmann's Yeast), SUPERSTART (Alltech), FERMIOL (DSM Specialties), RED STAR (Lesaffre) and Angel alcohol yeast (Angel Yeast Company, China). The amount of starter yeast employed in the methods is an amount effective to produce a commercially significant amount of ethanol in a suitable amount of time, (e.g., to produce at least 10% ethanol from a substrate having between 25-40% DS in less than 72 hours). Yeast cells are generally supplied in amounts of about $10^4$ to about $10^{12}$, and preferably from about $10^7$ to about $10^{10}$ viable yeast count per mL of fermentation broth. After yeast is added to the mash, it is typically subjected to fermentation for about 24-96 hours, e.g., 35-60 hours. The temperature is between about 26-34° C., typically at about 32° C., and the pH is from pH 3-6, e.g., around pH 4-5.

The fermentation may include, in addition to fermenting microorganisms (e.g., yeast), nutrients, and additional enzymes, including phytases. The use of yeast in fermentation is well known in the art.

In further embodiments, use of appropriate fermenting microorganisms, as is known in the art, can result in fermentation end product including, e.g., glycerol, 1,3-propanediol, gluconate, 2-keto-D-gluconate, 2,5-diketo-D-gluconate, 2-keto-L-gulonic acid, succinic acid, lactic acid, amino acids, and derivatives thereof. More specifically when lactic acid is the desired end product, a *Lactobacillus* sp. (*L. casei*) may be used; when glycerol or 1,3-propanediol are the desired end-products *E. coli* may be used; and when 2-keto-D-gluconate, 2,5-diketo-D-gluconate, and 2-keto-L-gulonic acid are the desired end products, *Pantoea citrea* may be used as the fermenting microorganism. The above enumerated list are only examples and one skilled in the art will be aware of a number of fermenting microorganisms that may be used to obtain a desired end product.

Processes for Producing Fermentation Products from Un-Gelatinized Starch-Containing Material The invention relates to processes for producing fermentation products from starch-containing material without gelatinization (i.e., without cooking) of the starch-containing material (often referred to as a "raw starch hydrolysis" process). The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of an alpha-amylase of the invention and carbohydrate-source generating enzyme(s) to produce sugars that can be fermented into the fermentation product by a suitable fermenting organism. In this embodiment the desired fermentation product, e.g., ethanol, is produced from un-gelatinized (i.e., uncooked), preferably milled, cereal grains, such as corn.

Accordingly, in one aspect the invention relates to processes for producing a fermentation product from starch-containing material comprising simultaneously saccharifying and fermenting starch-containing material using a carbohydrate-source generating enzymes and a fermenting organism at a temperature below the initial gelatinization temperature of said starch-containing material in the presence of an alpha-amylase of the invention.

Saccharification and fermentation may also be separate. Thus, in another aspect the invention relates to processes of producing fermentation products, comprising the following steps:

(i) saccharifying a raw starch-containing material at a temperature below the initial gelatinization temperature; and (ii) fermenting using a fermentation organism;

wherein step (i) is carried out using at least an alpha-amylase of the invention, and optionally a glucoamylase.

In one embodiment, the fermenting organism, preferably a *Saccharomyces cerevisiae*, expresses the alpha-amylase of the invention and/or a glucoamylase.

In one embodiment, the fermenting organism, preferably a *Saccharomyces cerevisiae*, expresses the alpha-amylase of the invention and another alpha-amylase.

In an embodiment the other alpha-amylase is of fungal or bacterial origin. In a preferred embodiment the other alpha-amylase is a fungal acid stable alpha-amylase. A fungal acid stable alpha-amylase is an alpha-amylase that has activity in the pH range of 3.0 to 7.0 and preferably in the pH range from 3.5 to 6.5, including activity at a pH of about 4.0, 4.5, 5.0, 5.5, and 6.0.

In a preferred embodiment the other alpha-amylase expressed by the fermenting organism in fermentation is derived from a strain of the genus *Rhizomucor*, preferably a strain the *Rhizomucor pusillus*, such as one shown in SEQ ID NO: 3 in WO 2013/006756, such as a *Rhizomucor pusillus* alpha-amylase hybrid having an *Aspergillus niger* linker and starch-binding domain, such as the one shown in SEQ ID NO: 12 herein, or a variant thereof.

In an embodiment the other alpha-amylase is selected from the group consisting of:

(i) an alpha-amylase comprising the polypeptide of SEQ ID NO: 12 herein;

(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 12 herein.

In a preferred embodiment the other alpha-amylase is a variant of the alpha-amylase shown in SEQ ID NO: 12 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 12 for numbering).

In an embodiment the alpha-amylase is derived from a *Rhizomucor pusillus* with an *Aspergillus niger* glucoamylase linker and starch-binding domain (SBD), preferably disclosed as SEQ ID NO: 12 herein, preferably having one or more of the following substitutions: G128D, D143N, preferably G128D+D143N (using SEQ ID NO: 12 for numbering).

In an embodiment the other alpha-amylase variant present and/or added in saccharification and/or fermentation has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 12 herein.

The fermentation product, e.g., ethanol, may optionally be recovered after fermentation, e.g., by distillation. Typically, amylase(s), such as glucoamylase(s) and/or other carbohydrate-source generating enzymes, and/or alpha-amylase(s), is (are) present during fermentation. Examples of glucoamylases and other carbohydrate-source generating enzymes include raw starch hydrolyzing glucoamylases. Examples of alpha-amylase(s) include acid alpha-amylases such as acid fungal alpha-amylases, particularly the alpha-amylase of the invention. Examples of fermenting organisms include yeast, e.g., a strain of *Saccharomyces cerevisiae*. The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Stärke* 44 (12): 461-466. Before initiating the process, a slurry of starch-containing material, such as granular starch, having 10-55 w/w % dry solids (DS), preferably 25-45 w/w % dry solids, more preferably 30-40 w/w % dry solids of starch-containing material may be prepared. The slurry may include water and/or process waters, such as stillage (backset), scrubber water, evaporator condensate or distillate, side-stripper water from distillation, or process water from other fermentation product plants. Because the process of the invention is carried out below the initial gelatinization temperature, and thus no significant viscosity increase takes place, high levels of stillage may be used if desired. In an embodiment the aqueous slurry contains from about 1 to about 70 vol. %, preferably 15-60 vol. %, especially from about 30 to 50 vol. % water and/or process waters, such as stillage (backset), scrubber water, evaporator condensate or distillate, side-stripper water from distillation, or process water from other fermentation product plants, or combinations thereof, or the like. The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolyzate. A process in this aspect of the invention is conducted at a temperature below the initial gelatinization temperature, which means that the temperature typically lies in the range between 30-75° C., preferably between 45-60° C. In a preferred embodiment the process carried at a temperature from 25° C. to 40° C., such as from 28° C. to 35° C., such as from 30° C. to 34° C., preferably around 32°

C. In an embodiment the process is carried out so that the sugar level, such as glucose level, is kept at a low level, such as below 6 w/w %, such as below about 3 w/w %, such as below about 2 w/w %, such as below about 1 w/w %, such as below about 0.5 w/w %, or below 0.25 w/w %, such as below about 0.1 w/w %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 w/w %, such as below about 0.2 w/w %. The process of the invention may be carried out at a pH from about 3 and 7, preferably from pH 3.5 to 6, or more preferably from pH 4 to 5. In an embodiment fermentation is ongoing for 6 to 120 hours, in particular 24 to 96 hours.

Processes for Producing Fermentation Products from Gelatinized Starch-Containing Material In this aspect, the invention relates to processes for producing fermentation products, especially ethanol, from starch-containing material, which process includes a liquefaction step and sequentially or simultaneously performed saccharification and fermentation steps.

Consequently, the invention relates to processes for producing fermentation products from starch-containing material comprising the steps of:

(a) liquefying starch-containing material at a temperature above the initial gelatinization temperature in the presence of an alpha-amylase;
(b) saccharifying the liquefied material obtained in step (a) using a variant alpha-amylase of the invention, and optionally a glucoamylase; and
(c) fermenting using a fermenting organism.

In an embodiment, a protease, such as a thermo-stable serine protease, an acid fungal protease or a metallo protease is added before, during and/or after liquefaction. In an embodiment the metalloprotease is derived from a strain of *Thermoascus*, e.g., a strain of *Thermoascus aurantiacus*, especially *Thermoascus aurantiacus* CGMCC No. 0670. In another embodiment the protease is a bacterial protease, particularly a serine protease, e.g., an S8 protease, more particularly a protease derived from a strain of *Pyrococcus* or *Thermococcus*, more particularly from *Pyrococcus furiosus* disclosed in U.S. Pat. No. 6,358,726, or SEQ ID NO: 10 herein.

In an embodiment the glucoamylase is derived from a strain of *Aspergillus*, e.g., *Aspergillus niger* or *Aspergillus awamori*, a strain of *Talaromyces*, especially *Talaromyces emersonii*; or a strain of *Athelia*, especially *Athelia rolfsii*; a strain of *Trametes*, e.g., *Trametes cingulata*; or a strain of *Pycnoporus*, or a strain of *Gloeophyllum*, such as *G. serpiarium* or *G. trabeum*, or a strain of the *Nigrofomes*; or a mixture thereof. Saccharification step (b) and fermentation step (c) may be carried out either sequentially or simultaneously. A pullulanase and/or protease may be added during saccharification and/or fermentation when the process is carried out as a sequential saccharification and fermentation process and before or during fermentation when steps (b) and (c) are carried out simultaneously (SSF process). The pullulanase and/or protease may also advantageously be added before liquefaction (pre-liquefaction treatment), i.e., before or during step (a), and/or after liquefaction (post liquefaction treatment), i.e., after step (a). The pullulanase is most advantageously added before or during liquefaction, i.e., before or during step (a). The fermentation product, such as especially ethanol, may optionally be recovered after fermentation, e.g., by distillation. The fermenting organism is preferably yeast, preferably a strain of *Saccharomyces cerevisiae*. In a preferred embodiment, the yeast is expressing the variant glucoamylase of the invention. In a particular embodiment, the process of the invention further comprises, prior to step (a), the steps of:

x) reducing the particle size of the starch-containing material, preferably by milling (e.g., using a hammer mill);
y) forming a slurry comprising the starch-containing material and water.

In an embodiment, the particle size is smaller than a #7 screen, e.g., a #6 screen. A #7 screen is usually used in conventional prior art processes. The aqueous slurry may contain from 10-55, e.g., 25-45 and 30-40, w/w % dry solids (DS) of starch-containing material. The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C., at pH 4-6, preferably 4.5-5.5, and alpha-amylase variant, optionally together with a pullulanase and/or protease, preferably metalloprotease, are added to initiate liquefaction (thinning). In an embodiment the slurry may then be jet-cooked at a temperature between 95-140° C., preferably 100-135° C., such as 105-125° C., for about 1-15 minutes, preferably for about 3-10 minutes, especially around about 5 minutes. The slurry is cooled to 60-95° C. and more alpha-amylase and optionally pullulanase and/or protease, preferably metalloprotease, is (are) added to finalize hydrolysis (secondary liquefaction). The liquefaction process is usually carried out at pH 4.5-6.5, such as around 4.8, or a pH between 5.0-6.2, such as 5.0-6.0, such as between 5.0-5.5, such as around 5.2, such as around 5.4, such as around 5.6, such as around 5.8. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 36° C., such as from 30° C. to 34° C., preferably around about 32° C. In an embodiment fermentation is ongoing for 6 to 120 hours, in particular 24 to 96 hours.

Processes for Producing Syrup from Gelatinized Starch-Containing Material

In this aspect the fermentation step is left out, however, conditions are generally as described above for "Processes for producing fermentation products from gelatinized starch-containing material". Thus, in this aspect the present invention relates to a process for producing a syrup from starch-containing material comprising the steps of:

a) liquefying the starch-containing material at a temperature above the initial gelatinization temperature in the presence of an alpha-amylase; and b) saccharifying the product of step a) in the presence of a glucoamylase and a variant alpha-amylase of the invention.

Protease Present and/or Added During Liquefaction

According to the invention a thermostable protease may in one embodiment be present and/or added during liquefaction together with an alpha-amylase, such as a thermostable alpha-amylase, and optionally a carbohydrate-source generating enzyme, in particular a thermostable glucoamylase or thermostable pullulanase.

Proteases are classified on the basis of their catalytic mechanism into the following groups: Serine proteases(S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

There are no limitations on the origin of the protease used in a process of the invention as long as it fulfills the thermostability properties defined below.

The protease may be a variant of, e.g., a wild-type protease as long as the protease has the thermostability properties defined herein.

In an embodiment the protease has a thermostability above 60%, such as above 90%, such as above 100%, such as above 110% at 85° C. as determined using the Zein-BCA assay.

In an embodiment protease has a thermostability between 60-120, such as between 70-120%, such as between 80-120%, such as between 90-120%, such as between 100-120%, such as 110-120% at 85° C. as determined using the Zein-BCA assay.

In one embodiment the thermostable protease is a variant of a metallo protease as defined above. In an embodiment the thermostable protease used in a process of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In a preferred embodiment the thermostable protease is a variant of the metallo protease disclosed as the mature part of SEQ ID NO: 2 disclosed in WO 2003/048353 or the mature part of SEQ ID NO: 1 in WO 2010/008841 with the following mutations:

D79L+S87P+A112P+D142L;

D79L+S87P+D142L; or

A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841.

The thermostable protease may also be derived from a bacterium, particularly a serine protease, more particularly an S8 protease, more particularly an S8 protease from *Pyrococcus* sp or *Thermococcus* sp.

In an embodiment the thermostable protease is derived from a strain of the bacterium *Pyrococcus*, such as a strain of *Pyrococcus furiosus* (pfu protease).

In an embodiment the protease is one shown as SEQ ID NO: 1 in U.S. Pat. No. 6,358,726-B1 (Takara Shuzo Company) and SEQ ID NO: 10 herein.

In another embodiment the thermostable protease is one disclosed in SEQ ID NO: 10 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 10 herein.

Glucoamylase Present and/or Added in Liquefaction

In an embodiment a glucoamylase is present and/or added in liquefaction step a) in a process of the invention (i.e., oil recovery process and fermentation product production process).

In a preferred embodiment the glucoamylase present and/or added in liquefaction step a) is derived from a strain of the genus *Penicillium*, especially a strain of *Penicillium oxalicum* disclosed as SEQ ID NO: 2 in WO 2011/127802 or SEQ ID NO: 11 herein.

In an embodiment the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NO: 11 herein.

In a preferred embodiment the glucoamylase is a variant of the *Penicillium oxalicum* glucoamylase shown in SEQ ID NO: 2 in WO 2011/127802 or SEQ ID NO: 11 herein having a K79V substitution (using the mature sequence shown in SEQ ID NO: 11 for numbering), such as a variant disclosed in WO 2013/053801.

In a preferred embodiment the glucoamylase present and/or added in liquefaction is the *Penicillium oxalicum* glucoamylase having a K79V substitution and preferably further one of the following substitutions:

P11F+T65A+Q327F;

P2N+P4S+P11F+T65A+Q327F (using SEQ ID NO: 11 for numbering).

In an embodiment the glucoamylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 11 herein.

The glucoamylase may be added in amounts from 0.1-100 micro grams EP/g, such as 0.5-50 micro grams EP/g, such as 1-25 micrograms EP/g, such as 2-12 micrograms EP/g DS.

Glucoamylase Present and/or Added in Saccharification and/or Fermentation

A glucoamylase is present and/or added in saccharification and/or fermentation, preferably simultaneous saccharification and fermentation (SSF), in a process of the invention (i.e., oil recovery process and fermentation product production process).

In an embodiment the glucoamylase present and/or added in saccharification and/or fermentation is of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *T. emersonii* or a strain of *Trametes*, preferably *T. cingulata*, or a strain of *Pycnoporus*, or a strain of *Gloeophyllum*, such as *G. serpiarium* or *G. trabeum*, or a strain of the *Nigrofomes*.

In an embodiment the glucoamylase is derived from *Trametes*, such as a strain of *Trametes cingulata*, such as the one shown in SEQ ID NO: 7 herein.

In an embodiment the glucoamylase is selected from the group consisting of:

(i) a glucoamylase comprising the polypeptide of SEQ ID NO: 7 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 7 herein.

In an embodiment the glucoamylase is derived from *Talaromyces*, such as a strain of *Talaromyces emersonii*, such as the one shown in SEQ ID NO: 8 herein.

In an embodiment the glucoamylase is selected from the group consisting of:

(i) a glucoamylase comprising the polypeptide of SEQ ID NO: 8 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 8 herein.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL and AMG™ E (from Novozymes A/S); OPTIDEX™ 300, GC480, GC417 (from DuPont); AMIGASE™ and AMIGASE™ PLUS (from DSM); G-ZYME™ G900, G-ZYME™ and G990 ZR (from DuPont).

According to a preferred embodiment of the invention the glucoamylase is present and/or added in saccharification and/or fermentation in combination with a variant alpha-amylase of the invention. Examples of suitable alpha-amylase are described below.

Alpha-Amylase Present and/or Added in Saccharification and/or Fermentation

In an embodiment a variant alpha-amylase of the invention is present and/or added in saccharification and/or fermentation in a process of the invention. In a preferred embodiment the alpha-amylase is of fungal or bacterial origin. In a preferred embodiment the alpha-amylase is a fungal acid stable alpha-amylase of the invention. A fungal acid stable alpha-amylase is an alpha-amylase that has activity in the pH range of 3.0 to 7.0 and preferably in the pH range from 3.5 to 6.5, including activity at a pH of about 4.0, 4.5, 5.0, 5.5, and 6.0.

In a preferred embodiment the alpha-amylase present and/or added in saccharification and/or fermentation is derived from a strain of the genus *Bacillus*, preferably a strain the *Bacillus licheniformis*, such as one shown in SEQ ID NO: 1 herein.

In an embodiment the alpha-amylase present and/or added in saccharification and/or fermentation is selected from a variant alpha-amylase of the invention or a variant alpha-amylase of the invention having at least 80%, at least 85%, at least 90%, at least 91%, at least 92%, at least 93%, at least 94%, at least 95%, at least 96%, at least 97%, at least 98%, at least 99% or 100% identity to SEQ ID NO: 1, SEQ ID NO: 2, SEQ ID NO: 3 or SEQ ID NO: 4.

In a preferred embodiment, the ratio between glucoamylase and variant alpha-amylase present and/or added during saccharification and/or fermentation may preferably be in the range from 500:1 to 1:1, such as from 250:1 to 1:1, such as from 100:1 to 1:1, such as from 100:2 to 100:50, such as from 100:3 to 100:70.

Fermentation Medium

The environment in which fermentation is carried out is often referred to as the "fermentation media" or "fermentation medium". The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

The term "fermenting organism" refers to any organism, including bacterial and fungal organisms, especially yeast, suitable for use in a fermentation process and capable of producing the desired fermentation product. Especially suitable fermenting organisms are able to ferment, i.e., convert, sugars, such as glucose or maltose, directly or indirectly into the desired fermentation product, such as ethanol. Examples of fermenting organisms include fungal organisms, such as yeast. Preferred yeast includes strains of *Saccharomyces* spp., in particular, *Saccharomyces cerevisiae.*

Suitable concentrations of the viable fermenting organism during fermentation, such as SSF, are well known in the art or can easily be determined by the skilled person in the art. In one embodiment the fermenting organism, such as ethanol fermenting yeast, (e.g., *Saccharomyces cerevisiae*) is added to the fermentation medium so that the viable fermenting organism, such as yeast, count per mL of fermentation medium is in the range from $10^5$ to $10^{12}$, preferably from $10^7$ to $10^{10}$, especially about $5\times10^7$.

Examples of commercially available yeast includes, e.g., RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC-North American Bioproducts Corporation, GA, USA), GERT STRAND (available from Gert Strand AB, Sweden), and FERMIOL (available from DSM Specialties).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived therefrom, or cereals. Contemplated are also waxy and non-waxy types of corn and barley. In a preferred embodiment the starch-containing material, used for ethanol production according to the invention, is corn or wheat.

Fermentation Products

The term "fermentation product" means a product produced by a process including a fermentation step using a fermenting organism. Fermentation products contemplated according to the invention include alcohols (e.g., ethanol, methanol, butanol; polyols such as glycerol, sorbitol and inositol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferably processes of the invention are used for producing an alcohol, such as ethanol. The fermentation product, such as ethanol, obtained according to the invention, may be used as fuel, which is typically blended with gasoline. However, in the case of ethanol it may also be used as potable ethanol.

Recovery of Fermentation Products

Subsequent to fermentation, or SSF, the fermentation product may be separated from the fermentation medium. The slurry may be distilled to extract the desired fermentation product (e.g., ethanol). Alternatively, the desired fermentation product may be extracted from the fermentation medium by micro or membrane filtration techniques. The fermentation product may also be recovered by stripping or other method well known in the art.

Plants

The present invention also relates to isolated plants, e.g., a transgenic plant, plant part, or plant cell, comprising a polynucleotide of the present invention so as to express and produce the variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor, or for reducing the amount of alpha-amylase needed in saccharification of starch, and optionally fermenting the glucose to a fermentation product, such as an alcohol.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86:506.

For constitutive expression, the 35S-CaMV, the maize ubiquitin 1, or the rice actin 1 promoter may be used (Franck et al., 1980, *Cell* 21:285-294; Christensen et al., 1992, *Plant Mol. Biol.* 18:675-689; Zhang et al., 1991, *Plant Cell* 3:1155-1165). Organ-specific promoters may be, for example, a promoter from storage sink tissues such as seeds, potato tubers, and fruits (Edwards and Coruzzi, 1990, *Ann. Rev. Genet.* 24:275-303), or from metabolic sink tissues such as meristems (Ito et al., 1994, *Plant Mol. Biol.* 24:863-878), a seed specific promoter such as the glutelin, prolamin, globulin, or albumin promoter from rice (Wu et al., 1998, *Plant Cell Physiol.* 39:885-889), a *Vicia faba* promoter from the legumin B4 and the unknown seed protein gene from *Vicia faba* (Conrad et al., 1998, *J. Plant Physiol.* 152:708-

711), a promoter from a seed oil body protein (Chen et al., 1998, *Plant Cell Physiol.* 39:935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102:991-1000), the *chlorella* virus adenine methyltransferase gene promoter (Mitra and Higgins, 1994, *Plant Mol. Biol.* 26:85-93), the aldP gene promoter from rice (Kagaya et al., 1995, *Mol. Gen. Genet.* 248:668-674), or a wound inducible promoter such as the potato pin2 promoter (Xu et al., 1993, *Plant Mol. Biol.* 22:573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244:1293; Potrykus, 1990, *Bio/Technology* 8:535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19:15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2:275-281; Shimamoto, 1994, *Curr. Opin. Biotechnol.* 5:158-162; Vasil et al., 1992, *Bio/Technology* 10:667-674). An alternative method for transformation of monocots is based on protoplast transformation as described by Omirulleh et al., 1993, *Plant Mol. Biol.* 21:415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site-specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and (b) recovering the variant.

The present invention is further illustrated by the following numbered embodiments.

Embodiment 1. An alpha-amylase variant of a parent alpha-amylase, comprising an alteration at one or more positions corresponding to positions 196, 1, 2, 3, 4, 5, 6, 7, 8, 9, 10, 11, 12, 13, 14, 15, 16, 28, 38, 39, 43, 54, 56, 57, 64, 67, 68, 70, 71, 86, 89, 90, 94, 96, 99, 101, 103, 107, 108, 110, 113, 114, 117, 127, 134, 138, 142, 150, 151, 152, 156, 169, 171, 174, 179, 183, 193, 199, 200, 204, 205, 207, 208, 209, 212, 218, 221, 222, 224, 233, 241, 245, 259, 275, 278, 281, 282, 283, 284, 285, 308, 323, 335, 348, 359, 382, 386, 388, 392, 394, 396, 412, 414, 417, 424, 428, 457, 459, 466, 479, 489, 511, 533, 534, 542, 543, 545, 547, 549, 550, 551, 560, 566, 570, 574, 575, 576, 577, 578, 580, 581, 582, 589, 592, 599, 603, 605, 608, 614, 619, or 626 of the polypeptide of SEQ ID NO: 1, wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 1, SEQ ID NO: 2, SEQ ID NO: 3, or SEQ ID NO: 4.

Embodiment 2. An alpha-amylase variant according to embodiment 1, comprising a substitution at one or more positions corresponding to positions 196, 199, 64, 96, 150, 179, 207, 222, 284 and 603 of the polypeptide of SEQ ID NO: 1, wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 1, SEQ ID NO: 2, SEQ ID NO: 3, or SEQ ID NO: 4.

Embodiment 3. The variant of embodiment 1, which comprises an alteration selected from the group consisting of: E1*, T2*, A3*, N4*, K5*, S6*, N7*, K8*, V9*, V9D, V9L, T10*, T10I, A11*, S12*, S12P, S13*, V14*, V14I, K15*, N16*, N16S, N28R, N28W, R38H, R38Y, D39R, A43D, A43T, A43V, K541, G56P, G56W, N57P, R64S, Y67T, Y67W, W68S, W68Y, Y70F, Q71E, Q71N, Q86R, K89R, D90E, A94D, E96H, E96K, G99N, K101R, I103Y, V107T, I108L, I108P, H110D, S113D, S113F, S113G, S113H, S113Q, S113W, S113Y, D114Q, A117T, N127D, Q134E, Q134L, Q134M, Q134N, Q134T, Q134W, W138Y, W142E, L150F, L150H, L150M, L150S, L150V, L150W, L150Y, G151F, G151S, G151W, G151Y, L152M, N156K, N156R, F169H, E171Q, L174I, D179G, D179S, Y183F, Y183I, D193S, D193DQ, D193DY, D193DQY, D193SQY N196W, S199G, Q200W, N204D, I205Y, N207W, T208N, T208S, S209L, F212W, L218F, L218W, S221N, A222E, A222I, A222V, R224K, N233S, H241N, S245N, H259Y, S275L, S275N, T278N, T278W, T278Y, N281Q, N281S, D282P, D283*, D283A, D283P, E284Q, E285V, T308M, T308Y, R323K, S335K, S335Q, S335R, T348K, E359Y, A382T, S386D, S388W, N392R, N392W, S394K, K396S, Q412W, A414K, K417W, K417Y, A424P, A428S, Q457L, Q457R, T459M, A466V, Q479QP, L489Q, E511D, G533H, Y534H, Q542K, V543P, A545P, I547Y, K549*, K549Y, H550*, H550Y, D551*, G560P, A566P, N570H, M574MW, M574W, Y575W, T576Y, L577Y, T578Y, P580*, E581*, N582*, K589F, F592FK, V599W, N603W, P605S, D608Y, L614W, G619W, and H626*.

Embodiment 4. The variant of embodiment 2, which comprises an alteration selected from the group consisting of: R64S, E96K, L150Y, L150W, L150H, L150M, L150F, D179S, N196W, S199G, N207W, A222E, A222I, A222V, E284Q, N603W, and H626*.

Embodiment 5. The variant of any one of embodiments 1-4, which has an improved property relative to the parent, wherein the improved property is increased pH stability at pH 4.0, 32° C. to 37° C., preferably 32° C., compared to a parent alpha-amylase, particularly the alpha-amylase disclosed as SEQ ID NO: 1.

Embodiment 6. The variant of any of embodiments 1-5, comprising a substitution or a combination of substitutions selected from:

A222I;
A222V;
A222E;
S199G;
N196W;
N207W;
N603W;
L150Y;
L150W;
L150H;
L150M;
L150F;
R64S;
E96K;
D179S;
E284Q;
N207W+N603W;
N196W+N207W;
N196W+N603W;
N196W+N207W+N603W;
A222I+S199G+N196W;
A222V+S199G+N196W;
A222E+S199G+N196W;
A222V+S199G+N196W+L150Y;
L150H+S199G+A222I;
L150M+S199G+A222V;
N196W+S199G+A222V+N603W;
L150F+N196W+S199G+A222I;
L150M+N196W+S199G+A222V;
L150W+S199G+A222V;
L150H+N196W+S199G+A222V;
L150W+N196W+S199G+A222I;
L150Y+S199G+A222V;
E96K+D179S+N196W+S199G+A222V+E284Q;
R64S+E96K+N196W+S199G+A222V;

wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 1, SEQ ID NO: 2, SEQ ID NO: 3, or SEQ ID NO: 4.

Embodiment 7. The variant of any of embodiments 1-6, comprising a N-terminal deletion, more particularly comprising at least amino acids 11 to 626 of SEQ ID NO: 1, at least amino acids 12 to 626 of SEQ ID NO: 1, such as at least amino acids 13 to 626 of SEQ ID NO: 1.

Embodiment 8. The variant of any of embodiments 1-7, wherein the alpha-amylase further comprises a C-terminal deletion, particularly H626*.

Embodiment 9. The variant alpha-amylase of any of embodiments 1-5, comprising an alteration or a combination of alterations selected from:

N28W;
N196W;
S199G;
N196W+V599W;
N196W+H550Y+P605S;
N196W+A545P+T576Y;
N196W+K549Y+G560P;
I108P+Y183I+N196W+I205Y;
N196W+R323K;
N196W+D283P;
W138Y+N196W;
L150W;
N196W+N392W+K417W;
N196W+N392R+K417W;
N196W+K549*+H550*+D551*;
N196W+P580*+E581*+N582*;
N196W+F592FK;
N28W+N196W+N207W+S386D+N603W;
R38Y+N196W;
N196W+H259Y;
N196W+Q412W;
N196W+F212W;
N196W+V599W;
N196W+H550Y+P605S;
N196W+H550Y+K589F;
N196W+H550Y+D608Y;
N196W+M574W+L614W;
N196W+G533H+M574W+L614W;
N196W+V543P+N570H;
N196W+G533H+Y575W+L614W;
N196W+A545P+T576Y;
N196W+A566P+T578Y;
N196W+K549Y+G560P;
N196W+A566P+L577Y;

N196W+I547Y+G560P;
N196W+M574MW;
N196W+K549*+H550*+D551*+M574MW+P580*+E581*+N582*+F592FK;
N196W+L614W+G619W;
N28W+I108P+N196W+N207W+S386D+A466V+Q542K+N603W;
N28W+I108P+N196W+N207W+S386D+N603W;
N196W+D282P+D283*;
W138Y+N196W;
N28W+N196W+N207W+S386D+N603W;
N196W+S388W+A424P;
N196W+S388W+A424P+L489Q;
A117T+N196W+H550Y+D608Y;
N196W+Q457R+Y575W+L614W;
N196W+S199G;
N196W+A222V;
N196W+A222E;
N196W+A222I;
S199G+A222V;
S199G+A222E;
S199G+A222I;
N196W+S199G+A222I;
Q134L;
L150W+N156K+N196W+S199G+A222V;
L150Y+N156K+N196W+S199G+A222I;
L150W+N196W+S199G+A222I+A428S;
L150F+N156K+N196W+S199G+A222I;
L150Y+N156R+N196W+A222V;
L150M+N156R+N196W+S199G+A222I;
L150M+N156R+N196W+A222V;
L150Y+N156R+N196W+S199G+A222V;
L150M+N156K+N196W+S199G+A222V;
L150Y+N156R+N196W+A222I;
L150H+N156R+N196W+S199G+A222I;
L150H+N156K+N196W+A222V;
L150W+N156R+N196W+A222I;
L150F+N156R+N196W+A222I;
L150F+N156K+N196W+S199G+A222V;
L150H+N156K+N196W+S199G+A222V;
L150F+N156R+S199G+A222I;
L150M+N156K+N196W+A222V;
L150W+N156K+N196W+S199G+A222I;
N156K+N196W+S199G+A222V;
L150Y+N156R+S199G+A222I;
L150M+N156R+S199G+A222I;
L150W+N156K+S199G+A222V;
L150W+N156R+N196W+S199G+A222V;
L150Y+N156R+N196W;
N156K+N196W+A222V;
N156K+N196W+S199G;
N156R+S199G+A222V;
S113H+N196W+S199G+A222V;
Q71E+S113H+N196W+S199G+A222V;
N196W+S199G+A222V+D283A;
N196W+S199G+A222V+D283P;
W142E+D193SQY+N196W+S199G+A222V+R224K;
E96K+K101R+L150W+N156R+D179S+N196W+S199G+T208N+A222V;
E96K+K101R+L150Y+N156R+D179S+N196W+S199G+T208N+A222V+E284Q;
E96K+K101R+L150M+N156R+D179S+N196W+S199G+T208N+A222V+E284Q;
S113Q+Q134E+N196W+S199G+A222V;
S113D+Q134N+N196W+S199G+A222V;
S113F+N196W+S199G+A222V;
E171Q+N196W+S199G+N204D+A222V;
N196W+S199G+A222V+H241N+S245N+T278N+E284Q+E285V;
N196W+S199G+A222V+S394K+A414K+K417Y;
N196W+S199G+A222V+E359Y+S394K+K396S+A414K+K417Y;
R38H+E96K+G99N+K101R+D179S+N196W+S199G+A222V;
R38H+E96K+G99N+K101R+D179S+N196W+S199G+A222V+E284Q;
V107T+H110D+N196W+S199G+A222V;
Q134T+L150Y+N196W+S199G+A222V;
S113F+L150W+N196W+S199G+A222V;
S113F+L150Y+N196W+S199G+A222V;
E96K+K101R+N156R+D179S+N196W+S199G+T208N+A222V;
E96K+K101R+L150Y+N156R+D179S+N196W+S199G+T208N+A222V;
E96K+K101R+L150M+N156R+D179S+N196W+S199G+T208N+A222V;
E96K+K101R+N156R+D179S+N196W+S199G+T208N+A222V+E284Q;
E96K+K101R+L150W+N156R+D179S+N196W+S199G+T208N+A222V+E284Q;
N28R+Q86R+N196W+S199G+A222V;
N28R+Q86R+K89R+N196W+S199G+A222V;
G56P+N196W+S199G+S209L+A222V;
E96K+N196W+S199G+A222V;
T10I+N196W+S199G+A222V;
D39R+N196W+S199G+A222V;
R64S+N196W+S199G+A222V;
T10I+D39R+R64S+N196W+S199G+A222V;
T10I+D39R+N196W+S199G+A222V;
D39R+E96K+N196W+S199G+A222V;
R64S+D90E+E96K+N196W+S199G+A222V;
R38H+D39R+E96K+G99N+K101R+D179S+N196W+S199G+A222V;
R38H+R64S+E96K+G99N+K101R+D179S+N196W+S199G+A222V;
T10I+R38H+R64S+E96K+G99N+K101R+D179S+N196W+S199G+A222V;
T10I+R38H+R64S+D90E+E96K+G99N+K101R+D179S+N196W+S199G+A222V;
T10I+R38H+D39R+E96K+G99N+K101R+D179S+N196W+S199G+A222V;
R38H+D39R+R64S+E96K+G99N+K101R+D179S+N196W+S199G+A222V;
E96K+N196W+S199G+A222V+E284Q;
T10I+N196W+S199G+A222V+E284Q;
D39R+N196W+S199G+A222V+E284Q;
R64S+N196W+S199G+A222V+E284Q;
T10I+D39R+E96K+N196W+S199G+A222V+E284Q;
D193SQY+N196W+S199G+A222V;
Q134T+N196W+S199G+A222V;
L1741+N196W+S199G+T208N+A222V;
Y183F+N196W+S199G+T208S+A222V;
N127D+N156R+N196W+S199G+A222V;
Q134T+L150W+N196W+S199G+A222V;
N57P+N196W+S199G+A222V;
N196W+S199G+Q200W+A222V;
T10I+D39R+R64S+E96K+N196W+S199G+A222V+E284Q;
T10I+D39R+R64S+N196W+S199G+A222V+E284Q;
T10I+R64S+E96K+N196W+S199G+A222V+E284Q;
D39R+R64S+D90E+E96K+N196W+S199G+A222V+E284Q;
T10I+R64S+E96K+N196W+S199G+A222V;
T10I+D39R+N196W+S199G+A222V+E284Q;

D39R+E96K+N196W+S199G+A222V+E284Q;
D39R+R64S+N196W+S199G+A222V+E284Q;
R64S+E96K+N196W+S199G+A222V+E284Q;
D39R+R64S+N196W+S199G+A222V;
S12*+S13*+V14*+K15*+N16*+I103Y+N196W+S199G+A222V+N233S+T308Y;
S12*+S13*+V14*+K15*+N16*+A43D+I103Y+N196W+S199G+A222V+N233S+T308M;
V9L+S12P+V14I+N16S+A43T+N196W+S199G+A222V;
S12*+S13*+V14*+K15*+N16*+N196W+S199G+A222V;
N28W+N196W+S199G+A222V;
N196W+S199G+A222V+N392W+K417W;
T10I+D39R+E96K+N196W+S199G+A222V;
V9D+R38H+N196W+S199G+A222V+T348K;
S113F+L150Y+N156K+N196W+S199G+A222V;
S113Y+L150Y+N156K+N196W+S199G+A222V;
S113W+L150Y+N156K+N196W+S199G+A222V;
S113F+N156K+N196W+S199G+A222V;
S113Y+N156K+N196W+S199G+A222V;
S113W+N156K+N196W+S199G+A222V;
W138Y+L150V+N196W+S199G+A222V;
W138Y+L150V+D179G+N196W+S199G+A222V;
W138Y+L150V+N196W+S199G+L218W+A222V;
E96K+Q134L+D179S+N196W+S199G+A222V+E284Q;
E96K+Q134L+L150Y+N156R+D179S+N196W+S199G+A222V+E284Q;
E96K+L150Y+N156R+D179S+N196W+S199G+A222V+E284Q;
R38H+E96K+G99N+K101R+Q134L+D179S+N196W+S199G+S221N+A222V;
R38H+E96K+G99N+K101R+Q134L+D179S+N196W+S199G+A222V;
R38H+E96K+G99N+K101R+Q134L+L150Y+N156R+D179S+N196W+S199G+A222V;
R38H+E96K+G99N+K101R+L150Y+N156R+D179S+N196W+S199G+A222V;
L150F+N196W+S199G+A222I;
Q134L+L150F+N156R+N196W+S199G+A222I;
Q134L+L150H+N156R+N196W+S199G+A222I;
Q134L+L150M+N156K+N196W+S199G+A222I;
Q134L+L150Y+N156K+N196W+S199G+A222I+Q457L;
Q134M+L150W+N156K+N196W+S199G+A222I;
Q134W+L150W+N156K+N196W+S199G+A222I;
L150W+L152M+N156K+N196W+S199G+A222I;
S113F+L150W+N156K+N196W+S199G+A222I;
S113Y+L150W+N156K+N196W+S199G+A222I;
L150W+G151W+N156K+N196W+S199G+A222I;
L150W+G151S+N156K+N196W+S199G+A222I;
S113F+L150W+G151S+N156K+N196W+S199G+A222I;
Y67W+W68Y+L150W+N156K+N196W+S199G+A222I;
A43V+L150M+G151F+N156R+N196W+S199G+A222I;
L150M+G151Y+N156R+N196W+S199G+A222I;
L150M+G151W+N156R+N196W+S199G+A222I;
L150M+G151S+N156R+N196W+S199G+A222I+Y534H;
S113F+L150M+G151S+N156R+N196W+S199G+A222I;
Q134L+L150F+N156K+N196W+S199G+A222I;
L150W+G151F+N156K+N196W+S199G+A222I;
L150W+G151Y+N156K+N196W+S199G+A222I;
Y67W+W68Y+L150W+N156K+N196W+S199G+A222I;
G56W+N57P+Y67W+W68Y+L150W+N156K+N196W+S199G+A222I;
K54I+Y67W+W68S+S113G+N196W+S199G+A222V+A382T;
K54I+Y67W+W68S+S113G+D114Q+L150V+N196W+S199G+A222V;
K541+Y67W+W68S+S113G+W138Y+N196W+S199G+A222V;
K54I+Y67W+W68S+S113G+D114Q+W138Y+L150V+N196W+S199G+A222V;
Q134L+N196W+S199G+A222V;
V107T+I108L+H110D+F169H+N196W+S199G+A222V;
N196W+S199G+A222V+N392W+K417W;
V9D+R38H+N196W+S199G+A222V+T348K;
E96H+L150Y+N156R+N196W+S199G+A222V+E284Q;
Q134L+L150Y+N196W+S199G+A222V;
L150Y+N196W+S199G+A222V;
Q134L+L150Y+N196W+S199G+A222V;
L150F+N156R+N196W+S199G+A222V;
L150H+N156R+N196W+S199G+A222V;
Q134L+L150F+N156R+N196W+S199G+A222V;
Q134L+L150H+N156R+N196W+S199G+A222V;
Q134L+L150F+N156K+N196W+S199G+A222V;
Q134L+L150H+N156K+N196W+S199G+A222V;
Q134L+L150Y+N156K+N196W+S199G+A222V;
L150Y+N156K+N196W+S199G+A222V;
Q134L+L150Y+N156K+N196W+S199G+A222V;
Q134W+L150Y+N156K+N196W+S199G+A222V;
Q134M+L150Y+N156K+N196W+S199G+A222V;
Q134M+L150Y+N156K+N196W+S199G+A222V+A466V;
L150Y+L152M+N156K+N196W+S199G+A222V;
L150S+N196W+S199G+A222V;
N196W+S199G+A222V+N281S;
Y67T+N196W+S199G+A222V;
Q71N+N196W+S199G+A222V;
Q71N+A94D+N196W+S199G+A222V;
N196W+S199G+L218F+A222V;
N196W+S199G+L218W+A222V;
N196W+S199G+A222V+T278W;
N196W+S199G+A222V+T278W+T459M;
N196W+S199G+A222V+T278Y;
N196W+S199G+A222V+S275N;
N196W+S199G+A222V+S275L;
N196W+S199G+A222V+S335Q;
N196W+S199G+A222V+S335K;
N196W+S199G+A222V+S335R;
N196W+S199G+L218W+A222V+S335K;
N196W+S199G+L218W+A222V+S335Q;
Y67W+N196W+S199G+A222V;
N196W+S199G+A222V+N281Q;
L150M+N156R+N196W+S199G+A222V;
Q134L+L150M+N156R+N196W+S199G+A222V;
Q134L+L150M+N156K+N196W+S199G+A222V;
D39R+N196W+S199G+A222V+N281Q+E284Q;
D39R+N196W+S199G+A222V+E284Q+Q479QP;
D39R+Y70F+N196W+S199G+A222V+E284Q;
N28W+D39R+N196W+S199G+A222V+E284Q;
D39R+N196W+S199G+N207W+A222V+E284Q;
E1*+T2*+A3*+N4*+K5*+S6*+N7*+K8*+D39R+N196W+S199G+N207W+A222V+E284Q;
N196W+N207W;
N196W+N207W+E284Q;

E1*+T2*+A3*+N4*+K5*+S6*+N7*+K8*+N196W+N207W+E284Q;
L150Y+N196W+S199G+A222V;
E1*+T2*+A3*+N4*+K5*+S6*+N7*+K8*+L150Y+N196W+S199G+A222V;
E96K+K101R+L150M+N156R+D179S+N196W+S199G+N207W+T208N+A222V;
E1*+T2*+A3*+N4*+K5*+S6*+N7*+K8*+E96K+K101R+L150M+N156R+D179S+N196W+S199G+T208N+A222V;
Q134L+L150H+N156R+N196W+S199G+A222I+E284Q;
E1*+T2*+A3*+N4*+K5*+S6*+N7*+K8*+Q134L+L150H+N156R+N196W+S199G+A222I;
E1*+T2*+A3*+N4*+K5*+S6*+N7*+K8*+Q134L+L150H+N156R+N196W+S199G+N207W+A222I+E284Q;
E96K+D179S+N196W+S199G+A222V+E284Q;
E1*+T2*+A3*+N4*+K5*+S6*+N7*+K8*+E96K+D179S+N196W+S199G+A222V+E284Q;
R64S+E96K+N196W+S199G+N207W+A222V;
N28W+D39R+N196W+S199G+N207W+A222V+E284Q;
D39R+N196W+S199G+A222V+E284Q;
D39R+N196W+S199G+N207W+A222V+E284Q;
E1*+T2*+A3*+N4*+K5*+S6*+N7*+K8*+D39R+N196W+S199G+A222V+E284Q;
E1*+T2*+A3*+N4*+K5*+S6*+N7*+K8*+N196W+N207W+E511D;
L150Y+N196W+S199G+N207W+A222V;
E96K+K101R+L150M+N156R+D179S+N196W+S199G+T208N+A222V;
E96K+K101R+L150M+N156R+D179S+N196W+S199G+T208N+A222V+E284Q;
E1*+T2*+A3*+N4*+K5*+S6*+N7*+K8*+E96K+K101R+L150M+N156R+D179S+N196W+S199G+N207W+T208N+A222V+E284Q;
Q134L+L150H+N156R+N196W+S199G+A222I;
N28W+E96K+D179S+N196W+S199G+A222V+E284Q;
R64S+E96K+N196W+S199G+A222V;
R64S+E96K+N196W+S199G+A222V+E284Q;
E1*+T2*+A3*+N4*+K5*+S6*+N7*+K8*+R64S+E96K+N196W+S199G+A222V;

and wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 1, SEQ ID NO: 2, SEQ ID NO: 3, or SEQ ID NO: 4.

Embodiment 10. The variant of embodiment 9, wherein the alpha-amylase further comprises a C-terminal deletion, particularly H626*.

Embodiment 11. The variant alpha-amylase of any of embodiments 1-5, comprising a combination of alterations selected from:

N28W+H626*;
S199G+H626*;
N196W+V599W+H626*;
N196W+H550Y+P605S+H626*;
N196W+A545P+T576Y+H626*;
N196W+K549Y+G560P+H626*;
I108P+Y183I+N196W+I205Y+H626*;
N196W+R323K+H626*;
N196W+D283P+H626*;
W138Y+N196W+H626*;
L150W+H626*;
N196W+N392W+K417W+H626*;
N196W+N392R+K417W+H626*;
N196W+K549*+H550*+D551*+H626*;
N196W+P580*+E581*+N582*+H626*;
N196W+F592FK+H626*;
N28W+N196W+N207W+S386D+N603W+H626*;
R38Y+N196W+H626*;
N196W+H259Y+H626*;
N196W+Q412W+H626*;
N196W+F212W+H626*;
N196W+V599W+H626*;
N196W+H550Y+P605S+H626*;
N196W+H550Y+K589F+H626*;
N196W+H550Y+D608Y+H626*;
N196W+M574W+L614W+H626*;
N196W+G533H+M574W+L614W+H626*;
N196W+V543P+N570H+H626*;
N196W+G533H+Y575W+L614W+H626*;
N196W+A545P+T576Y+H626*;
N196W+A566P+T578Y+H626*;
N196W+K549Y+G560P+H626*;
N196W+A566P+L577Y+H626*;
N196W+I547Y+G560P+H626*;
N196W+M574MW+H626*;
N196W+K549*+H550*+D551*+M574MW+P580*+E581*+N582*+F592FK+H626*;
N196W+L614W+G619W+H626*;
N28W+I108P+N196W+N207W+S386D+A466V+Q542K+N603W+H626*;
N28W+I108P+N196W+N207W+S386D+N603W+H626*;
N196W+D282P+D283*+H626*;
W138Y+N196W+H626*;
N28W+N196W+N207W+S386D+N603W+H626*;
N196W+S388W+A424P+H626*;
N196W+S388W+A424P+L489Q+H626*;
A117T+N196W+H550Y+D608Y+H626*;
N196W+Q457R+Y575W+L614W+H626*;
N196W+$199G;
N196W+A222V;
N196W+A222E;
N196W+A222I;
S199G+A222V;
S199G+A222E;
S199G+A222I;
N196W+S199G+A222I;
Q134L+H626*;
L150W+N156K+N196W+S199G+A222V;
L150Y+N156K+N196W+S199G+A222I;
L150W+N196W+S199G+A222I+A428S;
L150F+N156K+N196W+S199G+A222I;
L150Y+N156R+N196W+A222V;
L150M+N156R+N196W+S199G+A222I;
L150M+N156R+N196W+A222V;
L150Y+N156R+N196W+S199G+A222V;
L150M+N156K+N196W+S199G+A222V;
L150Y+N156R+N196W+A222I;
L150H+N156R+N196W+S199G+A222I;
L150H+N156K+N196W+A222V;
L150W+N156R+N196W+A222I;
L150F+N156R+N196W+A222I;
L150F+N156K+N196W+S199G+A222V;
L150H+N156K+N196W+S199G+A222V;
L150F+N156R+S199G+A222I;
L150M+N156K+N196W+A222V;

L150W+N156K+N196W+S199G+A222I;
N156K+N196W+S199G+A222V;
L150Y+N156R+S199G+A222I;
L150M+N156R+S199G+A222I;
L150W+N156K+S199G+A222V;
L150W+N156R+N196W+S199G+A222V;
L150Y+N156R+N196W;
N156K+N196W+A222V;
N156K+N196W+S199G;
N156R+S199G+A222V;
S113H+N196W+S199G+A222V;
Q71E+S113H+N196W+S199G+A222V;
N196W+S199G+A222V+D283A;
N196W+S199G+A222V+D283P;
W142E+D193SQY+N196W+S199G+A222V+R224K;
E96K+K101R+L150W+N156R+D179S+N196W+S199G+T208N+A222V;
E96K+K101R+L150Y+N156R+D179S+N196W+S199G+T208N+A222V+E284Q;
E96K+K101R+L150M+N156R+D179S+N196W+S199G+T208N+A222V+E284Q;
S113Q+Q134E+N196W+S199G+A222V;
S113D+Q134N+N196W+S199G+A222V;
S113F+N196W+S199G+A222V;
E171Q+N196W+S199G+N204D+A222V;
N196W+S199G+A222V+H241N+S245N+T278N+E284Q+E285V;
N196W+S199G+A222V+S394K+A414K+K417Y;
N196W+S199G+A222V+E359Y+S394K+K396S+A414K+K417Y;
R38H+E96K+G99N+K101R+D179S+N196W+S199G+A222V;
R38H+E96K+G99N+K101R+D179S+N196W+S199G+A222V+E284Q;
V107T+H110D+N196W+S199G+A222V;
Q134T+L150Y+N196W+S199G+A222V;
S113F+L150W+N196W+S199G+A222V;
S113F+L150Y+N196W+S199G+A222V;
E96K+K101R+N156R+D179S+N196W+S199G+T208N+A222V;
E96K+K101R+L150Y+N156R+D179S+N196W+S199G+T208N+A222V;
E96K+K101R+L150M+N156R+D179S+N196W+S199G+T208N+A222V;
E96K+K101R+N156R+D179S+N196W+S199G+T208N+A222V+E284Q;
E96K+K101R+L150W+N156R+D179S+N196W+S199G+T208N+A222V+E284Q;
N28R+Q86R+N196W+S199G+A222V;
N28R+Q86R+K89R+N196W+S199G+A222V;
G56P+N196W+S199G+S209L+A222V;
E96K+N196W+S199G+A222V;
T10I+N196W+S199G+A222V;
D39R+N196W+S199G+A222V;
R64S+N196W+S199G+A222V;
T10I+D39R+R64S+N196W+S199G+A222V;
T10I+D39R+N196W+S199G+A222V;
D39R+E96K+N196W+S199G+A222V;
R64S+D90E+E96K+N196W+S199G+A222V;
R38H+D39R+E96K+G99N+K101R+D179S+N196W+S199G+A222V;
R38H+R64S+E96K+G99N+K101R+D179S+N196W+S199G+A222V;
T10I+R38H+R64S+E96K+G99N+K101R+D179S+N196W+S199G+A222V;
T10I+R38H+R64S+D90E+E96K+G99N+K101R+D179S+N196W+S199G+A222V;
T10I+R38H+D39R+E96K+G99N+K101R+D179S+N196W+S199G+A222V;
R38H+D39R+R64S+E96K+G99N+K101R+D179S+N196W+S199G+A222V;
E96K+N196W+S199G+A222V+E284Q;
T10I+N196W+S199G+A222V+E284Q;
D39R+N196W+S199G+A222V+E284Q;
R64S+N196W+S199G+A222V+E284Q;
T10I+D39R+E96K+N196W+S199G+A222V+E284Q;
D193SQY+N196W+S199G+A222V;
Q134T+N196W+S199G+A222V;
L1741+N196W+S199G+T208N+A222V;
Y183F+N196W+S199G+T208S+A222V;
N127D+N156R+N196W+S199G+A222V;
Q134T+L150W+N196W+S199G+A222V;
N57P+N196W+S199G+A222V;
N196W+S199G+Q200W+A222V;
T10I+D39R+R64S+E96K+N196W+S199G+A222V+E284Q;
T10I+D39R+R64S+N196W+S199G+A222V+E284Q;
T10I+R64S+E96K+N196W+S199G+A222V+E284Q;
D39R+R64S+D90E+E96K+N196W+S199G+A222V+E284Q;
T10I+R64S+E96K+N196W+S199G+A222V;
T10I+D39R+N196W+S199G+A222V+E284Q;
D39R+E96K+N196W+S199G+A222V+E284Q;
D39R+R64S+N196W+S199G+A222V+E284Q;
R64S+E96K+N196W+S199G+A222V+E284Q;
D39R+R64S+N196W+S199G+A222V;
S12*+S13*+V14*+K15*+N16*+I103Y+N196W+S199G+A222V+N233S+T308Y;
S12*+S13*+V14*+K15*+N16*+A43D+I103Y+N196W+S199G+A222V+N233S+T308M;
V9L+S12P+V14I+N16S+A43T+N196W+S199G+A222V;
S12*+S13*+V14*+K15*+N16*+N196W+S199G+A222V;
N28W+N196W+S199G+A222V;
N196W+S199G+A222V+N392W+K417W;
T10I+D39R+E96K+N196W+S199G+A222V;
V9D+R38H+N196W+S199G+A222V+T348K;
S113F+L150Y+N156K+N196W+S199G+A222V+H626*;
S113Y+L150Y+N156K+N196W+S199G+A222V+H626*;
S113W+L150Y+N156K+N196W+S199G+A222V+H626*;
S113F+N156K+N196W+S199G+A222V+H626*;
S113Y+N156K+N196W+S199G+A222V+H626*;
S113W+N156K+N196W+S199G+A222V+H626*;
W138Y+L150V+N196W+S199G+A222V+H626*;
W138Y+L150V+D179G+N196W+S199G+A222V+H626*;
W138Y+L150V+N196W+S199G+L218W+A222V+H626*;
E96K+Q134L+D179S+N196W+S199G+A222V+E284Q+H626*;
E96K+Q134L+L150Y+N156R+D179S+N196W+S199G+A222V+E284Q+H626*;
E96K+L150Y+N156R+D179S+N196W+S199G+A222V+E284Q+H626*;
R38H+E96K+G99N+K101R+Q134L+D179S+N196W+S199G+S221N+A222V+H626*;
R38H+E96K+G99N+K101R+Q134L+D179S+N196W+S199G+A222V+H626*;
R38H+E96K+G99N+K101R+Q134L+L150Y+N156R+D179S+N196W+S199G+A222V+

H626*;
R38H+E96K+G99N+K101R+L150Y+N156R+D179S+N196W+S199G+A222V+H626*;
L150F+N196W+S199G+A222I+H626*;
Q134L+L150F+N156R+N196W+S199G+A222I+H626*;
Q134L+L150H+N156R+N196W+S199G+A222I+H626*;
Q134L+L150M+N156K+N196W+S199G+A222I+H626*;
Q134L+L150Y+N156K+N196W+S199G+A222I+Q457L+H626*;
Q134M+L150W+N156K+N196W+S199G+A222I+H626*;
Q134W+L150W+N156K+N196W+S199G+A222I+H626*;
L150W+L152M+N156K+N196W+S199G+A222I+H626*;
S113F+L150W+N156K+N196W+S199G+A222I+H626*;
S113Y+L150W+N156K+N196W+S199G+A222I+H626*;
L150W+G151W+N156K+N196W+S199G+A222I+H626*;
L150W+G151S+N156K+N196W+S199G+A222I+H626*;
S113F+L150W+G151S+N156K+N196W+S199G+A222I+H626*;
Y67W+W68Y+L150W+N156K+N196W+S199G+A222I+H626*;
A43V+L150M+G151F+N156R+N196W+S199G+A222I;
L150M+G151Y+N156R+N196W+S199G+A222I;
L150M+G151W+N156R+N196W+S199G+A222I;
L150M+G151S+N156R+N196W+S199G+A222I+Y534H;
S113F+L150M+G151S+N156R+N196W+S199G+A222I;
Q134L+L150F+N156K+N196W+S199G+A222I+H626*;
L150W+G151F+N156K+N196W+S199G+A222I+H626*;
L150W+G151Y+N156K+N196W+S199G+A222I+H626*;
Y67W+W68Y+L150W+N156K+N196W+S199G+A222I;
G56W+N57P+Y67W+W68Y+L150W+N156K+N196W+S199G+A222I+H626*;
K54I+Y67W+W68S+S113G+N196W+S199G+A222V+A382T+H626*;
K541+Y67W+W68S+S113G+D114Q+L150V+N196W+S199G+A222V+H626*;
K541+Y67W+W68S+S113G+W138Y+N196W+S199G+A222V+H626*;
K54I+Y67W+W68S+S113G+D114Q+W138Y+L150V+N196W+S199G+A222V+H626*;
Q134L+N196W+S199G+A222V+H626*;
V107T+I108L+H110D+F169H+N196W+$199G+A222V+H626*;
N196W+S199G+A222V+N392W+K417W+H626*;
V9D+R38H+N196W+S199G+A222V+T348K+H626*;
E96H+L150Y+N156R+N196W+S199G+A222V+E284Q+H626*;
Q134L+L150Y+N196W+S199G+A222V+H626*;
L150Y+N196W+S199G+A222V+H626*;
Q134L+L150Y+N196W+S199G+A222V+H626*;
L150F+N156R+N196W+S199G+A222V+H626*;
L150H+N156R+N196W+S199G+A222V+H626*;
Q134L+L150F+N156R+N196W+S199G+A222V+H626*;
Q134L+L150H+N156R+N196W+S199G+A222V+H626*;
Q134L+L150F+N156K+N196W+S199G+A222V+H626*;
Q134L+L150H+N156K+N196W+S199G+A222V+H626*;
Q134L+L150Y+N156K+N196W+S199G+A222V+H626*;
L150Y+N156K+N196W+S199G+A222V+H626*;
Q134L+L150Y+N156K+N196W+S199G+A222V+H626*;
Q134W+L150Y+N156K+N196W+S199G+A222V+H626*;
Q134M+L150Y+N156K+N196W+S199G+A222V+H626*;
Q134M+L150Y+N156K+N196W+S199G+A222V+A466V+H626*;
L150Y+L152M+N156K+N196W+S199G+A222V+H626*;
L150S+N196W+S199G+A222V+H626*;
N196W+S199G+A222V+N281S+H626*;
Y67T+N196W+S199G+A222V+H626*;
Q71N+N196W+S199G+A222V+H626*;
Q71N+A94D+N196W+S199G+A222V+H626*;
N196W+S199G+L218F+A222V+H626*;
N196W+S199G+L218W+A222V+H626*;
N196W+S199G+A222V+T278W+H626*;
N196W+S199G+A222V+T278W+T459M+H626*;
N196W+S199G+A222V+T278Y+H626*;
N196W+S199G+A222V+S275N+H626*;
N196W+S199G+A222V+S275L+H626*;
N196W+S199G+A222V+S335Q+H626*;
N196W+S199G+A222V+S335K+H626*;
N196W+S199G+A222V+S335R+H626*;
N196W+S199G+L218W+A222V+S335K+H626*;
N196W+S199G+L218W+A222V+S335Q+H626*;
Y67W+N196W+S199G+A222V+H626*;
N196W+S199G+A222V+N281Q+H626*;
L150M+N156R+N196W+S199G+A222V+H626*;
Q134L+L150M+N156R+N196W+S199G+A222V+H626*;
Q134L+L150M+N156K+N196W+S199G+A222V+H626*;
D39R+N196W+S199G+A222V+N281Q+E284Q;
D39R+N196W+S199G+A222V+E284Q+Q479QP;
D39R+Y70F+N196W+S199G+A222V+E284Q;
N28W+D39R+N196W+S199G+A222V+E284Q;
D39R+N196W+S199G+N207W+A222V+E284Q;
E1*+T2*+A3*+N4*+K5*+S6*+N7*+K8*+D39R+N196W+S199G+N207W+A222V+E284Q+H626*;
N196W+N207W;
N196W+N207W+E284Q;
E1*+T2*+A3*+N4*+K5*+S6*+N7*+K8*+N196W+N207W+E284Q;
L150Y+N196W+S199G+A222V+H626*;
E1*+T2*+A3*+N4*+K5*+S6*+N7*+K8*+L150Y+N196W+S199G+A222V;
E96K+K101R+L150M+N156R+D179S+N196W+S199G+N207W+T208N+A222V;
E1*+T2*+A3*+N4*+K5*+S6*+N7*+K8*+E96K+K101R+L150M+N156R+D179S+N196W+S199G+T208N+A222V;

Q134L+L150H+N156R+N196W+S199G+A222I+E284Q+H626*;
E1*+T2*+A3*+N4*+K5*+S6*+N7*+K8*+Q134L+L150H+N156R+N196W+S199G+A222I+H626*;
E1*+T2*+A3*+N4*+K5*+S6*+N7*+K8*+Q134L+L150H+N156R+N196W+S199G+N207W+A222I+E284Q;
E96K+D179S+N196W+S199G+A222V+E284Q+H626*;
E1*+T2*+A3*+N4*+K5*+S6*+N7*+K8*+E96K+D179S+N196W+S199G+A222V+E284Q;
R64S+E96K+N196W+S199G+N207W+A222V;
N28W+D39R+N196W+S199G+N207W+A222V+E284Q;
D39R+N196W+S199G+A222V+E284Q+H626*;
D39R+N196W+S199G+N207W+A222V+E284Q;
E1*+T2*+A3*+N4*+K5*+S6*+N7*+K8*+D39R+N196W+S199G+A222V+E284Q;
E1*+T2*+A3*+N4*+K5*+S6*+N7*+K8*+N196W+N207W+E511D;
L150Y+N196W+S199G+N207W+A222V;
E96K+K101R+L150M+N156R+D179S+N196W+S199G+T208N+A222V+H626*;
E96K+K101R+L150M+N156R+D179S+N196W+S199G+T208N+A222V+E284Q;
E1*+T2*+A3*+N4*+K5*+S6*+N7*+K8*+E96K+K101R+L150M+N156R+D179S+N196W+S199G+N207W+T208N+A222V+E284Q+H626*;
Q134L+L150H+N156R+N196W+S199G+A222I;
N28W+E96K+D179S+N196W+S199G+A222V+E284Q;
R64S+E96K+N196W+S199G+A222V+H626*;
R64S+E96K+N196W+S199G+A222V+E284Q;
E1*+T2*+A3*+N4*+K5*+S6*+N7*+K8*+R64S+E96K+N196W+S199G+A222V;

and wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 1, SEQ ID NO: 2, SEQ ID NO: 3, or SEQ ID NO: 4.

Embodiment 12. The variant of any of embodiments 1-8, wherein the alpha-amylase comprises combinations of alterations selected from:

S199G+H626*;
N196W+H626*
N196W+S199G+A222V+H 626*;
N196W+N207W+H626*;
L150Y+N196W+S199G+A222V
E96K+D179S+N196W+S199G+A222V+E284Q;
R64S+E96K+N196W+S199G+A222V;

and wherein the variant has alpha-amylase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 1, SEQ ID NO: 2, SEQ ID NO: 3, or SEQ ID NO: 4.

Embodiment 13. The variant of any of embodiments 1-12, wherein increased pH stability at pH 4.0 can be determined as % residual alpha-amylase activity (% RA) after incubation of the variant amylase at pH 4.0, 32° C., for 18-24 hours.

Embodiment 14. The variant of any of embodiments 1-12, wherein increased pH stability at pH 4.0 can be determined as residual alpha-amylase activity after incubation of the variant amylase at pH 4.0, 32° C., for 96 hours, and calculation of enzyme half-life in hours.

Embodiment 15. The variant of any of embodiments 1-14, wherein half-life is increased compared to the parent amylase of SEQ ID NO: 1, 2, 3, or 4 of at least a factor 1.2, 1.3, 1.4, 1.5, 2.0, 2.5, 3.0, 3.5, 4.0, 4.5, 5.0, 6.0, 7.0, such as at least 8.0.

Embodiment 16. The variant of any of embodiments 1-10, further comprising a substitution corresponding to K8N.

Embodiment 17. A variant alpha-amylase of any of the preceding embodiments, comprising at least the catalytic domain, comprised in amino acids 12-438 of SEQ ID NO: 1, wherein the variant has alpha-amylase activity and wherein the catalytic domain has at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 1, and wherein the variant optionally has a CBM.

Embodiment 18. The variant of any of embodiments 1-17, wherein the linker and/or a carbohydrate binding module, CBM, has been replace with a heterologous CBM.

Embodiment 19. The variant of embodiment 18, wherein the CBM comprises amino acids 527-626 of SEQ ID NO: 1, and amino acids 439-526 comprises a linker region.

Embodiment 20. The variant of any of embodiments 17-19, wherein the heterologous CBM is selected from a heterologous CBM belonging to Family 20, 21, 25, 26, 34, 41 or 48.

Embodiment 21. The variant of embodiment 20, wherein the CBM is a Family 20 CBM.

Embodiment 22. The variant of any of the embodiments 18-21, wherein the CBM is selected from the group consisting of:

i) a polypeptide of SEQ ID NO: 14, or a polypeptide having at least 65%, at least 70%, at least 75%, at least 80%, at least 85%, at least 90%, at least 95%, at least 96%, at least 97%, at least 98%, or at least 99% sequence identity to the polypeptide of SEQ ID NO: 14;

ii) a polypeptide of SEQ ID NO: 15, or a polypeptide having at least 65%, at least 70%, at least 75%, at least 80%, at least 85%, at least 90%, at least 95%, at least 96%, at least 97%, at least 98%, or at least 99% sequence identity to the polypeptide of SEQ ID NO: 15;

iii) a polypeptide of SEQ ID NO: 16, or a polypeptide having at least 65%, at least 70%, at least 75%, at least 80%, at least 85%, at least 90%, at least 95%, at least 96%, at least 97%, at least 98%, or at least 99% sequence identity to the polypeptide of SEQ ID NO: 16;

iv) a polypeptide of SEQ ID NO: 17, or a polypeptide having at least 65%, at least 70%, at least 75%, at least 80%, at least 85%, at least 90%, at least 95%, at least 96%, at least 97%, at least 98%, or at least 99% sequence identity to the polypeptide of SEQ ID NO: 17;

v) a polypeptide of SEQ ID NO: 18, or a polypeptide having at least 65%, at least 70%, at least 75%, at least 80%, at least 85%, at least 90%, at least 95%, at least 96%, at least 97%, at least 98%, or at least 99% sequence identity to the polypeptide of SEQ ID NO: 18; and vi) a polypeptide of SEQ ID NO: 19, or a polypeptide having at least 65%, at least 70%, at least 75%, at least 80%, at least 85%, at least 90%, at least 95%, at least 96%, at least 97%, at least 98%, or at least 99% sequence identity to the polypeptide of SEQ ID NO: 19.

Embodiment 23. The variant of any of embodiments 18-22, wherein the linker is between 1 to 100 amino acids.

Embodiment 24. An isolated polynucleotide encoding the variant of any one of embodiments 1-23.

Embodiment 25. A nucleic acid construct or expression vector comprising the polynucleotide of embodiment 24 operably linked to one or more control sequences that direct the production of the polypeptide in an expression host.

Embodiment 26. A recombinant host cell comprising the polynucleotide of embodiment 24 operably linked to one or more heterologous control sequences that direct the production of the polypeptide.

Embodiment 27. The host cell according to embodiment 26, wherein the host cell is a yeast cell, particularly a *Saccharomyces*, such as *Saccharomyces cerevisiae.*

Embodiment 28. A method of producing a variant alpha-amylase of any of embodiments 1-23, comprising: cultivating the recombinant host cell of embodiment 26 under conditions suitable for expression of the variant; and optionally recovering the variant.

Embodiment 29. A composition comprising the variant alpha-amylase of any of embodiments 1-23.

Embodiment 30. The composition of embodiment 29 further comprising at least one glucoamylase.

Embodiment 31. A whole broth formulation or cell culture composition comprising the variant alpha-amylase of any of embodiments 1-23.

Embodiment 32. The composition of embodiment 29, further comprising a surfactant.

Embodiment 33. The composition of embodiment 32, wherein the composition comprises a surfactant or surfactant system wherein the surfactant can be selected from nonionic surfactants, anionic surfactants, cationic surfactants, ampholytic surfactants, zwitterionic surfactants, semi-polar nonionic surfactants and mixtures thereof.

Embodiment 34. The composition of embodiment 33, wherein the composition comprises an anionic surfactant, in particular linear alkylbenzene sulfonate (LAS) and/or alcohol ethoxysulfate (AEOS).

Embodiment 35. The composition of embodiment 33, wherein the composition comprises a nonionic surfactant, such as alcohol ethoxylate (AEO).

Embodiment 36. The composition of any of embodiments 32-35, wherein the composition comprises one or more anionic and/or one or more nonionic surfactants.

Embodiment 37. The composition of any of embodiments 32-36, wherein the composition comprises one or more of surfactants, in particular linear alkylbenzenesulfonic acid (LAS), sodium laureth sulfate (SLES) and/or alcohol ethoxylate (AEO).

Embodiment 38. A use of a variant alpha-amylase of any of embodiments 1-23 for production of syrup and/or a fermentation product.

Embodiment 39. A process of producing a fermentation product from starch-containing material comprising the steps of: (a) liquefying starch-containing material above the initial gelatinization temperature of said starch-containing material in the presence of an alpha amylase; (b) saccharifying the liquefied material; and (c) fermenting with a fermenting organism; wherein step (b) is carried out in the presence of at least a variant alpha-amylase of any of embodiments 1-23, and optionally a glucoamylase.

Embodiment 40. The process of embodiment 39, wherein step (b) and step (c) are carried out simultaneously.

Embodiment 41. The process of any of the embodiments 39-40, wherein the host cell of any of embodiments 26-27 is applied as the fermenting organism.

Embodiment 42. The process of embodiment 39, wherein the host cell further is expressing a glucoamylase.

Embodiment 43. The process according to any of embodiments 41-42, wherein the host cell further is expressing an alpha-amylase derived from a strain of the genus *Rhizomucor*, preferably a strain of *Rhizomucor pusillus*, such as a *Rhizomucor pusillus* alpha-amylase hybrid having a linker and starch-binding domain from an *Aspergillus niger* glucoamylase.

Embodiment 44. The process of embodiment 43, wherein the further alpha-amylase expressed by the host cell in fermentation is selected from the group consisting of:

(i) an alpha-amylase comprising the polypeptide of SEQ ID NO: 12;

(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 12.

Embodiment 45. The process of embodiment 44, wherein the further alpha-amylase comprises one or more of the following substitutions: G128D, D143N, preferably G128D+D143N, using SEQ ID NO: 12 for numbering.

Embodiment 46. The process of any of embodiments 39-45, wherein the fermenting organism or host cell is a yeast cell, particularly a *Saccharomyces* cell, such as *Saccharomyces cerevisiae.*

Embodiment 47. The process of any of embodiments 39-46, wherein the fermentation product is an alcohol, such as ethanol.

Embodiment 48. The process of any of embodiments 39-47, wherein the starch-containing material is corn.

Embodiment 49. A process of producing a syrup product from starch-containing material, comprising the step of: (a) liquefying starch-containing material at a temperature above the initial gelatinization temperature of said starch-containing material in the presence of an alpha-amylase; (b) saccharifying the liquefied material in the presence of at least a variant alpha-amylase of any of the embodiments 1-23, and optionally a glucoamylase.

Embodiment 50. The process of embodiment 49, wherein step a) is carried out using at least a variant alpha-amylase of any of embodiments 1-22, and a second alpha-amylase.

Embodiment 51. The variant alpha-amylase according to any of embodiments 1-23, wherein the variant is isolated.

Embodiment 52. A transgenic plant, plant part or plant cell comprising the variant alpha-amylase of any of embodiments 1-23.

The present invention is further described by the following examples that should not be construed as limiting the scope of the invention.

EXAMPLES

Strains

*Bacillus amyloliquefaciens* strain used in the examples was isolated from soil in Virginia in the USA in 2011.

*Saccharomyces cerevisiae* strain MBG5012 (deposited under Accession No. NRRL Y67700 at the *Agricultural*

*Research* Service Patent Culture Collection 5 (NRRL), USA, and described in WO19/161227.

Materials and Methods

Material:

TB-GLY media

MSA-SUB-FS-057

| Raw material | Amount | |
|---|---|---|
| Tryptone | 13.3 | g |
| Yeast extract | 26.6 | g |
| Glycerol anhydrous pure | 5.5 | g |
| Ion exchanged water up to | 1000 | ml |

The 100 mM BR buffer is prepared from a 1M BR stock by adding 50 μL of a 2M CaCl2 solution, and 1000 μL of a 10% Brij35 stock solution to 100 mL 1M stock, and 900 mL milliQ water to a concentration of 0.1 mM CaCl2 and 0.01% Brij35.

The 1M BR stock is prepared by dissolving 136 g Sodium acetate dihydrate (CAS 6131-90-4), 142 g Disodium hydrogen phosphate (CAS 7558-79-4), and 61.8 g Boric acid (CAS 10043-35-3) in milliQ water to a total volume of 1L.

After dilution, the pH of the 100 mM BR buffer is adjusted to pH 4 or PH 7 by adding HCL or NaOH as needed.

Assays:

pNP-G7 Alpha-Amylase Activity Assay

The alpha-amylase activity may be determined by a method employing the G7-pNP substrate. G7-pNP which is an abbreviation for 4,6-ethylidene (G)-p-nitrophenyl($G_1$)-α, D-maltoheptaoside, a blocked oligosaccharide which can be cleaved by an endo-amylase, such as an alpha-amylase. Following the cleavage, the alpha-Glucosidase included in the kit digest the hydrolyzed substrate further to liberate a free PNP molecule which has a yellow color and thus can be measured by visible spectrophotometry at λ=405 nm (400-420 nm.). Kits containing G7-pNP substrate and alpha-Glucosidase is manufactured by Roche/Hitachi (cat. No.11876473) or Sigma-Aldrich (Catalog number MAK009).

Reagents:

The G7-pNP substrate from this kit contains 22 mM 4,6-ethylidene-G7-pNP and 52.4 mM HEPES (2-[4-(2-hydroxyethyl)-1-piperazinyl]-ethanesulfonic acid), pH 7.0).

The alpha-Glucosidase reagent contains 52.4 mM HEPES, 87 mM NaCl, 12.6 mM MgCl2, 0.075 mM $CaCl_2$), ≥4 kU/L alpha-glucosidase).

The substrate working solution is made by mixing 1 mL of the alpha-Glucosidase reagent with 0.2 mL of the G7-pNP substrate. This substrate working solution is made immediately before use.

Dilution buffer: 50 mM MOPS, 0.05% (w/v) Triton λ100 (polyethylene glycol p-(1,1,3,3-tetramethylbutyl)-phenyl ether ($C_{14}H_{22}O(C_2H_4O)_n$ (n=9-10))), 1 mM CaCl2, pH8.0.

Procedure:

The amylase sample to be analyzed is diluted in dilution buffer to ensure the pH in the diluted sample is 7. The assay is performed by transferring 20 μl diluted enzyme samples to 96 well microtiter plate and adding 80 μl substrate working solution. The solution is mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

Amylase pH 4 Stability Screening Assay

Sample Preparation

The expression clones are grown between 18 hours and 24 hours under good expression conditions in TB-GLY medium in 2.2 mL deep-well plates at 37° C. at 700 RPM in a TH 15 TiMix microplate shaker from Edmund Bühler Gmbh.

After fermentation, the samples can be spun down to reduce the number of cells in the supernatant.

Sample Incubation

From each variant supernatant sample, a subsample was incubated at pH 4 and 37° C. for 18 to 24 hours in a 100 mM BR-buffer adjusted to pH 4 (hereafter called the stressed sample), while an equivalent subsample was stored at pH 7 at 4° C. or below in a 100 mM BR buffer adjusted to pH 7 (hereafter called the unstressed sample). Incubation was performed in a 96-well Nunc MicroWell polypropylene plate (Sigma Aldrich P6866) sealed with an Agilent Plate-Loc plate-sealer.

10 μL of variant supernatant sample was diluted 10 times by mixing it into 90 μl buffer for incubation.

Sample Analysis

After incubation, the samples were prediluted 20 before activity was measured. Amylase activity was determined using a G7-pNP kit (Sigma-Aldrich Catalog number MAK009). Sample dilution was performed in the pH 7 BR buffer. A further dilution was done to a total in-assay dilution of 1000×, by mixing 10 μL of diluted sample with 40 μL G7 substrate in a 380-well PerkinElmer SpectraPlate reader-plate.

The stressed and unstressed sample of a given variant were read on the same reader-plate. The enzyme activity was evaluated according to the G7 assay protocol. The solution was mixed and pre-incubated 1 minute at room temperature and absorption was measured every 20 sec. over 30 minutes at OD 405 nm, and the highest measured slope was used as a measure of enzyme activity. A well with no enzyme sample added was used as control, and any slope in that well was subtracted from all the measured activities on the same plate.

Data Evaluation—Determination of Half-Life

For a given variant, the enzyme activity of the stressed sample was divided by the enzyme activity of the unstressed sample, to compute residual activity. From this, the half-life in hours of the enzyme candidate is computed as the negative of the incubation-time in hours divided by log2 of the residual activity.

Example 1: Cloning and Expression of the Parent Wild Type *Bacillus amyloliquefaciens* Alpha-Amylase and Variants Thereof The strain *Bacillus amyloliquefaciens* was isolated from soil in Virginia in the USA in 2011. Chromosomal DNA from the strain was subjected to full genome sequencing using Illumina technology. The GH13 subfamily 28 amylase was identified in the genome by analysing for glycosyl hydrolase domains (according to the CAZY definition).

A linear integration vector-system was used for the expression cloning of the amylase from *Bacillus amyloliquefaciens*. The linear integration construct was a PCR fusion product made by fusion of the gene between two *Bacillus subtilis* homologous chromosomal regions along with a strong promoter and a chloramphenicol resistance marker. The fusion was made by SOE PCR (Horton, R. M., Hunt, H. D., Ho, S. N., Pullen, J. K. and Pease, L. R. (1989) Engineering hybrid genes without the use of restriction enzymes, gene splicing by overlap extension Gene 77:61-68). The SOE PCR method is also described in patent application WO 2003/095658. The gene was expressed under the control of a triple promoter system (as described in WO 1999/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The gene coding for chloramphenicol acetyl-transferase was used as marker (described in e.g. Diderichsen, B.; Poulsen, G. B.; Joergensen, S. T. 1993, Plasmid, "A useful cloning vector for *Bacillus subtilis*" 30:312. The final gene construct was integrated in the *Bacillus* chromosome by homologous recombination into the pectate lyase locus.

The gene encoding the amylase was amplified from chromosomal DNA of the strains with gene specific primers containing overhang to the two flanking vector fragments. The amylase was expressed with a *Bacillus clausii* secretion signal (amino acids 1-27 of SEQ ID NO: 6) replacing the genes native secretion signal and with a histidine tag of 6 histidines fused directly to the C-terminal of the protein. The polynucleotide sequence used for expression was included herein as SEQ ID NO: 5. The upstream and downstream vector fragments were amplified from genomic DNA of the strain MB1361 (based on strain PL3598 described in patent application WO 2003095658). The 2 linear vector fragments and the gene fragment were assembled into one linear vector construct by SOE PCR. An aliquot of the PCR product was transformed into *Bacillus subtilis*. Transformants were selected on LB plates supplemented with 6 μg of chloramphenicol per ml. A recombinant *Bacillus subtilis* clone containing the sequence confirmed integrated expression construct was cultivated in liquid culture on a rotary shaking table in 500 mL baffled Erlenmeyer flasks each containing 100 ml yeast extract-based media. The clone was cultivated for 4 days at 30° C. The enzyme containing supernatant was harvested and the enzyme purified as described in Example 2.

Example 2: Purification of the His-Tagged Amylase from *Bacillus amyloliquefaciens*

The pH of the supernatant was adjusted to pH 8 with 3 M Tris, left for 1 hour, and then filtered using a filtration unit equipped with a 0.2 μm filter (Nalgene). The filtered supernatant was applied to a 5 ml HisTrap™ Excel column (GE Healthcare Life Sciences) pre-equilibrated with 5 column volumes (CV) of 50 mM Tris/HCl pH 8. Unbound protein was eluted by washing the column with 8 CV of 50 mM Tris/HCl PH 8. The amylase was eluted with 50 mM HEPES PH 7-10 mM imidazole and elution was monitored by absorbance at 280 nm. The eluted amylase was desalted on a HiPrep™ 26/10 desalting column (GE Healthcare Life Sciences) pre-equilibrated with 3 CV of 50 mM HEPES pH 7-100 mM NaCl. The amylase was eluted from the column using the same buffer at a flow rate of 10 ml/minute. Relevant fractions were selected and pooled based on the chromatogram and SDS-PAGE analysis using 4-12% Bis-Tris gels (Invitrogen) and 2-(N-morpholino) ethanesulfonic acid (MES) SDS-PAGE running buffer (Invitrogen). The gel was stained with InstantBlue (Novexin) and destained using miliQ water. The concentration of the purified enzyme was determined by absorbance at 280 nm.

Example 3: Determination of pH Stability for Variant Alpha-Amylases

The pH stability of the amylase variants according to the invention were tested as described above using the G7-pNP kit (Sigma-Aldrich Catalog number MAK009). After growing the variants as described, supernatant samples of each variant were tested for increased stability at pH 4 over the parent amylase. A subsample was incubated at pH 4 and 37° C. for 19.5 or 21 hours in a 100 mM BR-buffer adjusted to pH 4 (hereafter called the stressed sample), while an equivalent subsample was stored at pH 7 at 4° C. or below in a 100 mM BR buffer adjusted to pH 7 (hereafter called the unstressed sample). Incubation was performed in a 96-well Nunc MicroWell polypropylene plate (Sigma Aldrich P6866) sealed with an Agilent PlateLoc plate-sealer.

After incubation, the samples were prediluted 20 to 200 times before activity was measured. Amylase activity was determined using a G7-pNP kit (Sigma-Aldrich Catalog number MAK009). Sample dilution was performed in the pH 7 BR buffer. A further dilution was done to a total in-assay dilution of 100× to 1000×. 10 μL of diluted sample is mixed with 40 UL G7 substrate in a 380-well PerkinElmer SpectraPlate reader-plate.

The stressed and unstressed sample of each variant were read on the same reader-plate. The enzyme activity was evaluated according to the G7 assay protocol. The solution was mixed and pre-incubated 1 minute at room temperature and absorption was measured every 20 sec. over 30 minutes at OD 405 nm, and the highest measured slope was used as a measure of enzyme activity. A well with no enzyme sample added was used as control, and any slope in that well was subtracted from all the measured activities on the same plate.

The results of the stability test are shown in Table 1 and 2 below.

TABLE 1

Half-life for variants stressed at pH 4.0, 37° C. for 19.5 hours

| Variant substitutions | IF | HIF | Half Life (hours) |
|---|---|---|---|
| A222I | 8.1 | 4.0 | 19.4 |
| A222V | 7.9 | 3.9 | 18.7 |
| S199G | 7.8 | 3.8 | 18.6 |
| N196W, N207W, N603W | 7.2 | 3.4 | 16.7 |
| N196W, N603W | 7.1 | 3.4 | 16.5 |
| N196W, N207W | 6.8 | 3.2 | 15.6 |
| A222E | 4.8 | 2.3 | 11.1 |
| N207W, N603W | 1.4 | 1.1 | 5.5 |
| N603W | 1.3 | 1.1 | 5.4 |
| Wt parent amylase SEQ ID NO: 1 | 1.0 | 1.0 | 4.8 |

TABLE 2

Half-life for variants stressed at pH 4.0, 37° C. for 21 hours

| Variant substitution | HIF | Half Life (hours) |
|---|---|---|
| S199G | 3.94 | 16.82 |
| A222V | 3.86 | 16.46 |
| A222I | 3.85 | 16.42 |
| N196W | 3.48 | 14.84 |

TABLE 2-continued

| Half-life for variants stressed at pH 4.0, 37° C. for 21 hours | | |
|---|---|---|
| Variant substitution | HIF | Half Life (hours) |
| A222E | 2.90 | 12.38 |
| Wt parent amylase SEQ ID NO: 1 | 1.08 | 4.61 |

The results show that all tested variants had increased stability at pH 4.0 compared to the wild type parent alpha-amylase of SEQ ID NO: 1.

Example 4: Determination of pH 4 Stability for Variant Alpha-Amylases in Presence of Raw Starch Amylase variants were tested as supernatants from fermentation and purified samples. Purified enzyme samples were diluted in water with 0.01% Brij to a concentration of 5 μM. For the assay, 10 μl of supernatant or diluted purified sample was mixed with 90 μl 10% raw corn starch in 100 mM BR buffer, pH 4. Each sample was prepared on two separate plates, where one was stressed by incubation for 18 hours at 37° C., 850 rpm (hereafter called stressed samples) and the second was incubated for 2 minutes at room temperature, 850 rpm (hereafter called unstressed samples). After respective incubation, both plates were spun down for 2 min at 2000 rpm and supernatants were stored at −20° C. until analysis. Defrosted supernatants were diluted 10× in 100 mM BR buffer, pH 7 and enzyme activity was evaluated using G7-pNP assay protocol (Roche/Hitachi, cat. no. 11876473). Briefly, 20 μl diluted enzyme sample was mixed with 100 μl G7-pNP solution and absorbance was followed at 405 nm for 20 min at room temperature. Initial slopes (0-2 min), after blank subtraction, were used as activity measure. Residual activity after stress was calculated by dividing activity of stressed samples with unstressed samples. From this, the half-life (T½) in hours of the enzyme candidate was computed as the incubation-time in hours divided by log2 of the residual activity multiplied by −1.

Improvement factor (IF) was calculated from the estimated half-life (T½), by dividing the estimated T½ for variants with the T½ of the wild type enzyme (SEQ ID NO: 1).

TABLE 3

| Half-life for variants stressed at pH 4.0, 37° C. for 18 hours in presence of raw starch | | | | | | |
|---|---|---|---|---|---|---|
| | Supernatant samples | | | Purified samples | | |
| | RA @ 18 h | T½ (hour) | IF (T½) | | RA @ 18 h | T½ (hour) |
| Wt parent amylase SEQ ID NO: 1 | 7% | 4.9 | 1.0 | Ref. | 0% | |
| N196W | 28% | 9.8 | 2.0 | N196W | 23% | 8.7 |

The results show that listed variants had increased stability at pH 4.0 compared to the wild type parent alpha-amylase of SEQ ID NO: 1.

Example 5: Impact of Protein Engineering on *B. amyloliquefaciens* Alpha-Amylase (SEQ ID NO: 1) to Improve Ethanol Yield and Increase Kinetics During Raw-Starch Corn Mash Fermentation This example describes the evaluation of the alpha-amylase of SEQ ID NO: 1 containing a mutation for improved ethanol and kinetics during raw-starch corn mash simultaneous saccharification and fermentation (SSF). Particularly, the ethanol and kinetics during fermentation are compared among the enzymes listed in Table 4.

TABLE 4

| List of enzymes used Enzymes |
|---|
| Wt AA *Bacillus amyloliquefaciens* (SEQ ID NO: 1) |
| N196W variant AA |

Seed Culture:

Cryo-preserved culture of *Saccharomyces cerevisiae* strain MBG5012 (deposited under Accession No. NRRL Y67700 at the *Agricultural Research* Service Patent Culture Collection 5 (NRRL), USA, and described in WO19/161227 (incorporated herein by reference in its entirety) was first grown in liquid YPD media (Yeast extract, 10 g. Peptone, 20 g. Dextrose, 60 g. dissolve in 1 L of distilled water). Cultivation was done aseptically in a sterile 125-ml Erlenmeyer flask filled with 50 ml YPD media and inoculated with 100 μl of cryo-preserved culture. Flask was incubated in a shaking incubator at 32° C. for 16 h with shaking at 150 rpm. The YPD grown seed cultures (40 ml) were centrifuged at 3,500 rpm for 10 min at 22° C., and the resulting cell pellet was washed and resuspended in tap water and glycerol. The resuspended cells were used to inoculate the corn mash at the beginning of simultaneous saccharification and fermentation (SSF).

Corn Mash:

Corn kernels were ground using the Turkish grind setting on a Bunn Coffee Grinder. The % dried solids (DS) of the corn flour was 84.50%. Using the Turkish ground corn and tap water, a slurry targeting 37.50% DS was prepared. The corn slurry was supplemented with 1000 ppm urea and 3 ppm of antibiotic LACTROL™ and its pH was adjusted to 4.5 prior to use in SSF. Final dried solids level was determined to be 37.50% DS.

Simultaneous Saccharification and Fermentation (SSF)

All fermentations were carried out in 12 mL round-bottom tubes with caps having a drilled hole. Tubes were filled with 3.8-4.5 g of corn slurry and inoculated with seed culture at 10 million cells per gram mash. A glucoamylase from *Trametes* cingulate (disclosed herein as SEQ ID NO: 7) was added to the tubes at 88 μg enzyme protein per g of dry corn solids. Amylases in Table 4 were added to the tubes at 32 μg enzyme protein per g of dry corn solids. All tubes contained the same glucoamylase and one amylase from Table 4 was added per tube. Tubes were incubated in an incubator at 32° C. Tubes were vortexed two times per day. Fermentation was run for 72 hours.

Weight Loss Analysis

Initial weight of tubes prior to fermentation was recorded. Weight of tubes was recorded after 18, 24, 48 and 72 h of fermentation. The difference in weight between 0 h and 18, 24, 48 and 72 h of fermentation was calculated. Weight difference was divided by g DS per tube resulting in g weight loss/g DS.

Ethanol Analysis

After 72 hours of fermentation, 100 μl of 40% v/v $H_2SO_4$ was added to each sample tube, samples were vortexed, and centrifuged at 3,500 rpm for 10 min at 22° C. The resulting supernatant was filtered through a 0.2 μm syringe filter. Filtered samples were stored at 4° C. prior to and during HPLC analysis. Analysis of ethanol was conducted using an HPLC (Agilent 1100/1200 series) machine equipped with a guard column (Bio-Rad, Micro-Guard Cation H+Cartridge, 30×4.6 mm) and an analytical column (Bio-Rad, Aminex HPX-87H, 300×7.8 mm) using 5 mM Sulfuric Acid as a mobile phase with a flow rate of 0.8 mL/min. Column temperature was maintained at 65° C., and ethanol was detected using a Refractive Index detector at 55° C.

Results

Table 5 and Table 6 show the $CO_2$ g weight loss kinetics/gDS and ethanol titers, respectively, for the amylases during corn mash fermentation. Results indicate that the fermentation kinetics and ethanol titer increase when the fermentation is run with a variant alpha-amylase comprising a N196W substitution versus the parent wt amylase. The difference in kinetics and ethanol titer can be attributed to the mutation present in the variant amylase. It can be concluded that the N196W substitution present in the variant provides improvement in fermentation performance by enabling increased activity on the starch substrate present in the raw-starch corn slurry.

TABLE 5

Gram weight loss/g DS kinetics during raw-starch fermentation run with

| Amylase | 18 h g Weight Loss/g DS Mean | 24 h g Weight Loss/g DS Mean | 48 h g Weight Loss/g DS Mean | 72 h g Weight Loss/g DS Mean |
|---|---|---|---|---|
| SEQ ID NO: 1 | 0.159 | 0.215 | 0.353 | 0.460 |
| N196W | 0.173 | 0.231 | 0.379 | 0.468 |

TABLE 6

Ethanol titer after 72 h of fermentation in raw-starch slurry with amylases from Table 4.

| Amylase | Mean Ethanol %(v/v) | Std Dev |
|---|---|---|
| SEQ ID NO: 1 | 18.32 | 0.13 |
| N196W | 19.01 | 0.18 |

Example 6. Determination of pH 4 Stability for Variant Alpha-Amylases in Presence and Absence of Raw Starch Purified amylase variants were diluted in water with 0.01% Brij to a concentration of 5 μM. For the assay, 10 μl diluted purified sample was mixed with 90 μl 100 mM BR buffer, pH or with 10% raw corn starch in 100 mM BR buffer, pH 4. Each sample was prepared on two separate plates, where one was stressed by incubation for 96 hours at 32° C., 850 rpm (hereafter called stressed samples) and the second was incubated for 2 minutes at room temperature, 850 rpm (hereafter called unstressed samples). After respective incubation, both plates were spun down for 2 min at 2000 rpm and supernatants were stored at −20° C. until analysis. Defrosted supernatants were diluted 10× in 100 mM BR buffer, pH 7 and enzyme activity was evaluated using G7-pNP assay protocol (Roche/Hitachi, cat. no.11876473). Briefly, 20 μl diluted enzyme sample was mixed with 100 μl G7-pNP solution and absorbance was followed at 405 nm for 20 min at room temperature. Initial slopes (0-2 min), after blank subtraction, were used as activity measure. Residual activity after stress was calculated by dividing activity of stressed samples with unstressed samples.

TABLE 7

Residual activities for variants stressed at pH 4.0, 32° C. for 96 hours in absence or presence of raw starch.

| Mutations relative to WT parent amylase SEQ ID NO: 1 | Residual Activity after incubation in buffer pH 4, with 10% starch | Residual Activity after incubation in buffer pH 4 |
|---|---|---|
| S199G H626* | 9 | 0 |
| L150H S199G A222I | >95 | 83 |
| L150M S199G A222V | 86 | 88 |
| N196W S199G A222V N603W | 82 | 91 |
| L150Y N196W S199G A222V | >95 | 93 |
| L150F N196W S199G A222I | >95 | >95 |
| L150M N196W S199G A222V | >95 | >95 |
| L150W S199G A222V | >95 | >95 |
| L150H N196W S199G A222V | >95 | >95 |
| N196W S199G A222V H626* | >95 | >95 |
| L150W N196W S199G A222I | >95 | >95 |
| N196W S199G A222V | >95 | >95 |
| L150Y N196W S199G A222V | >95 | >95 |
| L150Y S199G A222V | >95 | >95 |

The results show that listed variants had increased stability at pH 4.0 compared to the wild type parent alpha-amylase of SEQ ID NO: 1.

Example 7. Determination of pH 4 Stability for Variant Alpha-Amylases

Purified amylase variants were diluted in water with 0.01% Trition-X-100 to a concentration of 5 μM. For the assay, the 5 UM samples were diluted 10× into either stress buffer (222 mM sodium acetate buffer pH 4, 0.56 mM CaCl2 and 0.01% Brij-35) or dilution buffer (0.01% Trition-X-100). Samples in the stress buffer were incubated at 32° C. (850 rpm) for 24H (hereafter called stressed samples). The other samples mixed with dilution buffer were stored at 5° C. until further analysis, max. 2 days (hereafter called unstressed samples).

After the respective incubations, samples were diluted 10-50× with assay buffer (500 mM Hepes pH 7, 0.5 mM CaCl2, 0.01% Brij-35) and enzyme activity was evaluated using G7-pNP assay protocol (Roche/Hitachi, cat. no. 11876473). Briefly, 20 μl diluted enzyme sample was mixed with 100 μl G7-pNP solution and absorbance was measured at 405 nm for 20 min at room temperature. Initial slopes (lag time: 2 min, max absorbance=2) were calculated and blank subtracted. These slopes-blank were used as activity measure. Residual activity (RA %) after stress was calculated by dividing activity of stressed samples with unstressed samples and multiplying with 100.

TABLE 8

Residual activities (RA %) for variants stressed at pH 4.0, 32° C. for 24 hours.

| Variant substitutions | % RA after 24 hrs at pH 4 |
|---|---|
| Wt parent amylase SEQ ID # 1 | 0 |
| A222V, H626* | 13.8 |
| A222I, H626* | 14.4 |
| A222E, H626* | 4.2 |
| N196W, H626* | 10.2 |

TABLE 8-continued

Residual activities (RA %) for variants stressed at pH 4.0, 32° C. for 24 hours.

| Variant substitutions | % RA after 24 hrs at pH 4 |
|---|---|
| L150H, H626* | 1.6 |
| L150M, H626* | 0.70 |
| L150Y, H626* | 6.3 |
| L150W | 7.9 |
| S199G | 18.1 |
| N196W, N603W, H626* | 8.3 |
| N196W, N207W, H626* | 11.3 |
| N196W, N207W, N603W, H626* | 9.4 |
| N196W, S199G, A222V | 65.1 |
| N196W, S199G, A222V, H626* | 64.0 |
| N196W, S199G, A222V, N603W | 66.6 |
| L150F, N196W, S199G, A222I | 94.7 |
| L150H, S199G, A222I | 55.6 |
| L150M, S199G, A222V | 65.5 |
| L150M, N196W, S199G, A222V | 64.2 |
| L150W, S199G, A222V | 61.7 |
| L150W, N196W, S199G, A222I | 90.3 |
| L150Y, S199G, A222V | 58.2 |
| L150Y, N196W, S199G, A222V | 80.9 |
| L150H, N196W, S199G, A222V | 71.0 |
| E96K, D179S, N196W, S199G, A222V, E284Q | 77.9 |
| R64S, E96K, N196W, S199G, A222V | 86.6 |

The results show that the listed variants had increased stability at pH 4.0 compared to the wild type parent alpha-amylase of SEQ ID NO: 1.

Example 8. Determination of pH 4 Stability for Variant Alpha-Amylases

Purified amylase variants were diluted in water with 0.01% Trition-X-100 to a concentration of 5 μM. For the assay, the 5 UM samples were diluted 10× into either stress buffer (222 mM sodium acetate buffer pH 4, 0.56 mM CaCl2 and 0.01% Brij-35) or dilution buffer (0.01% Trition-X-100). Samples in the stress buffer were incubated at 32° C. (850 rpm) for 24 Hours (hereafter called stressed samples). The other samples mixed with dilution buffer were stored at 5° C. until further analysis (hereafter called unstressed samples).

After incubation, the stressed samples were diluted 10-50× with assay buffer (500 mM Hepes pH 7, 0.5 mM CaCl2, 0.01% Brij-35). The unstressed samples were diluted between 10-100× to get minimum four different dilutions and thus minimum 4 different concentrations. Enzyme activity was evaluated for all diluted samples (stressed and unstressed) using G7-pNP assay protocol (Roche/Hitachi, cat. no.11876473). Briefly, 20 μl diluted enzyme sample was mixed with 100 μl G7-pNP solution and absorbance was measured at 405 nm for 20 min at room temperature. Initial slopes (lag time: 2 min, max absorbance=1.5) were calculated. For the unstressed samples, a nonlinear fit (e.g. Michaelis Menten) was made using initial slopes as Y and enzyme concentration as X. Based on this fit, the concentration of residual active enzyme was estimated in the stressed samples. The level of residual activity (RA %) was calculated by dividing the estimated concentration of residual active enzyme with the initial concentration of enzyme (at start) and multiplying with 100.

The results are given in Table 9 below. The listed alterations were introduced into the parent alpha-amylase of SEQ ID NO: 1, and the results show that the listed variants had increased stability at pH 4.0 compared to the wild type parent alpha-amylase of SEQ ID NO: 1.

TABLE 9

Residual activities (RA %) for variants stressed at pH 4.0, 32° C. for 24 hours.

| Variant substitutions | % RA after 24 hrs at pH 4 2 |
|---|---|
| Wt parent amylase of SEQ ID NO: 1 | 0 |
| N28W, H626* | 12.8 |
| S199G, H626* | 21.6 |
| N196W, V599W, H626* | 11 |
| N196W, H550Y, P605S, H626* | 12.5 |
| N196W, A545P, T576Y, H626* | 8 |
| N196W, K549Y, G560P, H626* | 8.7 |
| I108P, Y183I, N196W, I205Y, H626* | 16.9 |
| N196W, R323K, H626* | 9.6 |
| N196W, D283P, H626* | 11.4 |
| W138Y, N196W, H626* | 9.6 |
| L150W, H626* | 7.2 |
| N196W, N392W, K417W, H626* | 8.3 |
| N196W, N392R, K417W, H626* | 15.6 |
| N196W, K549*, H550*, D551*, H626* | 14.6 |
| N196W, P580*, E581*, N582*, H626* | 14 |
| N196W, F592FK, H626* | 10.9 |
| N28W, N196W, N207W, S386D, N603W, H626* | 9.3 |
| R38Y, N196W, H626* | 16.4 |
| N196W, H259Y, H626* | 11.4 |
| N196W, Q412W, H626* | 10 |
| N196W, F212W, H626* | 11.7 |
| N196W, V599W, H626* | 10 |
| N196W, H550Y, P605S, H626* | 13.4 |
| N196W, H550Y, K589F, H626* | 11.7 |
| N196W, H550Y, D608Y, H626* | 11.8 |
| N196W, M574W, L614W, H626* | 14.4 |
| N196W, G533H, M574W, L614W, H626* | 9.5 |
| N196W, V543P, N570H, H626* | 16.8 |
| N196W, G533H, Y575W, L614W, H626* | 11.1 |
| N196W, A545P, T576Y, H626* | 14.4 |
| N196W, A566P, T578Y, H626* | 11.9 |
| N196W, K549Y, G560P, H626* | 15.2 |
| N196W, A566P, L577Y, H626* | 14.4 |
| N196W, I547Y, G560P, H626* | 13.2 |
| N196W, M574MW, H626* | 16.5 |
| N196W, K549*, H550*, D551*, M574MW, P580*, E581*, N582*, F592FK, H626* | 13.1 |
| N196W, L614W, G619W, H626* | 14.4 |
| N28W, I108P, N196W, N207W, S386D, A466V, Q542K, N603W, H626* | 19.5 |
| N28W, I108P, N196W, N207W, S386D, N603W, H626* | 16.2 |
| N196W, D282P, D283*, H626* | 7.7 |
| W138Y, N196W, H626* | 6.6 |
| N28W, N196W, N207W, S386D, N603W, H626* | 19.5 |
| N196W, S388W, A424P, H626* | 15.9 |
| N196W, S388W, A424P, L489Q, H626* | 16 |
| A117T, N196W, H550Y, D608Y, H626* | 7.8 |
| N196W, Q457R, Y575W, L614W, H626* | 13.4 |
| N196W, S199G | 41.7 |
| N196W, A222V | 40.4 |
| N196W, A222E | 44.4 |
| N196W, A222I | 32.4 |
| S199G, A222V | 55.6 |
| S199G, A222E | 40.7 |
| S199G, A222I | 48.5 |
| N196W, S199G, A222I | 72.5 |
| Q134L, H626* | Below 5 |
| L150W, N156K, N196W, S199G, A222V | 71.7 |
| L150Y, N156K, N196W, S199G, A222I | 63.2 |
| L150W, N196W, S199G, A222I, A428S | 73.1 |
| L150F, N156K, N196W, S199G, A222I | 67.7 |
| L150Y, N156R, N196W, A222V | 70.6 |
| L150M, N156R, N196W, S199G, A222I | 64.9 |
| L150M, N156R, N196W, A222V | 61.2 |
| L150Y, N156R, N196W, S199G, A222V | 69.8 |
| L150M, N156K, N196W, S199G, A222V | 51.1 |
| L150Y, N156R, N196W, A222I | 94.2 |
| L150H, N156R, N196W, S199G, A222I | 63.1 |
| L150H, N156K, N196W, A222V | 75 |

TABLE 9-continued

Residual activities (RA %) for variants stressed at pH 4.0, 32° C. for 24 hours.

| Variant substitutions | % RA after 24 hrs at pH 4 2 |
| --- | --- |
| L150W, N156R, N196W, A222I | 87.6 |
| L150F, N156R, N196W. A222I | Above 95 |
| L150F, N156K, N196W, S199G, A222V | 81.6 |
| L150H, N156K, N196W, S199G, A222V | 60.8 |
| L150F, N156R, S199G, A222I | 65.9 |
| L150M, N156K, N196W, A222V | 57.5 |
| L150W, N156K, N196W, S199G, A222I | 72.2 |
| N156K, N196W, S199G, A222V | 65.3 |
| L150Y, N156R, S199G, A222I | 88.7 |
| L150M, N156R, S199G, A222I | 64.4 |
| L150W, N156K, S199G, A222V | 74.6 |
| L150W, N156R, N196W, S199G, A222V | 58.4 |
| L150Y, N156R, N196W | 52.1 |
| N156K, N196W, A222V | 59 |
| N156K, N196W, S199G | 46.4 |
| N156R, S199G, A222V | 82.2 |
| S113H, N196W, S199G, A222V | 55.5 |
| Q71E, S113H, N196W, S199G, A222V | 52.9 |
| N196W, S199G, A222V, D283A | 78 |
| N196W, S199G, A222V, D283P | 88.5 |
| W142E, D193SQY, N196W, S199G, A222V, R224K | 13.5 |
| E96K, K101R, L150W, N156R, D179S, N196W, S199G, T208N, A222V | 68.3 |
| E96K, K101R, L150Y, N156R, D179S, N196W, S199G, T208N, A222V, E284Q | 72.8 |
| E96K, K101R, L150M, N156R, D179S, N196W, S199G, T208N, A222V, E284Q | 58.2 |
| S113Q, Q134E, N196W, S199G, A222V | 50.5 |
| S113D, Q134N, N196W, S199G, A222V | 67 |
| S113F, N196W, S199G, A222V | 70.5 |
| E171Q, N196W, S199G, N204D, A222V | 81.9 |
| N196W, S199G, A222V, H241N, S245N, T278N, E284Q, E285V | 80 |
| N196W, S199G, A222V, S394K, A414K, K417Y | 56.9 |
| N196W, S199G, A222V, E359Y, S394K, K396S, A414K, K417Y | Above 95 |
| R38H, E96K, G99N, K101R, D179S, N196W, S199G, A222V | 83.1 |
| R38H, E96K, G99N, K101R, D179S, N196W, S199G, A222V, E284Q | 80.3 |
| V107T, H110D, N196W, S199G, A222V | 66.9 |
| Q134T, L150Y, N196W, S199G, A222V | 86.2 |
| S113F, L150W, N196W, S199G, A222V | 68.6 |
| S113F, L150Y, N196W, S199G, A222V | Above 95 |
| E96K, K101R, N156R, D179S, N196W, S199G, T208N, A222V | 69.4 |
| E96K, K101R, L150Y, N156R, D179S, N196W, S199G, T208N, A222V | 61.3 |
| E96K, K101R, L150M, N156R, D179S, N196W, S199G, T208N, A222V | 86.7 |
| E96K, K101R, N156R, D179S, N196W, S199G, T208N, A222V, E284Q | 66.9 |
| E96K, K101R, L150W, N156R, D179S, N196W, S199G, T208N, A222V, E284Q | 72.6 |
| N28R, Q86R, N196W, S199G, A222V | 63.1 |
| N28R, Q86R, K89R, N196W, S199G, A222V | 91.9 |
| G56P, N196W, S199G, S209L, A222V | 88.2 |
| E96K, N196W, S199G, A222V | 76.4 |
| T10I, N196W, S199G, A222V | 80.7 |
| D39R, N196W, S199G, A222V | 75.8 |
| R64S, N196W, S199G, A222V | 90.4 |
| T10I, D39R, R64S, N196W, S199G, A222V | 78.2 |
| T10I, D39R, N196W, S199G, A222V | 56.8 |
| D39R, E96K, N196W, S199G, A222V | 87 |
| R64S, D90E, E96K, N196W, S199G, A222V | 85.5 |
| R38H, D39R, E96K, G99N, K1O1R, D179S, N196W, S199G, A222V | 82.9 |
| R38H, R64S, E96K, G99N, K1O1R, D179S, N196W, S199G, A222V | 90.1 |
| T10I, R38H, R64S, E96K, G99N, K101R, D179S, N196W, S199G, A222V | 47.6 |

TABLE 9-continued

Residual activities (RA %) for variants stressed at pH 4.0, 32° C. for 24 hours.

| Variant substitutions | % RA after 24 hrs at pH 4 2 |
| --- | --- |
| T10I, R38H, R64S, D90E, E96K, G99N, K101R, D179S, N196W, S199G, A222V | 51 |
| T10I, R38H, D39R, E96K, G99N, K101R, D179S, N196W, S199G, A222V | 65.4 |
| R38H, D39R, R64S, E96K, G99N, K101R, D179S, N196W, S199G, A222V | 53.5 |
| E96K, N196W, S199G, A222V, E284Q | 58.4 |
| T10I, N196W, S199G, A222V, E284Q | 58.6 |
| D39R, N196W, S199G, A222V, E284Q | 50.4 |
| R64S, N196W, S199G, A222V, E284Q | 54.4 |
| T10I, D39R, E96K, N196W, S199G, A222V, E284Q | 62.3 |
| D193SQY, N196W, S199G, A222V | 38 |
| Q134T, N196W, S199G, A222V | 47.8 |
| L174I, N196W, S199G, T208N, A222V | 63.6 |
| Y183F, N196W, S199G, T208S, A222V | 64.8 |
| N127D, N156R, N196W, S199G, A222V | 83.1 |
| Q134T, L150W, N196W, S199G, A222V | 70.6 |
| N57P, N196W, S199G, A222V | 73.1 |
| N196W, S199G, Q200W, A222V | 58.7 |
| T10I, D39R, R64S, E96K, N196W, S199G, A222V, E284Q | 67.2 |
| T10I, D39R, R64S, N196W, S199G, A222V, E284Q | 78.1 |
| T10I, R64S, E96K, N196W, S199G, A222V, E284Q | 62.1 |
| D39R, R64S, D90E, E96K, N196W, S199G, A222V, E284Q | 64.8 |
| T10I, R64S, E96K, N196W, S199G, A222V | 54.5 |
| T10I, D39R, N196W, S199G, A222V, E284Q | 70.2 |
| D39R, E96K, N196W, S199G, A222V, E284Q | 52.3 |
| D39R, R64S, N196W, S199G, A222V, E284Q | 60.7 |
| R64S, E96K, N196W, S199G, A222V, E284Q | 67.9 |
| D39R, R64S, N196W, S199G, A222V | 63 |
| S12*, S13*, V14*, K15*, N16*, I103Y, N196W, S199G, A222V, N233S, T308Y | 48.8 |
| S12*, S13*, V14*, K15*, N16*, A43D, I103Y, N196W, S199G, A222V, N233S, T308M | 49.9 |
| V9L, S12P, V14I, N16S, A43T, N196W, S199G, A222V | 70.9 |
| S12*, S13*, V14*, K15*, N16*, N196W, S199G, A222V | 54.1 |
| N28W, N196W, S199G, A222V | 66.8 |
| N196W, S199G, A222V, N392W, K417W | 63.1 |
| T10I, D39R, E96K, N196W, S199G, A222V | 70.7 |
| V9D, R38H, N196W, S199G, A222V, T348K | 70.4 |
| S113F, L150Y, N156K, N196W, S199G, A222V, H626* | 59.2 |
| S113Y, L150Y, N156K, N196W, S199G, A222V, H626* | 73.1 |
| S113W, L150Y, N156K, N196W, S199G, A222V, H626* | 68.4 |
| S113F, N156K, N196W, S199G, A222V, H626* | 51.7 |
| S113Y, N156K, N196W, S199G, A222V, H626* | 42.1 |
| S113W, N156K, N196W, S199G, A222V, H626* | 59.2 |
| W138Y, L150V, N196W, S199G, A222V, H626* | 43.9 |
| W138Y, L150V, D179G, N196W, S199G, A222V, H626* | 39.3 |
| W138Y, L150V, N196W, S199G, L218W, A222V, H626* | 29.8 |
| E96K, Q134L, D179S, N196W, S199G, A222V, E284Q, H626* | 78.5 |
| E96K, Q134L, L150Y, N156R, D179S, N196W, S199G, A222V, E284Q, H626* | 51 |
| E96K, L150Y, N156R, D179S, N196W, S199G, A222V, E284Q, H626* | 65.2 |
| R38H, E96K, G99N, K101R, Q134L, D179S, N196W, S199G, S221N, A222V, H626* | 65.1 |
| R38H, E96K, G99N, K101R, Q134L, D179S, N196W, S199G, A222V, H626* | 69.9 |

TABLE 9-continued

| Residual activities (RA %) for variants stressed at pH 4.0, 32° C. for 24 hours. | |
|---|---|
| Variant substitutions | % RA after 24 hrs at pH 4 2 |
| R38H, E96K, G99N, K101R, Q134L, L150Y, N156R, D179S, N196W, S199G, A222V, H626* | 62.1 |
| R38H, E96K, G99N, K101R, L150Y, N156R, D179S, N196W, S199G, A222V, H626* | 59.4 |
| L150F, N196W, S199G, A222I, H626* | 86.7 |
| Q134L, L150F, N156R, N196W, S199G, A222I, H626* | 78.8 |
| Q134L, L150H, N156R, N196W, S199G, A222I, H626* | 83.7 |
| Q134L, L150M, N156K, N196W, S199G, A222I, H626* | 68.1 |
| Q134L, L150Y, N156K, N196W, S199G, A222I, Q457L, H626* | 80.8 |
| Q134M, L150W, N156K, N196W, S199G, A222I, H626* | 50.9 |
| Q134W, L150W, N156K, N196W, S199G, A222I, H626* | 63.2 |
| L150W, L152M, N156K, N196W, S199G, A222I, H626* | 56.9 |
| S113F, L150W, N156K, N196W, S199G, A222I, H626* | 69.2 |
| S113Y, L150W, N156K, N196W, S199G, A222I, H626* | 55.6 |
| L150W, G151W, N156K, N196W, S199G, A222I, H626* | 23.2 |
| L150W, G151S, N156K, N196W, S199G, A222I, H626* | 22.1 |
| S113F, L150W, G151S, N156K, N196W, S199G, A222I, H626* | 38.3 |
| Y67W, W68Y, L150W, N156K, N196W, S199G, A222I, H626* | 60.6 |
| A43V, L150M, G151F, N156R, N196W, S199G, A222I | 48.2 |
| L150M, G151Y, N156R, N196W, S199G, A222I | 20.2 |
| L150M, G151W, N156R, N196W, S199G, A222I | 25.5 |
| L150M, G151S, N156R, N196W, S199G, A222I, Y534H | 52.8 |
| S113F, L150M, G151S, N156R, N196W, S199G, A222I | 17.6 |
| Q134L, L150F, N156K, N196W, S199G, A222I, H626* | 53.5 |
| L150W, G151F, N156K, N196W, S199G, A222I, H626* | 50.4 |
| L150W, G151Y, N156K, N196W, S199G, A222I, H626* | 46.4 |
| Y67W, W68Y, L150W, N156K, N196W, S199G, A222I | 58.1 |
| G56W, N57P, Y67W, W68Y, L150W, N156K, N196W, S199G, A222I, H626* | 60.5 |
| K54I, Y67W, W68S, S113G, N196W, S199G, A222V, A382T, H626* | 44.3 |
| K54I, Y67W, W68S, S113G, D114Q, L150V, N196W, S199G, A222V, H626* | 24.4 |
| K54I, Y67W, W68S, S113G, W138Y, N196W, S199G, A222V, H626* | 39.6 |
| K54I, Y67W, W68S, S113G, D114Q, W138Y, L150V, N196W, S199G, A222V, H626* | 18.8 |
| Q134L, N196W, S199G, A222V, H626* | 57.7 |
| V107T, I108L, H110D, F169H, N196W, S199G, A222V, H626* | 69.9 |
| N196W, S199G, A222V, N392W, K417W, H626* | 59.8 |
| V9D, R38H, N196W, S199G, A222V, T348K, H626* | 50.4 |
| E96H, L150Y, N156R, N196W, S199G, A222V, E284Q, H626* | 69.8 |
| Q134L, L150Y, N196W, S199G, A222V, H626* | 70.4 |
| L150Y, N196W, S199G, A222V, H626* | Above 95 |
| Q134L, L150Y, N196W, S199G, A222V, H626* | Above 95 |
| L150F, N156R, N196W, S199G, A222V, H626* | 52.6 |
| L150H, N156R, N196W, S199G, A222V, H626* | 70.1 |

TABLE 9-continued

| Residual activities (RA %) for variants stressed at pH 4.0, 32° C. for 24 hours. | |
|---|---|
| Variant substitutions | % RA after 24 hrs at pH 4 2 |
| Q134L, L150F, N156R, N196W, S199G, A222V, H626* | Above 95 |
| Q134L, L150H, N156R, N196W, S199G, A222V, H626* | Above 95 |
| Q134L, L150F, N156K, N196W, S199G, A222V, H626* | Above 95 |
| Q134L, L150H, N156K, N196W, S199G, A222V, H626* | Above 95 |
| Q134L, L150Y, N156K, N196W, S199G, A222V, H626* | Above 95 |
| L150Y, N156K, N196W, S199G, A222V, H626* | Above 95 |
| Q134L, L150Y, N156K, N196W, S199G, A222V, H626* | Above 95 |
| Q134W, L150Y, N156K, N196W, S199G, A222V, H626* | Above 95 |
| Q134M, L150Y, N156K, N196W, S199G, A222V, H626* | Above 95 |
| Q134M, L150Y, N156K, N196W, S199G, A222V, A466V, H626* | Above 95 |
| L150Y. L152M, N156K, N196W. S199G, A222V, H626* | Above 95 |
| L150S, N196W, S199G, A222V, H626* | Above 95 |
| N196W, S199G, A222V, N281S, H626* | Above 95 |
| Y67T, N196W, S199G, A222V, H626* | Above 95 |
| Q71N, N196W, S199G, A222V, H626* | Above 95 |
| Q71N, A94D, N196W, S199G, A222V, H626* | Above 95 |
| N196W, S199G, L218F, A222V, H626* | 64.8 |
| N196W, S199G, L218W, A222V, H626* | Above 95 |
| N196W, S199G, A222V, T278W, H626* | 66.8 |
| N196W, S199G, A222V, T278W, T459M, H626* | Above 95 |
| N196W, S199G, A222V, T278Y, H626* | Above 95 |
| N196W, S199G, A222V, S275N, H626* | 59.8 |
| N196W, S199G, A222V, S275L, H626* | Above 95 |
| N196W, S199G, A222V, S335Q, H626* | Above 95 |
| N196W, S199G, A222V, S335K, H626* | 71.3 |
| N196W, S199G, A222V, S335R, H626* | Above 95 |
| N196W, S199G, L218W, A222V, S335K, H626* | Above 95 |
| N196W, S199G, L218W, A222V, S335Q, H626* | 92.1 |
| Y67W, N196W, S199G, A222V, H626* | Above 95 |
| N196W, S199G, A222V, N281Q, H626* | Above 95 |
| L150M, N156R, N196W, S199G, A222V, H626* | Above 95 |
| Q134L, L150M, N156R, N196W, S199G, A222V, H626* | Above 95 |
| Q134L, L150M, N156K, N196W, S199G, A222V, H626* | Above 95 |
| D39R, N196W, S199G, A222V, N281Q, E284Q | Above 95 |
| D39R, N196W, S199G, A222V, E284Q, Q479QP | Above 95 |
| D39R, Y70F, N196W, S199G, A222V, E284Q | Above 95 |
| N28W, D39R, N196W, S199G, A222V, E284Q | Above 95 |
| D39R, N196W, S199G, N207W, A222V, E284Q | Above 95 |
| E1*, T2*, A3*, N4*, K5*, S6*, N7*, K8*, D39R, N196W, S199G, N207W, A222V, E284Q, H626* | Above 95 |
| N196W, N207W | 19.2 |
| N196W, N207W, E284Q | 19 |
| E1*, T2*, A3*, N4*, K5*, S6*, N7*, K8*, N196W, N207W, E284Q | 16.8 |
| L150Y, N196W, S199G, A222V, H626* | Above 95 |
| E1*, T2*, A3*, N4*, K5*, S6*, N7*, K8*, L150Y, N196W, S199G, A222V | Above 95 |
| E96K, K101R, L150M, N156R, D179S, N196W, S199G, N207W, T208N, A222V | Above 95 |
| E1*, T2*, A3*, N4*, K5*, S6*, N7*, K8*, E96K, K101R, L150M, N156R, D179S, N196W, S199G, T208N, A222V | Above 95 |
| Q134L, L150H, N156R, N196W, S199G, A222I, E284Q, H626* | Above 95 |
| E1*, T2*, A3*, N4*, K5*, S6*, N7*, K8*, Q134L, L150H, N156R, N196W, S199G, A222I, H626* | Above 95 |

TABLE 9-continued

Residual activities (RA %) for variants stressed at pH 4.0, 32° C. for 24 hours.

| Variant substitutions | % RA after 24 hrs at pH 4 2 |
|---|---|
| E1*, T2*, A3*, N4*, K5*, S6*, N7*, K8*, Q134L, L150H, N156R, N196W, S199G, N207W, A222I, E284Q | Above 95 |
| E96K, D179S, N196W, S199G, A222V, E284Q, H626* | Above 95 |
| E1*, T2*, A3*, N4*, K5*, S6*, N7*, K8*, E96K, D179S, N196W, S199G, A222V, E284Q | 88.4 |
| R64S, E96K, N196W, S199G, N207W, A222V | Above 95 |
| N28W, D39R, N196W, S199G, N207W, A222V, E284Q | Above 95 |
| D39R, N196W, S199G, A222V, E284Q, H626* | Above 95 |
| D39R, N196W, S199G, N207W, A222V, E284Q | Above 95 |
| E1*, T2*, A3*, N4*, K5*, S6*, N7*, K8*, D39R, N196W, S199G, A222V, E284Q | Above 95 |
| E1*, T2*, A3*, N4*, K5*, S6*, N7*, K8*, N196W, N207W, E511D | 20.9 |
| L150Y, N196W, S199G, N207W, A222V | Above 95 |
| E96K, K101R, L150M, N156R, D179S, N196W, S199G, T208N, A222V, H626* | Above 95 |
| E96K, K101R, L150M, N156R, D179S, N196W, S199G, T208N, A222V, E284Q | Above 95 |
| E1*, T2*, A3*, N4*, K5*, S6*, N7*, K8*, E96K, K101R, L150M, N156R, D179S, N196W, S199G, N207W, T208N, A222V, E284Q, H626* | Above 95 |
| Q134L, L150H, N156R, N196W, S199G, A222I | Above 95 |
| N28W, E96K, D179S, N196W, S199G, A222V, E284Q | Above 95 |
| R64S, E96K, N196W, S199G, A222V, H626* | Above 95 |
| R64S, E96K, N196W, S199G, A222V, E284Q | Above 95 |
| E1*, T2*, A3*, N4*, K5*, S6*, N7*, K8*, R64S, E96K, N196W, S199G, A222V | 93.7 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. An alpha-amylase variant, comprising a N196W substitution and an alteration at one or more positions corresponding to positions 1, 2, 3, 4, 5, 6, 7, 8, 9, 10, 11, 13, 15, 28, 38, 39, 43, 54, 56, 57, 67, 68, 70, 71, 86, 89, 90, 94, 96, 99, 101, 103, 107, 110, 113, 114, 117, 127, 134, 138, 142, 150, 151, 152, 156, 169, 171, 174, 179, 183, 193, 199, 200, 204, 205, 207, 208, 209, 212, 218, 221, 222, 224, 233, 241, 245, 259, 275, 278, 281, 282, 283, 284, 285, 308, 323, 335, 348, 359, 382, 386, 388, 392, 394, 396, 412, 414, 417, 424, 428, 457, 459, 466, 479, 489, 511, 533, 534, 543, 545, 547, 549, 550, 551, 560, 566, 570, 575, 576, 577, 578, 580, 582, 589, 592, 599, 603, 605, 608, 614, 619, or 626 of the polypeptide of SEQ ID NO: 1, wherein the variant has alpha-amylase activity and wherein the variant has at least 70%, but less than 100% sequence identity, to the polypeptide of SEQ ID NO: 1.

2. The variant according to claim 1, wherein the alteration comprises a substitution at one or more positions corresponding to positions 196, 199, 96, 150, 179, 207, 222, 284 and 603 of the polypeptide of SEQ ID NO: 1, wherein the variant has alpha-amylase activity and wherein the variant has at least 70%, but less than 100% sequence identity, to the polypeptide of SEQ ID NO: 1.

3. The variant of claim 1, wherein the alteration is selected from the group consisting of: E1*, T2*, A3*, N4*, K5*, S6*, N7*, K8*, V9*, V9D, V9L, T10*, T10I, A11*, S13*, K15*, N28R, N28W, R38H, R38Y, D39R, A43D, A43T, A43V, K541, G56P, G56W, N57P, Y67T, Y67W, W68S, W68Y, Y70F, Q71E, Q71N, Q86R, K89R, D90E, A94D, E96H, E96K, G99N, K101R, I103Y, V107T, H110D, S113D, S113F, S113G, S113H, S113Q, S113W, S113Y, D114Q, A117T, N127D, Q134E, Q134L, Q134M, Q134N, Q134T, Q134W, W138Y, W142E, L150F, L150H, L150M, L150S, L150V, L150W, L150Y, G151F, G151S, G151W, G151Y, L152M, N156K, N156R, F169H, E171Q, L174I, D179G, D179S, Y183F, Y183I, D193SQY, N196W, S199G, Q200W, N204D, I205Y, N207W, T208N, T208S, S209L, F212W, L218F, L218W, S221N, A222E, A222I, A222V, R224K, N233S, H241N, S245N, H259Y, S275L, S275N, T278N, T278W, T278Y, N281Q, N281S, D282P, D283*, D283A, D283P, E284Q, E285V, T308M, T308Y, R323K, S335K, S335Q, S335R, T348K, E359Y, A382T, S386D, S388W, N392R, N392W, S394K, K396S, Q412W, A414K, K417W, K417Y, A424P, A428S, Q457L, Q457R, T459M, A466V, Q479QP, L489Q, E511D, G533H, Y534H, V543P, A545P, I547Y, K549*, K549Y, H550*, H550Y, D551*, G560P, A566P, N570H, Y575W, T576Y, L577Y, T578Y, P580*, N582*, K589F, F592FK, V599W, N603W, P605S, D608Y, L614W, G619W, and H626*.

4. The variant of claim 3, wherein the alteration is selected from the group consisting of: E96K, L150Y, L150W, L150H, L150M, L150F, D179S, N196W, S199G, N207W, A222E, A222I, A222V, E284Q, N603W, and H626*.

5. The variant of claim 1, which has an improved property relative to the parent, wherein the improved property is increased pH stability at pH 4.0, 32° C. to 37° C., compared to the alpha-amylase of SEQ ID NO: 1.

6. The variant of claim 1, comprising a substitution or a combination of substitutions selected from:

N196W+N207W;
N196W+N603W;
N196W+N207W+N603W;
A222I+S199G+N196W;
A222V+S199G+N196W;
A222E+S199G+N196W;
A222V+S199G+N196W+L150Y;
N196W+S199G+A222V+N603W;
L150F+N196W+S199G+A222I;
L150M+N196W+S199G+A222V;
L150H+N196W+S199G+A222V;
L150W+N196W+S199G+A222I;
E96K+D179S+N196W+S199G+A222V+E284Q; and
R64S+E96K+N196W+S199G+A222V;

wherein the variant has alpha-amylase activity and wherein the variant has at least 70%, but less than 100% sequence identity, to the polypeptide of SEQ ID NO: 1.

7. The variant of claim 1, comprising a N-terminal deletion comprising at least amino acids 11 to 626 of SEQ ID NO: 1, at least amino acids 12 to 626 of SEQ ID NO: 1, or at least amino acids 13 to 626 of SEQ ID NO: 1.

8. The variant of claim 1, further comprising a C-terminal deletion, H626*.

9. The variant of claim 1, comprising an alteration or a combination of alterations selected from:

N196W+V599W;
N196W+H550Y+P605S;
N196W+A545P+T576Y;
N196W+K549Y+G560P;
I108P+Y183I+N196W+I205Y;
N196W+R323K;
N196W+D283P;
W138Y+N196W;
L150W;
N196W+N392W+K417W;
N196W+N392R+K417W;
N196W+K549*+H550*+D551*;
N196W+P580*+E581*+N582*;
N196W+F592FK;
N28W+N196W+N207W+S386D+N603W;
R38Y+N196W;
N196W+H259Y;
N196W+Q412W;
N196W+F212W;
N196W+V599W;
N196W+H550Y+P605S;
N196W+H550Y+K589F;
N196W+H550Y+D608Y;
N196W+M574W+L614W;
N196W+G533H+M574W+L614W;
N196W+V543P+N570H;
N196W+G533H+Y575W+L614W;
N196W+A545P+T576Y;
N196W+A566P+T578Y;
N196W+K549Y+G560P;
N196W+A566P+L577Y;
N196W+I547Y+G560P;
N196W+M574MW;
N196W+K549*+H550*+D551*+M574MW+P580*+E581*+N582*+F592FK;
N196W+L614W+G619W;
N28W+I108P+N196W+N207W+S386D+A466V+Q542K+N603W;
N28W+I108P+N196W+N207W+S386D+N603W;
N196W+D282P+D283*;
W138Y+N196W;
N28W+N196W+N207W+S386D+N603W;
N196W+S388W+A424P;
N196W+S388W+A424P+L489Q;
A117T+N196W+H550Y+D608Y;
N196W+Q457R+Y575W+L614W;
N196W+S199G;
N196W+A222V;
N196W+A222E;
N196W+A222I;
S199G+A222V;
S199G+A222E;
S199G+A222I;
N196W+S199G+A222I;
Q134L;
L150W+N156K+N196W+S199G+A222V;
L150Y+N156K+N196W+S199G+A222I;
L150W+N196W+S199G+A222I+A428S;
L150F+N156K+N196W+S199G+A222I;
L150Y+N156R+N196W+A222V;
L150M+N156R+N196W+S199G+A222I;
L150M+N156R+N196W+A222V;
L150Y+N156R+N196W+S199G+A222V;
L150M+N156K+N196W+S199G+A222V;
L150Y+N156R+N196W+A222I;
L150H+N156R+N196W+S199G+A222I;
L150H+N156K+N196W+A222V;
L150W+N156R+N196W+A222I;
L150F+N156R+N196W+A222I;
L150F+N156K+N196W+S199G+A222V;
L150H+N156K+N196W+S199G+A222V;
L150F+N156R+S199G+A222I;
L150M+N156K+N196W+A222V;
L150W+N156K+N196W+S199G+A222I;
N156K+N196W+S199G+A222V;
L150Y+N156R+S199G+A222I;
L150M+N156R+S199G+A222I;
L150W+N156K+S199G+A222V;
L150W+N156R+N196W+S199G+A222V;
L150Y+N156R+N196W;
N156K+N196W+A222V;
N156K+N196W+S199G;
N156R+S199G+A222V;
S113H+N196W+S199G+A222V;
Q71E+S113H+N196W+S199G+A222V;
N196W+S199G+A222V+D283A;
N196W+S199G+A222V+D283P;
W142E+D193SQY+N196W+S199G+A222V+R224K;
E96K+K101R+L150W+N156R+D179S+N196W+S199G+T208N+A222V;

E96K+K101R+L150Y+N156R+D179S+N196W+S199G+T208N+A222V+E284Q;
E96K+K101R+L150M+N156R+D179S+N196W+S199G+T208N+A222V+E284Q;
S113Q+Q134E+N196W+S199G+A222V;
S113D+Q134N+N196W+S199G+A222V;
S113F+N196W+S199G+A222V;
E171Q+N196W+S199G+N204D+A222V;
N196W+S199G+A222V+H241N+S245N+T278N+E284Q+E285V;
N196W+S199G+A222V+S394K+A414K+K417Y;
N196W+S199G+A222V+E359Y+S394K+K396S+A414K+K417Y;
R38H+E96K+G99N+K101R+D179S+N196W+S199G+A222V;
R38H+E96K+G99N+K101R+D179S+N196W+S199G+A222V+E284Q;
V107T+H110D+N196W+S199G+A222V;
Q134T+L150Y+N196W+S199G+A222V;
S113F+L150W+N196W+S199G+A222V;
S113F+L150Y+N196W+S199G+A222V;
E96K+K101R+N156R+D179S+N196W+S199G+T208N+A222V;
E96K+K101R+L150Y+N156R+D179S+N196W+S199G+T208N+A222V;
E96K+K101R+L150M+N156R+D179S+N196W+S199G+T208N+A222V;
E96K+K101R+N156R+D179S+N196W+S199G+T208N+A222V+E284Q;
E96K+K101R+L150W+N156R+D179S+N196W+S199G+T208N+A222V+E284Q;
N28R+Q86R+N196W+S199G+A222V;
N28R+Q86R+K89R+N196W+S199G+A222V;
G56P+N196W+S199G+S209L+A222V;
E96K+N196W+S199G+A222V;
T10I+N196W+S199G+A222V;
D39R+N196W+S199G+A222V;
R64S+N196W+S199G+A222V;
T10I+D39R+R64S+N196W+S199G+A222V;
T10I+D39R+N196W+S199G+A222V;
D39R+E96K+N196W+S199G+A222V;
R64S+D90E+E96K+N196W+S199G+A222V;
R38H+D39R+E96K+G99N+K101R+D179S+N196W+S199G+A222V;
R38H+R64S+E96K+G99N+K101R+D179S+N196W+S199G+A222V;
T10I+R38H+R64S+E96K+G99N+K101R+D179S+N196W+S199G+A222V;
T10I+R38H+R64S+D90E+E96K+G99N+K101R+D179S+N196W+S199G+A222V;
T10I+R38H+D39R+E96K+G99N+K101R+D179S+N196W+S199G+A222V;
R38H+D39R+R64S+E96K+G99N+K101R+D179S+N196W+S199G+A222V;
E96K+N196W+S199G+A222V+E284Q;
T10I+N196W+S199G+A222V+E284Q;
D39R+N196W+S199G+A222V+E284Q;
R64S+N196W+S199G+A222V+E284Q;
T10I+D39R+E96K+N196W+S199G+A222V+E284Q;
D193SQY+N196W+S199G+A222V;
Q134T+N196W+S199G+A222V;
L1741+N196W+S199G+T208N+A222V;
Y183F+N196W+S199G+T208S+A222V;
N127D+N156R+N196W+S199G+A222V;
Q134T+L150W+N196W+S199G+A222V;
N57P+N196W+S199G+A222V;
N196W+S199G+Q200W+A222V;
T10I+D39R+R64S+E96K+N196W+S199G+A222V+E284Q;
T10I+D39R+R64S+N196W+S199G+A222V+E284Q;
T10I+R64S+E96K+N196W+S199G+A222V+E284Q;
D39R+R64S+D90E+E96K+N196W+S199G+A222V+E284Q;
T10I+R64S+E96K+N196W+S199G+A222V;
T10I+D39R+N196W+S199G+A222V+E284Q;
D39R+E96K+N196W+S199G+A222V+E284Q;
D39R+R64S+N196W+S199G+A222V+E284Q;
R64S+E96K+N196W+S199G+A222V+E284Q;
D39R+R64S+N196W+S199G+A222V;
S12*+S13*+V14*+K15*+N16*+I103Y+N196W+S199G+A222V+N233S+T308Y;
S12*+S13*+V14*+K15*+N16*+A43D+I103Y+N196W+S199G+A222V+N233S+T308M;
V9L+S12P+V14I+N16S+A43T+N196W+S199G+A222V;
S12*+S13*+V14*+K15*+N16*+N196W+S199G+A222V;
N28W+N196W+S199G+A222V;
N196W+S199G+A222V+N392W+K417W;
T10I+D39R+E96K+N196W+S199G+A222V;
V9D+R38H+N196W+S199G+A222V+T348K;
S113F+L150Y+N156K+N196W+S199G+A222V;
S113Y+L150Y+N156K+N196W+S199G+A222V;
S113W+L150Y+N156K+N196W+S199G+A222V;
S113F+N156K+N196W+S199G+A222V;
S113Y+N156K+N196W+S199G+A222V;
S113W+N156K+N196W+S199G+A222V;
W138Y+L150V+N196W+S199G+A222V;
W138Y+L150V+D179G+N196W+S199G+A222V;
W138Y+L150V+N196W+S199G+L218W+A222V;
E96K+Q134L+D179S+N196W+S199G+A222V+E284Q;
E96K+Q134L+L150Y+N156R+D179S+N196W+S199G+A222V+E284Q;
E96K+L150Y+N156R+D179S+N196W+S199G+A222V+E284Q;
R38H+E96K+G99N+K101R+Q134L+D179S+N196W+S199G+S221N+A222V;
R38H+E96K+G99N+K101R+Q134L+D179S+N196W+S199G+A222V;
R38H+E96K+G99N+K101R+Q134L+L150Y+N156R+D179S+N196W+S199G+A222V;
R38H+E96K+G99N+K101R+L150Y+N156R+D179S+N196W+S199G+A222V;
L150F+N196W+S199G+A222I;
Q134L+L150F+N156R+N196W+S199G+A222I;
Q134L+L150H+N156R+N196W+S199G+A222I;
Q134L+L150M+N156K+N196W+S199G+A222I;
Q134L+L150Y+N156K+N196W+S199G+A222I+Q457L;
Q134M+L150W+N156K+N196W+S199G+A222I;
Q134W+L150W+N156K+N196W+S199G+A222I;
L150W+L152M+N156K+N196W+S199G+A222I;
S113F+L150W+N156K+N196W+S199G+A222I;
S113Y+L150W+N156K+N196W+S199G+A222I;
L150W+G151W+N156K+N196W+S199G+A222I;
L150W+G151S+N156K+N196W+S199G+A222I;
S113F+L150W+G151S+N156K+N196W+S199G+A222I;
Y67W+W68Y+L150W+N156K+N196W+S199G+A222I;
A43V+L150M+G151F+N156R+N196W+S199G+A222I;
L150M+G151Y+N156R+N196W+S199G+A222I;

L150M+G151W+N156R+N196W+S199G+A222I;
L150M+G151S+N156R+N196W+S199G+A222I+Y534H;
S113F+L150M+G151S+N156R+N196W+S199G+A222I;
Q134L+L150F+N156K+N196W+S199G+A222I;
L150W+G151F+N156K+N196W+S199G+A222I;
L150W+G151Y+N156K+N196W+S199G+A222I;
Y67W+W68Y+L150W+N156K+N196W+S199G+A222I;
G56W+N57P+Y67W+W68Y+L150W+N156K+N196W+S199G+A222I;
K541+Y67W+W68S+S113G+N196W+S199G+A222V+A382T;
K54I+Y67W+W68S+S113G+D114Q+L150V+N196W+S199G+A222V;
K54I+Y67W+W68S+S113G+W138Y+N196W+S199G+A222V;
K54I+Y67W+W68S+S113G+D114Q+W138Y+L150V+N196W+S199G+A222V;
Q134L+N196W+S199G+A222V;
V107T+I108L+H110D+F169H+N196W+S199G+A222V;
N196W+S199G+A222V+N392W+K417W;
V9D+R38H+N196W+S199G+A222V+T348K;
E96H+L150Y+N156R+N196W+S199G+A222V+E284Q;
Q134L+L150Y+N196W+S199G+A222V;
L150Y+N196W+S199G+A222V;
Q134L+L150Y+N196W+S199G+A222V;
L150F+N156R+N196W+S199G+A222V;
L150H+N156R+N196W+S199G+A222V;
Q134L+L150F+N156R+N196W+S199G+A222V;
Q134L+L150H+N156R+N196W+S199G+A222V;
Q134L+L150F+N156K+N196W+S199G+A222V;
Q134L+L150H+N156K+N196W+S199G+A222V;
Q134L+L150Y+N156K+N196W+S199G+A222V;
L150Y+N156K+N196W+S199G+A222V;
Q134L+L150Y+N156K+N196W+S199G+A222V;
Q134W+L150Y+N156K+N196W+S199G+A222V;
Q134M+L150Y+N156K+N196W+S199G+A222V;
Q134M+L150Y+N156K+N196W+S199G+A222V+A466V;
L150Y+L152M+N156K+N196W+S199G+A222V;
L150S+N196W+S199G+A222V;
N196W+S199G+A222V+N281S;
Y67T+N196W+S199G+A222V;
Q71N+N196W+S199G+A222V;
Q71N+A94D+N196W+S199G+A222V;
N196W+S199G+L218F+A222V;
N196W+S199G+L218W+A222V;
N196W+S199G+A222V+T278W;
N196W+S199G+A222V+T278W+T459M;
N196W+S199G+A222V+T278Y;
N196W+S199G+A222V+S275N;
N196W+S199G+A222V+S275L;
N196W+S199G+A222V+S335Q;
N196W+S199G+A222V+S335K;
N196W+S199G+A222V+S335R;
N196W+S199G+L218W+A222V+S335K;
N196W+S199G+L218W+A222V+S335Q;
Y67W+N196W+S199G+A222V;
N196W+S199G+A222V+N281Q;
L150M+N156R+N196W+S199G+A222V;
Q134L+L150M+N156R+N196W+S199G+A222V;
Q134L+L150M+N156K+N196W+S199G+A222V;
D39R+N196W+S199G+A222V+N281Q+E284Q;
D39R+N196W+S199G+A222V+E284Q+Q479QP;
D39R+Y70F+N196W+S199G+A222V+E284Q;
N28W+D39R+N196W+S199G+A222V+E284Q;
D39R+N196W+S199G+N207W+A222V+E284Q;
E1*+T2*+A3*+N4*+K5*+S6*+N7*+K8*+D39R+N196W+S199G+N207W+A222V+E284Q;
N196W+N207W;
N196W+N207W+E284Q;
E1*+T2*+A3*+N4*+K5*+S6*+N7*+K8*+N196W+N207W+E284Q;
L150Y+N196W+S199G+A222V;
E1*+T2*+A3*+N4*+K5*+S6*+N7*+K8*+L150Y+N196W+S199G+A222V;
E96K+K101R+L150M+N156R+D179S+N196W+S199G+N207W+T208N+A222V;
E1*+T2*+A3*+N4*+K5*+S6*+N7*+K8*+E96K+K101R+L150M+N156R+D179S+N196W+S199G+T208N+A222V;
Q134L+L150H+N156R+N196W+S199G+A222I+E284Q;
E1*+T2*+A3*+N4*+K5*+S6*+N7*+K8*+Q134L+L150H+N156R+N196W+S199G+A222I;
E1*+T2*+A3*+N4*+K5*+S6*+N7*+K8*+Q134L+L150H+N156R+N196W+S199G+N207W+A222I+E284Q;
E96K+D179S+N196W+S199G+A222V+E284Q;
E1*+T2*+A3*+N4*+K5*+S6*+N7*+K8*+E96K+D179S+N196W+S199G+A222V+E284Q;
R64S+E96K+N196W+S199G+N207W+A222V;
N28W+D39R+N196W+S199G+N207W+A222V+E284Q;
D39R+N196W+S199G+A222V+E284Q;
D39R+N196W+S199G+N207W+A222V+E284Q;
E1*+T2*+A3*+N4*+K5*+S6*+N7*+K8*+D39R+N196W+S199G+A222V+E284Q;
E1*+T2*+A3*+N4*+K5*+S6*+N7*+K8*+N196W+N207W+E511D;
L150Y+N196W+S199G+N207W+A222V;
E96K+K101R+L150M+N156R+D179S+N196W+S199G+T208N+A222V;
E96K+K101R+L150M+N156R+D179S+N196W+S199G+T208N+A222V+E284Q;
E1*+T2*+A3*+N4*+K5*+S6*+N7*+K8*+E96K+K101R+L150M+N156R+D179S+N196W+S199G+N207W+T208N+A222V+E284Q;
Q134L+L150H+N156R+N196W+S199G+A222I;
N28W+E96K+D179S+N196W+S199G+A222V+E284Q;
R64S+E96K+N196W+S199G+A222V;
R64S+E96K+N196W+S199G+A222V+E284Q; and
E1*+T2*+A3*+N4*+K5*+S6*+N7*+K8*+R64S+E96K+N196W+S199G+A222V;

and wherein the variant has alpha-amylase activity and wherein the variant has at least 70%, but less than 100% sequence identity, to the polypeptide of SEQ ID NO: 1.

10. The variant of claim 9, wherein the variant further comprises a C-terminal deletion, H626*.

11. The variant of claim 1, comprising a combination of alterations selected from:

N196W+V599W+H626*;
N196W+H550Y+P605S+H626*;
N196W+A545P+T576Y+H626*;
N196W+K549Y+G560P+H626*;
I108P+Y183I+N196W+I205Y+H626*;
N196W+R323K+H626*;
N196W+D283P+H626*;

W138Y+N196W+H626*;
N196W+N392W+K417W+H626*;
N196W+N392R+K417W+H626*;
N196W+K549*+H550*+D551*+H626*;
N196W+P580*+E581*+N582*+H626*;
N196W+F592FK+H626*;
N28W+N196W+N207W+S386D+N603W+H626*;
R38Y+N196W+H626*;
N196W+H259Y+H626*;
N196W+Q412W+H626*;
N196W+F212W+H626*;
N196W+V599W+H626*;
N196W+H550Y+P605S+H626*;
N196W+H550Y+K589F+H626*;
N196W+H550Y+D608Y+H626*;
N196W+M574W+L614W+H626*;
N196W+G533H+M574W+L614W+H626*;
N196W+V543P+N570H+H626*;
N196W+G533H+Y575W+L614W+H626*;
N196W+A545P+T576Y+H626*;
N196W+A566P+T578Y+H626*;
N196W+K549Y+G560P+H626*;
N196W+A566P+L577Y+H626*;
N196W+I547Y+G560P+H626*;
N196W+M574MW+H626*;
N196W+K549*+H550*+D551*+M574MW+P580*+E581*+N582*+F592FK+H626*;
N196W+L614W+G619W+H626*;
N28W+I108P+N196W+N207W+S386D+A466V+Q542K+N603W+H626*;
N28W+I108P+N196W+N207W+S386D+N603W+H626*;
N196W+D282P+D283*+H626*;
W138Y+N196W+H626*;
N28W+N196W+N207W+S386D+N603W+H626*;
N196W+S388W+A424P+H626*;
N196W+S388W+A424P+L489Q+H626*;
A117T+N196W+H550Y+D608Y+H626*;
N196W+Q457R+Y575W+L614W+H626*;
N196W+S199G;
N196W+A222V;
N196W+A222E;
N196W+A222I;
N196W+S199G+A222I;
L150W+N156K+N196W+S199G+A222V;
L150Y+N156K+N196W+S199G+A222I;
L150W+N196W+S199G+A222I+A428S;
L150F+N156K+N196W+S199G+A222I;
L150Y+N156R+N196W+A222V;
L150M+N156R+N196W+S199G+A222I;
L150M+N156R+N196W+A222V;
L150Y+N156R+N196W+S199G+A222V;
L150M+N156K+N196W+S199G+A222V;
L150Y+N156R+N196W+A222I;
L150H+N156R+N196W+S199G+A222I;
L150H+N156K+N196W+A222V;
L150W+N156R+N196W+A222I;
L150F+N156R+N196W+A222I;
L150F+N156K+N196W+S199G+A222V;
L150H+N156K+N196W+S199G+A222V;
L150M+N156K+N196W+A222V;
L150W+N156K+N196W+S199G+A222I;
N156K+N196W+S199G+A222V;
L150W+N156R+N196W+S199G+A222V;
L150Y+N156R+N196W;
N156K+N196W+A222V;
N156K+N196W+S199G;
S113H+N196W+S199G+A222V;
Q71E+S113H+N196W+S199G+A222V;
N196W+S199G+A222V+D283A;
N196W+S199G+A222V+D283P;
W142E+D193SQY+N196W+S199G+A222V+R224K;
E96K+K101R+L150W+N156R+D179S+N196W+S199G+T208N+A222V;
E96K+K101R+L150Y+N156R+D179S+N196W+S199G+T208N+A222V+E284Q;
E96K+K101R+L150M+N156R+D179S+N196W+S199G+T208N+A222V+E284Q;
S113Q+Q134E+N196W+S199G+A222V;
S113D+Q134N+N196W+S199G+A222V;
S113F+N196W+S199G+A222V;
E171Q+N196W+S199G+N204D+A222V;
N196W+S199G+A222V+H241N+S245N+T278N+E284Q+E285V;
N196W+S199G+A222V+S394K+A414K+K417Y;
N196W+S199G+A222V+E359Y+S394K+K396S+A414K+K417Y;
R38H+E96K+G99N+K101R+D179S+N196W+S199G+A222V;
R38H+E96K+G99N+K101R+D179S+N196W+S199G+A222V+E284Q;
V107T+H110D+N196W+S199G+A222V;
Q134T+L150Y+N196W+S199G+A222V;
S113F+L150W+N196W+S199G+A222V;
S113F+L150Y+N196W+S199G+A222V;
E96K+K101R+N156R+D179S+N196W+S199G+T208N+A222V;
E96K+K101R+L150Y+N156R+D179S+N196W+S199G+T208N+A222V;
E96K+K101R+L150M+N156R+D179S+N196W+S199G+T208N+A222V;
E96K+K101R+N156R+D179S+N196W+S199G+T208N+A222V+E284Q;
E96K+K101R+L150W+N156R+D179S+N196W+S199G+T208N+A222V+E284Q;
N28R+Q86R+N196W+S199G+A222V;
N28R+Q86R+K89R+N196W+S199G+A222V;
G56P+N196W+S199G+S209L+A222V;
E96K+N196W+S199G+A222V;
T10I+N196W+S199G+A222V;
D39R+N196W+S199G+A222V;
R64S+N196W+S199G+A222V;
T10I+D39R+R64S+N196W+S199G+A222V;
T10I+D39R+N196W+S199G+A222V;
D39R+E96K+N196W+S199G+A222V;
R64S+D90E+E96K+N196W+S199G+A222V;
R38H+D39R+E96K+G99N+K101R+D179S+N196W+S199G+A222V;
R38H+R64S+E96K+G99N+K101R+D179S+N196W+S199G+A222V;
T10I+R38H+R64S+E96K+G99N+K101R+D179S+N196W+S199G+A222V;
T10I+R38H+R64S+D90E+E96K+G99N+K101R+D179S+N196W+S199G+A222V;
T10I+R38H+D39R+E96K+G99N+K101R+D179S+N196W+S199G+A222V;
R38H+D39R+R64S+E96K+G99N+K101R+D179S+N196W+S199G+A222V;
E96K+N196W+S199G+A222V+E284Q;
T10I+N196W+S199G+A222V+E284Q;
D39R+N196W+S199G+A222V+E284Q;
R64S+N196W+S199G+A222V+E284Q;
T10I+D39R+E96K+N196W+S199G+A222V+E284Q;
D193SQY+N196W+S199G+A222V;

Q134T+N196W+S199G+A222V;
L1741+N196W+S199G+T208N+A222V;
Y183F+N196W+S199G+T208S+A222V;
N127D+N156R+N196W+S199G+A222V;
Q134T+L150W+N196W+S199G+A222V;
N57P+N196W+S199G+A222V;
N196W+S199G+Q200W+A222V;
T10I+D39R+R64S+E96K+N196W+S199G+A222V+E284Q;
T10I+D39R+R64S+N196W+S199G+A222V+E284Q;
T10I+R64S+E96K+N196W+S199G+A222V+E284Q;
D39R+R64S+D90E+E96K+N196W+S199G+A222V+E284Q;
T10I+R64S+E96K+N196W+S199G+A222V;
T10I+D39R+N196W+S199G+A222V+E284Q;
D39R+E96K+N196W+S199G+A222V+E284Q;
D39R+R64S+N196W+S199G+A222V+E284Q;
R64S+E96K+N196W+S199G+A222V+E284Q;
D39R+R64S+N196W+S199G+A222V;
S12*+S13*+V14*+K15*+N16*+I103Y+N196W+S199G+A222V+N233S+T308Y;
S12*+S13*+V14*+K15*+N16*+A43D+I103Y+N196W+S199G+A222V+N233S+T308M;
V9L+S12P+V14I+N16S+A43T+N196W+S199G+A222V;
S12*+S13*+V14*+K15*+N16*+N196W+S199G+A222V;
N28W+N196W+S199G+A222V;
N196W+S199G+A222V+N392W+K417W;
T10I+D39R+E96K+N196W+S199G+A222V;
V9D+R38H+N196W+S199G+A222V+T348K;
S113F+L150Y+N156K+N196W+S199G+A222V+H626*;
S113Y+L150Y+N156K+N196W+S199G+A222V+H626*;
S113W+L150Y+N156K+N196W+S199G+A222V+H626*;
S113F+N156K+N196W+S199G+A222V+H626*;
S113Y+N156K+N196W+S199G+A222V+H626*;
S113W+N156K+N196W+S199G+A222V+H626*;
W138Y+L150V+N196W+S199G+A222V+H626*;
W138Y+L150V+D179G+N196W+S199G+A222V+H626*;
W138Y+L150V+N196W+S199G+L218W+A222V+H626*;
E96K+Q134L+D179S+N196W+S199G+A222V+E284Q+H626*;
E96K+Q134L+L150Y+N156R+D179S+N196W+S199G+A222V+E284Q+H626*;
E96K+L150Y+N156R+D179S+N196W+S199G+A222V+E284Q+H626*;
R38H+E96K+G99N+K101R+Q134L+D179S+N196W+S199G+S221N+A222V+H626*;
R38H+E96K+G99N+K101R+Q134L+D179S+N196W+S199G+A222V+H626*;
R38H+E96K+G99N+K101R+Q134L+L150Y+N156R+D179S+N196W+S199G+A222V+H626*;
R38H+E96K+G99N+K101R+L150Y+N156R+D179S+N196W+S199G+A222V+H626*;
L150F+N196W+S199G+A222I+H626*;
Q134L+L150F+N156R+N196W+S199G+A222I+H626*;
Q134L+L150H+N156R+N196W+S199G+A222I+H626*;
Q134L+L150M+N156K+N196W+S199G+A222I+H626*;
Q134L+L150Y+N156K+N196W+S199G+A222I+Q457L+H626*;
Q134M+L150W+N156K+N196W+S199G+A222I+H626*;
Q134W+L150W+N156K+N196W+S199G+A222I+H626*;
L150W+L152M+N156K+N196W+S199G+A222I+H626*;
S113F+L150W+N156K+N196W+S199G+A222I+H626*;
S113Y+L150W+N156K+N196W+S199G+A222I+H626*;
L150W+G151W+N156K+N196W+S199G+A222I+H626*;
L150W+G151S+N156K+N196W+S199G+A222I+H626*;
S113F+L150W+G151S+N156K+N196W+S199G+A222I+H626*;
Y67W+W68Y+L150W+N156K+N196W+S199G+A222I+H626*;
A43V+L150M+G151F+N156R+N196W+S199G+A222I;
L150M+G151Y+N156R+N196W+S199G+A222I;
L150M+G151W+N156R+N196W+S199G+A222I;
L150M+G151S+N156R+N196W+S199G+A222I+Y534H;
S113F+L150M+G151S+N156R+N196W+S199G+A222I;
Q134L+L150F+N156K+N196W+S199G+A222I+H626*;
L150W+G151F+N156K+N196W+S199G+A222I+H626*;
L150W+G151Y+N156K+N196W+S199G+A222I+H626*;
Y67W+W68Y+L150W+N156K+N196W+S199G+A222I;
G56W+N57P+Y67W+W68Y+L150W+N156K+N196W+S199G+A222I+H626*;
K54I+Y67W+W68S+S113G+N196W+S199G+A222V+A382T+H626*;
K541+Y67W+W68S+S113G+D114Q+L150V+N196W+S199G+A222V+H626*;
K54I+Y67W+W68S+S113G+W138Y+N196W+S199G+A222V+H626*;
K54I+Y67W+W68S+S113G+D114Q+W138Y+L150V+N196W+S199G+A222V+H626*;
Q134L+N196W+S199G+A222V+H626*;
V107T+I108L+H110D+F169H+N196W+S199G+A222V+H626*;
N196W+S199G+A222V+N392W+K417W+H626*;
V9D+R38H+N196W+S199G+A222V+T348K+H626*;
E96H+L150Y+N156R+N196W+S199G+A222V+E284Q+H626*;
Q134L+L150Y+N196W+S199G+A222V+H626*;
L150Y+N196W+S199G+A222V+H626*;
Q134L+L150Y+N196W+S199G+A222V+H626*;
L150F+N156R+N196W+S199G+A222V+H626*;
L150H+N156R+N196W+S199G+A222V+H626*;
Q134L+L150F+N156R+N196W+S199G+A222V+H626*;
Q134L+L150H+N156R+N196W+S199G+A222V+H626*;
Q134L+L150F+N156K+N196W+S199G+A222V+H626*;
Q134L+L150H+N156K+N196W+S199G+A222V+H626*;

Q134L+L150Y+N156K+N196W+S199G+A222V+H626*;
L150Y+N156K+N196W+S199G+A222V+H626*;
Q134L+L150Y+N156K+N196W+S199G+A222V+H626*;
Q134W+L150Y+N156K+N196W+S199G+A222V+H626*;
Q134M+L150Y+N156K+N196W+S199G+A222V+H626*;
Q134M+L150Y+N156K+N196W+S199G+A222V+A466V+H626*;
L150Y+L152M+N156K+N196W+S199G+A222V+H626*;
L150S+N196W+S199G+A222V+H626*;
N196W+S199G+A222V+N281S+H626*;
Y67T+N196W+S199G+A222V+H626*;
Q71N+N196W+S199G+A222V+H626*;
Q71N+A94D+N196W+S199G+A222V+H626*;
N196W+S199G+L218F+A222V+H626*;
N196W+S199G+L218W+A222V+H626*;
N196W+S199G+A222V+T278W+H626*;
N196W+S199G+A222V+T278W+T459M+H626*;
N196W+S199G+A222V+T278Y+H626*;
N196W+S199G+A222V+S275N+H626*;
N196W+S199G+A222V+S275L+H626*;
N196W+S199G+A222V+S335Q+H626*;
N196W+S199G+A222V+S335K+H626*;
N196W+S199G+A222V+S335R+H626*;
N196W+S199G+L218W+A222V+S335K+H626*;
N196W+S199G+L218W+A222V+S335Q+H626*;
Y67W+N196W+S199G+A222V+H626*;
N196W+S199G+A222V+N281Q+H626*;
L150M+N156R+N196W+S199G+A222V+H626*;
Q134L+L150M+N156R+N196W+S199G+A222V+H626*;
Q134L+L150M+N156K+N196W+S199G+A222V+H626*;
D39R+N196W+S199G+A222V+N281Q+E284Q;
D39R+N196W+S199G+A222V+E284Q+Q479QP;
D39R+Y70F+N196W+S199G+A222V+E284Q;
N28W+D39R+N196W+S199G+A222V+E284Q;
D39R+N196W+S199G+N207W+A222V+E284Q;
E1*+T2*+A3*+N4*+K5*+S6*+N7*+K8*+D39R+N196W+S199G+N207W+A222V+E284Q+H626*;
N196W+N207W;
N196W+N207W+E284Q;
E1*+T2*+A3*+N4*+K5*+S6*+N7*+K8*+N196W+N207W+E284Q;
L150Y+N196W+S199G+A222V+H626*;
E1*+T2*+A3*+N4*+K5*+S6*+N7*+K8*+L150Y+N196W+S199G+A222V;
E96K+K101R+L150M+N156R+D179S+N196W+S199G+N207W+T208N+A222V;
E1*+T2*+A3*+N4*+K5*+S6*+N7*+K8*+E96K+K101R+L150M+N156R+D179S+N196W+S199G+T208N+A222V;
Q134L+L150H+N156R+N196W+S199G+A222I+E284Q+H626*;
E1*+T2*+A3*+N4*+K5*+S6*+N7*+K8*+Q134L+L150H+N156R+N196W+S199G+A222I+H626*;
E1*+T2*+A3*+N4*+K5*+S6*+N7*+K8*+Q134L+L150H+N156R+N196W+S199G+N207W+A222I+E284Q;
E96K+D179S+N196W+S199G+A222V+E284Q+H626*;
E1*+T2*+A3*+N4*+K5*+S6*+N7*+K8*+E96K+D179S+N196W+S199G+A222V+E284Q;
R64S+E96K+N196W+S199G+N207W+A222V;
N28W+D39R+N196W+S199G+N207W+A222V+E284Q;
D39R+N196W+S199G+A222V+E284Q+H626*;
D39R+N196W+S199G+N207W+A222V+E284Q;
E1*+T2*+A3*+N4*+K5*+S6*+N7*+K8*+D39R+N196W+S199G+A222V+E284Q;
E1*+T2*+A3*+N4*+K5*+S6*+N7*+K8*+N196W+N207W+E511D;
L150Y+N196W+S199G+N207W+A222V;
E96K+K101R+L150M+N156R+D179S+N196W+S199G+T208N+A222V+H626*;
E96K+K101R+L150M+N156R+D179S+N196W+S199G+T208N+A222V+E284Q;
E1*+T2*+A3*+N4*+K5*+S6*+N7*+K8*+E96K+K101R+L150M+N156R+D179S+N196W+S199G+N207W+T208N+A222V+E284Q+H626*;
Q134L+L150H+N156R+N196W+S199G+A222I;
N28W+E96K+D179S+N196W+S199G+A222V+E284Q;
R64S+E96K+N196W+S199G+A222V+H626*;
R64S+E96K+N196W+S199G+A222V+E284Q; and
E1*+T2*+A3*+N4*+K5*+S6*+N7*+K8*+R64S+E96K+N196W+S199G+A222V;

and wherein the variant has alpha-amylase activity and wherein the variant has at least 70%, but less than 100% sequence identity, to the polypeptide of SEQ ID NO: 1.

12. The variant of claim 1, wherein the alpha-amylase comprises combinations of alterations selected from:
N196W+H626*;
N196W+S199G+A222V+H 626*;
N196W+N207W+H626*;
L150Y+N196W+S199G+A222V;
E96K+D179S+N196W+S199G+A222V+E284Q; and
R64S+E96K+N196W+S199G+A222V;

and wherein the variant has alpha-amylase activity and wherein the variant has at least 70%, but less than 100% sequence identity, to the polypeptide of SEQ ID NO: 1.

13. The variant of claim 5, wherein increased pH stability at pH 4.0 can be determined as % residual alpha-amylase activity (% RA) after incubation of the variant amylase at pH 4.0, 32° C, for 18-24 hours.

14. The variant of claim 5, wherein increased pH stability at pH 4.0 can be determined as residual alpha-amylase activity after incubation of the variant amylase at pH 4.0, 32° C, for 96 hours, and calculation of enzyme half-life in hours.

15. The variant of claim 1, wherein half-life is increased compared to the parent amylase of SEQ ID NO: 1 of at least a factor 1.2.

16. The variant of claim 1, further comprising a substitution corresponding to K8N.

17. The variant alpha-amylase of claim 1, comprising at least the catalytic domain, comprised in amino acids 12-438 of SEQ ID NO: 1, wherein the variant has alpha-amylase activity and wherein the catalytic domain has at least 70%, but less than 100% sequence identity, to the polypeptide of SEQ ID NO: 1, and wherein the variant optionally has a carbohydrate binding module (CBM).

18. The variant of claim 17, wherein the variant has a CBM, and/or a linker and the linker and/or the CBM has been replaced with a heterologous CBM.

19. An isolated polynucleotide encoding an alpha-amylase variant, comprising an N196W solution and alteration at one or more positions corresponding to positions 196, 1, 2, 3, 4, 5, 6, 7, 8, 9, 10, 11, 13, 15, 28, 38, 39, 43, 54, 56, 57, 67, 68, 70, 71, 86, 89, 90, 94, 96, 99, 101, 103, 107, 110, 113, 114, 117, 127, 134, 138, 142, 150, 151, 152, 156, 169, 171, 174, 179, 183, 193, 199, 200, 204, 205, 207, 208, 209, 212, 218, 221, 222, 224, 233, 241, 245, 259, 275, 278, 281, 282, 283, 284, 285, 308, 323, 335, 348, 359, 382, 386, 388, 392, 394, 396, 412, 414, 417, 424, 428, 457, 459, 466, 479, 489, 511, 533, 534, 543, 545, 547, 549, 550, 551, 560, 566, 570, 575, 576, 577, 578, 580, 582, 589, 592, 599, 603, 605, 608, 614, 619, or 626 of the polypeptide of SEQ ID NO: 1, wherein the variant has alpha-amylase activity and wherein the variant has at least 70%, but less than 100% sequence identity, to the polypeptide of SEQ ID NO: 1.

20. A nucleic acid construct or expression vector comprising the polynucleotide of claim 19 operably linked to one or more control sequences that direct the production of the polypeptide in an expression host.

21. An isolated recombinant host cell comprising the polynucleotide of claim 19 operably linked to one or more control sequences that direct the production of the polypeptide.

22. A method of producing a variant alpha-amylase, comprising:

cultivating the recombinant host cell of claim 21 under conditions suitable for expression of the variant; and optionally recovering the variant.

23. A composition comprising the variant of claim 1.

24. A whole broth formulation or cell culture composition comprising the variant of claim 1.

25. A process of producing a fermentation product from starch-containing material comprising the steps of: (a) liquefying starch-containing material above the initial gelatinization temperature of said starch-containing material in the presence of an alpha amylase; (b) saccharifying the liquefied material; and (c) fermenting with a fermenting organism; wherein step (b) is carried out in the presence of at least a variant alpha-amylase, and optionally a glucoamylase, wherein the variant alpha-amylase comprises a N196W substitution and an alteration at one or more positions corresponding to positions 196, 1, 2, 3, 4, 5, 6, 7, 8, 9, 10, 11, 13, 15, 28, 38, 39, 43, 54, 56, 57, 67, 68, 70, 71, 86, 89, 90, 94, 96, 99, 101, 103, 107, 110, 113, 114, 117, 127, 134, 138, 142, 150, 151, 152, 156, 169, 171, 174, 179, 183, 193, 199, 200, 204, 205, 207, 208, 209, 212, 218, 221, 222, 224, 233, 241, 245, 259, 275, 278, 281, 282, 283, 284, 285, 308, 323, 335, 348, 359, 382, 386, 388, 392, 394, 396, 412, 414, 417, 424, 428, 457, 459, 466, 479, 489, 511, 533, 534, 543, 545, 547, 549, 550, 551, 560, 566, 570, 575, 576, 577, 578, 580, 582, 589, 592, 599, 603, 605, 608, 614, 619, or 626 of the polypeptide of SEQ ID NO: 1, wherein the variant has alpha-amylase activity and wherein the variant has at least 70%, but less than 100% sequence identity, to the polypeptide of SEQ ID NO: 1.

26. A process of producing a syrup product from starch-containing material, comprising the step of: (a) liquefying starch-containing material at a temperature above the initial gelatinization temperature of said starch-containing material in the presence of an alpha-amylase; (b) saccharifying the liquefied material in the presence of at least a variant alpha-amylase, and optionally a glucoamylase, wherein the variant alpha-amylase comprises a N196W substitution and an alteration at one or more positions corresponding to positions 196, 1, 2, 3, 4, 5, 6, 7, 8, 9, 10, 11, 13, 15, 28, 38, 39, 43, 54, 56, 57, 67, 68, 70, 71, 86, 89, 90, 94, 96, 99, 101, 103, 107, 110, 113, 114, 117, 127, 134, 138, 142, 150, 151, 152, 156, 169, 171, 174, 179, 183, 193, 199, 200, 204, 205, 207, 208, 209, 212, 218, 221, 222, 224, 233, 241, 245, 259, 275, 278, 281, 282, 283, 284, 285, 308, 323, 335, 348, 359, 382, 386, 388, 392, 394, 396, 412, 414, 417, 424, 428, 457, 459, 466, 479, 489, 511, 533, 534, 543, 545, 547, 549, 550, 551, 560, 566, 570, 575, 576, 577, 578, 580, 582, 589, 592, 599, 603, 605, 608, 614, 619, or 626 of the polypeptide of SEQ ID NO: 1, wherein the variant has alpha-amylase activity and wherein the variant has at least 70%, but less than 100% sequence identity, to the polypeptide of SEQ ID NO: 1.

27. A transgenic plant, plant part or plant cell comprising the variant alpha-amylase of claim 1.

28. The variant of claim 1, wherein the variant has alpha-amylase activity and wherein the variant has at least 80%, but less than 100% sequence identity, to the polypeptide of SEQ ID NO: 1.

29. The variant of claim 1, wherein the variant has alpha-amylase activity and wherein the variant has at least 85%, but less than 100% sequence identity, to the polypeptide of SEQ ID NO: 1.

30. The variant of claim 1, wherein the variant has alpha-amylase activity and wherein the variant has at least 90%, but less than 100% sequence identity, to the polypeptide of SEQ ID NO: 1.

31. The variant of claim 1, wherein the variant has alpha-amylase activity and wherein the variant has at least 95%, but less than 100% sequence identity, to the polypeptide of SEQ ID NO: 1.

32. The variant of claim 1, wherein the variant has alpha-amylase activity and wherein the variant has at least 97%, but less than 100% sequence identity, to the polypeptide of SEQ ID NO: 1.

33. The variant of claim 1, wherein the variant has alpha-amylase activity and wherein the variant has at least 99%, but less than 100% sequence identity, to the polypeptide of SEQ ID NO: 1.

* * * * *